US012297265B2

(12) United States Patent
Tian et al.

(10) Patent No.: US 12,297,265 B2
(45) Date of Patent: May 13, 2025

(54) ANTIBODY AND USE THEREOF

(71) Applicants: SICHUAN KELUN-BIOTECH BIOPHARMACEUTICAL CO., LTD., Sichuan (CN); KLUS PHARMA INC., Cranbury, NJ (US)

(72) Inventors: Haijun Tian, Cranbury, NJ (US); Sujun Deng, Cranbury, NJ (US); Chunxia Zhao, Cranbury, NJ (US); Hong Li, Cranbury, NJ (US); Dengnian Liu, Sichuan (CN); Hu Long, Sichuan (CN); Cheng Wang, Sichuan (CN); Liang Xiao, Sichuan (CN); Tongtong Xue, Sichuan (CN); Jingyi Wang, Sichuan (CN)

(73) Assignees: SICHUAN KELUN-BIOTECH BIOPHARMACEUTICAL CO., LTD., Chengdu (CN); KLUS PHARMA INC.

( * ) Notice: Subject to any disclaimer, the term of this patent is extended or adjusted under 35 U.S.C. 154(b) by 638 days.

(21) Appl. No.: 17/295,603

(22) PCT Filed: Dec. 19, 2019

(86) PCT No.: PCT/CN2019/126495
§ 371 (c)(1),
(2) Date: May 20, 2021

(87) PCT Pub. No.: WO2020/135201
PCT Pub. Date: Jul. 2, 2020

(65) Prior Publication Data
US 2023/0192840 A1 Jun. 22, 2023

(30) Foreign Application Priority Data
Dec. 28, 2018 (CN) .......................... 201811617535.8

(51) Int. Cl.
*C07K 16/28* (2006.01)
*A61K 31/337* (2006.01)
*A61K 39/395* (2006.01)
*A61K 47/68* (2017.01)
*A61P 35/00* (2006.01)
*C07K 16/46* (2006.01)
*G01N 33/574* (2006.01)
*A61K 39/00* (2006.01)

(52) U.S. Cl.
CPC ............ *C07K 16/28* (2013.01); *A61K 31/337* (2013.01); *A61K 39/3955* (2013.01); *A61K 47/6849* (2017.08); *A61P 35/00* (2018.01); *C07K 16/464* (2013.01); *G01N 33/57492* (2013.01); *A61K 2039/505* (2013.01); *C07K 2317/20* (2013.01); *C07K 2317/21* (2013.01); *C07K 2317/24* (2013.01); *C07K 2317/31* (2013.01); *C07K 2317/52* (2013.01); *C07K 2317/565* (2013.01); *C07K 2317/567* (2013.01); *C07K 2317/73* (2013.01); *C07K 2317/732* (2013.01); *C07K 2317/734* (2013.01); *C07K 2317/76* (2013.01); *C07K 2317/92* (2013.01)

(58) Field of Classification Search
CPC .. C07K 16/28; C07K 16/464; C07K 2317/20; C07K 2317/21; C07K 2317/24; C07K 2317/31; C07K 2317/52; C07K 2317/565; C07K 2317/567; C07K 2317/73; C07K 2317/732; C07K 2317/734; C07K 2317/76; C07K 2317/92; A61K 31/337; A61K 39/3955; A61K 47/6849; A61K 2039/505; A61K 39/39558; A61K 2300/00; A61K 31/513; A61K 31/555; A61K 31/704; A61P 35/00; G01N 33/57492
See application file for complete search history.

(56) References Cited

U.S. PATENT DOCUMENTS

| | | |
|---|---|---|
| 6,051,228 A | 4/2000 | Aruffo et al. |
| 2009/0169547 A1 | 7/2009 | Sahin et al. |
| 2010/0166779 A1 | 7/2010 | Sahin et al. |

(Continued)

FOREIGN PATENT DOCUMENTS

| | | | | |
|---|---|---|---|---|
| CA | 3030257 A1 | * | 1/2018 | .......... A61K 31/282 |
| CN | 1307484 A | | 8/2001 | |

(Continued)

OTHER PUBLICATIONS

Lopez, A. et. al. "Current therapeutic landscape for advanced gastroesophageal cancers", Feb. 2018, Ann. Transl. Med., 6(4), 1-19. (Year: 2018).*

(Continued)

*Primary Examiner* — Nelson B Moseley, II
*Assistant Examiner* — Alyssa Rae Stonebraker
(74) *Attorney, Agent, or Firm* — FINNEGAN, HENDERSON, FARABOW, GARRETT DUNNER LLP

(57) ABSTRACT

Provided herein is an anti-CLDN18.2 antibody or an antigen-binding fragment thereof, nucleic acid molecules for encoding the antibody and fragment, and method for preparing the antibody and fragment. The anti-CLDN18.2 antibody or the antigen-binding fragment thereof has high specificity and affinity to CLDN18.2, and can effectively bind to CLDN18.2 and mediate the killing of CLDN18.2 expressing cells. Also provided herein is a pharmaceutical composition comprising the antibody or the antigen-binding fragment thereof, and use thereof in the preparation of drugs for the prevention and/or treatment of tumors.

43 Claims, 10 Drawing Sheets
Specification includes a Sequence Listing.

(56) References Cited

U.S. PATENT DOCUMENTS

| | | |
|---|---|---|
| 2013/0149343 A1 | 6/2013 | Pesnell et al. |
| 2015/0157711 A1 | 6/2015 | Sahin et al. |
| 2018/0282390 A1* | 10/2018 | Voss .................. A61K 39/4644 |
| 2019/0233511 A1 | 8/2019 | Wang et al. |
| 2020/0347075 A1 | 11/2020 | Cai et al. |
| 2023/0192840 A1 | 6/2023 | Tian et al. |

FOREIGN PATENT DOCUMENTS

| | | |
|---|---|---|
| CN | 111110862 A | 5/2020 |
| EP | 1997832 A1 | 12/2008 |
| EP | 2311877 A2 | 4/2011 |
| JP | 2009517354 A | 4/2009 |
| JP | 2010528075 A | 8/2010 |
| JP | 2015500059 A | 1/2015 |
| JP | 2015518838 A | 7/2015 |
| JP | 2015-522543 A | 8/2015 |
| JP | 2016-500059 A | 1/2016 |
| JP | 2019531084 A | 10/2019 |
| JP | 2022515318 A | 2/2022 |
| WO | WO-2013/174403 A1 | 11/2013 |
| WO | WO 2013167153 A1 | 11/2013 |
| WO | WO 2013174404 A1 | 11/2013 |
| WO | WO 2013174510 A1 | 11/2013 |
| WO | WO-2014/075697 A1 | 5/2014 |
| WO | WO 2014075788 A1 | 5/2014 |
| WO | WO 2014146672 A1 | 9/2014 |
| WO | WO 2016165762 A1 | 10/2016 |
| WO | WO-2018/006882 A1 | 1/2018 |
| WO | WO-2018/054973 A1 | 3/2018 |
| WO | WO 2018054484 A1 | 3/2018 |
| WO | WO 2019174617 A1 | 9/2018 |
| WO | WO 2019114666 A1 | 6/2019 |
| WO | WO 2019149116 A1 | 8/2019 |
| WO | WO 2019154120 A1 | 8/2019 |
| WO | WO-2019/219089 A1 | 11/2019 |
| WO | WO-2019/242505 A1 | 12/2019 |
| WO | WO 2020023679 A1 | 1/2020 |
| WO | WO-2020/114480 A1 | 6/2020 |
| WO | WO 2020135201 A1 | 7/2020 |

OTHER PUBLICATIONS

International Search Report and Written Opinion mailed Mar. 18, 2020 in counterpart International Appl. PCT/CN2019/126495 with English translation (25 pgs.).

* cited by examiner

ANTIBODY AND USE THEREOF

CROSS-REFERENCE TO RELATED APPLICATIONS

The present application is the U.S. National Stage Entry of PCT International Application No. PCT/CN2019/126495, filed Dec. 19, 2019, which claims the benefit of priority from Chinese application No. 201811617535.8, filed on Dec. 28, 2018, the disclosures of which are incorporated herein by reference in their entirety.

SEQUENCE LISTING

The instant application contains a Sequence Listing which has been submitted in ASCII format via EFS-WEB and is hereby incorporated by reference in its entirety. Said ASCII copy, created on Nov. 11, 2021, is named 038873-0116_Sequence_Listing.txt and is 69,660 bytes.

FIELD OF THE INVENTION

The present invention relates to the field of therapeutic monoclonal antibodies, in particular an antibody specific to CLDN18.2 and use thereof in the treatment of diseases.

BACKGROUND OF THE INVENTION

Claudin 18.2 (CLDN 18.2) is a member of tight junction protein family Claudin. Tight junction proteins are a class of proteins that mediate tight junctions between cells. Different types of Claudin proteins are expressed in different tissues and are associated with different types of cancer. Claudin 1 is highly expressed in colon cancer, and Claudin 7 is associated with recurrence of liver cancer. The expression of Claudin 18.2 in normal tissues is restricted to gastric mucosal cells, and is not observed in other normal tissues. Meanwhile, Claudin 18.2 is expressed in 70% primary gastric adenocarcinoma and its metastases, and is also expressed in other cancers such as pancreatic cancer (50%), esophageal cancer (30%) and non-small cell lung cancer (25%). Among them, gastric cancer and pancreatic cancer have poor prognosis and high mortality, and the current demand for drugs is enormous.

Claudin 18.2 protein consists of four transmembrane regions, two extracellular loops and an intracellular loop, with its N-terminus and C-terminus in the cytoplasm. Two extracellular loops make it an ideal target for antibody. The sequence of Claudin 18.2 protein is highly conserved across species. Claudin 18.1, which belongs to the same protein family as Claudin 18.2, is specifically expressed in lung tissue. The sequences of Claudin 18.1 and Claudin 18.2 are highly homologous, only differ in 8 amino acids in the extracellular loop D1, which determines the epitope recognized by antibodies. The high similarity between Claudin 18.2 and Claudin 18.1 makes the development of drugs involving Claudin 18.2 specific antibodies very challenging.

Zolbetuximab (IMAB362) developed by Astellas is a human-mouse chimeric antibody of IgG1 type that targets Claudin 18.2. It binds to Claudin 18.2 expressed on tumor cells inducing antibody-dependent cellular cytotoxicity (ADCC) and complement dependent cytotoxicity (CDC). It also induces apoptosis and inhibits tumor cell proliferation.

However, there are no approved drugs involving antibodies binding to human CLDN18.2 in market. Therefore, it is urgent and necessary to develop an antibody targeting CLDN18.2 with higher specificity, lower toxic side effects, and better clinical efficacy, which will provide more drug options for cancer patients.

CONTENT OF THE INVENTION

Through the invention, the inventors first developed mouse antibodies having excellent properties. The antibodies specifically bind to CLDN 18.2 without binding to CLDN 18.1. Based on the earlier work, the inventors did a lot of creative work, and carried out in-depth research and modification of the mouse antibodies, thereby developed chimeric and humanized antibodies thereof. The humanized antibodies of the present invention not only have an extremely high degree of humanization, but also have substantially the same (or even better) biological functions as those of the mouse antibodies and the human-mouse chimeric antibodies which have the same heavy chain and light chain variable regions as the mouse antibodies.

Therefore, the antibodies of the present invention (especially the humanized antibodies) are extremely advantageous, which not only retain the function and properties of the parental mouse antibodies, for example, binding to human CLDN18.2 with high specificity and affinity, and have potential to be used in the prevention and treatment of tumors. The humanized antibody of the invention has an extremely high degree of humanization so that it can be safely administered to a human subject without triggering an immunogenic response. Therefore, the antibodies of the invention have significant clinical value.

Antibodies

In one aspect, the present invention provides an antibody or antigen binding fragment thereof that specifically binds to CLDN18.2.

In some embodiments, the antibody or antigen binding fragment thereof comprises the following complementarity determining regions (CDRs):

(a) CDR-H1, CDR-H2, and CDR-H3 of the heavy chain variable region (VH) shown in SEQ ID NO: 1; and/or CDR-L1, CDR-L2 and CDR-L3 of the light chain variable region (VL) shown in SEQ ID NO: 2;

or (b) CDR-H1, CDR-H2 and CDR-H3 of the VH shown in SEQ ID NO: 3, 39 or 40; and/or CDR-L1, CDR-L2 and CDR-L3 of the VL shown in SEQ ID NO: 4 or 41;

or (c) CDR-H1, CDR-H2 and CDR-H3 of the VH shown in SEQ ID NO: 44; and/or CDR-L1, CDR-L2 and CDR-L3 of the VL shown in SEQ ID NO:45;

or (d) CDR-H1, CDR-H2 and CDR-H3 of the VH shown in SEQ ID NO: 46; and/or CDR-L1, CDR-L2 and CDR-L3 of the VL shown in SEQ ID NO: 47;

or (e) CDR-H1, CDR-H2 and CDR-H3 of the VH shown in SEQ ID NO: 48; and/or CDR-L1, CDR-L2 and CDR-L3 of the VL shown in SEQ ID NO: 49;

or (f) CDR-H1, CDR-H2 and CDR-H3 of the VH shown in SEQ ID NO: 50; and/or CDR-L1, CDR-L2 and CDR-L3 of the VL shown in SEQ ID NO: 51;

or (g) CDR-H1, CDR-H2 and CDR-H3 of the VH shown in SEQ ID NO: 52; and/or CDR-L1, CDR-L2 and CDR-L3 of the VL shown in SEQ ID NO: 53;

(h) the above-mentioned heavy chain variable region (VH) and/or a light chain variable region (VL), wherein, said heavy chain variable region (VH) and/or light chain variable region (VL) comprises at least one CDR with a mutation compared with any of the VH and/or VL in (a) to (g), said mutation is a substitution, deletion, or addition of one or several amino acids (such as a substitution, deletion, or addition of 1, 2, or 3 amino acids); preferably, the substitution is a conservative substitution.

In certain preferred embodiments, the CDR is defined according to the Kabat, IMGT, Chothia or AbM numbering system; preferably, the VH and/or VL of the antibody or antigen-binding fragment thereof includes framework regions (FRs) derived from human or murine immunoglobulin, preferably, the antibody or antigen-binding fragment thereof binds to human CLDN 18.2.

In some embodiments, there is provided an antibody or antigen binding fragment thereof that specifically binds to CLDN18.2. The antibody or antigen binding fragment thereof comprises a heavy chain variable region (VH) and/or a light chain variable region (VL).

In some embodiments, the antibody or antigen binding fragment thereof of the present invention comprises the following heavy chain variable region (VH) and/or light chain variable region (VL), wherein CDR is defined according to the IMGT numbering system:

(a) the heavy chain variable region (VH) comprising the following 3 CDRs: CDR-H1 with the sequence as set forth in SEQ ID NO: 5, CDR-H2 with the sequence as set forth in SEQ ID NO: 6, and CDR-H3 with the sequence as set forth in SEQ ID NO: 7; and/or, the light chain variable region (VL) comprising the following 3 CDRs: CDR-L1 with the sequence as set forth in SEQ ID NO: 8, CDR-L2 with the sequence as set forth in SEQ ID NO: 9, and CDR-L3 with the sequence as set forth in SEQ ID NO: 10;

or (b) the heavy chain variable region (VH) comprising the following 3 CDRs: CDR-H1 with the sequence as set forth in SEQ ID NO: 11, CDR-H2 with the sequence as set forth in SEQ ID NO: 12 or 110, and CDR-H3 with the sequence as set forth in SEQ ID NO: 13; and/or, a light chain variable region (VL) comprising the following 3 CDRs: CDR-L1 with the sequence as set forth in SEQ ID NO: 14, CDR-L2 with the sequence as set forth in SEQ ID NO: 15, and CDR-L3 with the sequence as set forth in SEQ ID NO: 16;

or (c) the heavy chain variable region (VH) comprising the following 3 CDRs: CDR-H1 with the sequence as set forth in SEQ ID NO: 81, CDR-H2 with the sequence as set forth in SEQ ID NO: 82, and CDR-H3 with the sequence as set forth in SEQ ID NO: 83; and/or, a light chain variable region (VL) comprising the following 3 CDRs: CDR-L1 with the sequence as set forth in SEQ ID NO: 95, CDR-L2 with the sequence as set forth in SEQ ID NO: 96, and CDR-L3 with the sequence as set forth in SEQ ID NO: 97;

or (d) the heavy chain variable region (VH) comprising the following 3 CDRs: CDR-H1 with the sequence as set forth in SEQ ID NO: 81, CDR-H2 with the sequence as set forth in SEQ ID NO: 84, and CDR-H3 with the sequence as set forth in SEQ ID NO: 85; and/or, a light chain variable region (VL) comprising the following 3 CDRs: CDR-L1 with the sequence as set forth in SEQ ID NO: 95, CDR-L2 with the sequence as set forth in SEQ ID NO: 96, and CDR-L3 with the sequence as set forth in SEQ ID NO: 97;

or (e) the heavy chain variable region (VH) comprising the following 3 CDRs: CDR-H1 with the sequence as set forth in SEQ ID NO: 86, CDR-H2 with the sequence as set forth in SEQ ID NO: 87, and CDR-H3 with the sequence as set forth in SEQ ID NO: 88; and/or, a light chain variable region (VL) comprising the following 3 CDRs: CDR-L1 with the sequence as set forth in SEQ ID NO: 95, CDR-L2 with the sequence as set forth in SEQ ID NO: 98, and CDR-L3 with the sequence as set forth in SEQ ID NO: 99;

or (f) the heavy chain variable region (VH) comprising the following 3 CDRs: CDR-H1 with the sequence as set forth in SEQ ID NO: 89, CDR-H2 with the sequence as set forth in SEQ ID NO: 90, and CDR-H3 with the sequence as set forth in SEQ ID NO: 91; and/or, a light chain variable region (VL) comprising the following 3 CDRs: CDR-L1 with the sequence as set forth in SEQ ID NO: 95, CDR-L2 with the sequence as set forth in SEQ ID NO: 98, and CDR-L3 with the sequence as set forth in SEQ ID NO: 99;

or (g) the heavy chain variable region (VH) comprising the following 3 CDRs: CDR-H1 with the sequence as set forth in SEQ ID NO: 92, CDR-H2 with the sequence as set forth in SEQ ID NO: 93, and CDR-H3 with the sequence as set forth in SEQ ID NO: 94; and/or, a light chain variable region (VL) comprising the following 3 CDRs: CDR-L1 with the sequence as set forth in SEQ ID NO: 95, CDR-L2 with the sequence as set forth in SEQ ID NO: 100, and CDR-L3 with the sequence as set forth in SEQ ID NO: 101.

In some embodiments, the antibody or antigen binding fragment thereof of the present invention comprises the following heavy chain variable region (VH) and/or light chain variable region (VL), wherein CDR is defined according to the AbM numbering system:

(a) the heavy chain variable region (VH) comprising the following 3 CDRs: CDR-H1 with the sequence as set forth in SEQ ID NO:17, CDR-H2 with the sequence as set forth in SEQ ID NO: 18, and CDR-H3 with the sequence as set forth in SEQ ID NO: 19; and/or, a light chain variable region (VL) comprising the following 3 CDRs: CDR-L1 with the sequence as set forth in SEQ ID NO: 20, CDR-L2 with the sequence as set forth in SEQ ID NO: 21, and CDR-L3 with the sequence as set forth in SEQ ID NO: 22;

or (b) the heavy chain variable region (VH) comprising the following 3 CDRs: CDR-H1 with the sequence as set forth in SEQ ID NO:23, CDR-H2 with the sequence as set forth in SEQ ID NO: 24 or 111, and CDR-H3 with the sequence as set forth in SEQ ID NO: 25; and/or, a light chain variable region (VL) comprising the following 3 CDRs: CDR-L1 with the sequence as set forth in SEQ ID NO: 26, CDR-L2 with the sequence as set forth in SEQ ID NO: 27, and CDR-L3 with the sequence as set forth in SEQ ID NO: 28;

or (c) the heavy chain variable region (VH) comprising the following 3 CDRs: CDR-H1 with the sequence as set forth in SEQ ID NO:58, CDR-H2 with the sequence as set forth in SEQ ID NO: 62, and CDR-H3 with the sequence as set forth in SEQ ID NO: 67; and/or,
a light chain variable region (VL) comprising the following 3 CDRs: CDR-L1 with the sequence as set forth in SEQ ID NO:72, CDR-L2 with the sequence as set forth in SEQ ID NO: 74, and CDR-L3 with the sequence as set forth in SEQ ID NO: 78;
or
(d) the heavy chain variable region (VH) comprising the following 3 CDRs: CDR-H1 with the sequence as set forth in SEQ ID NO:58, CDR-H2 with the sequence as set forth in SEQ ID NO: 63, and CDR-H3 with the sequence as set forth in SEQ ID NO: 68; and/or,
a light chain variable region (VL) comprising the following 3 CDRs: CDR-L1 with the sequence as set forth in SEQ ID NO:72, CDR-L2 with the sequence as set forth in SEQ ID NO: 74, and CDR-L3 with the sequence as set forth in SEQ ID NO: 78;
or
(e) the heavy chain variable region (VH) comprising the following 3 CDRs: CDR-H1 with the sequence as set forth in SEQ ID NO:59, CDR-H2 with the sequence as set forth in SEQ ID NO: 64, and CDR-H3 with the sequence as set forth in SEQ ID NO: 69; and/or,
a light chain variable region (VL) comprising the following 3 CDRs: CDR-L1 with the sequence as set forth in SEQ ID NO:72, CDR-L2 with the sequence as set forth in SEQ ID NO: 75, and CDR-L3 with the sequence as set forth in SEQ ID NO: 79;
or
(f) the heavy chain variable region (VH) comprising the following 3 CDRs: CDR-H1 with the sequence as set forth in SEQ ID NO:60, CDR-H2 with the sequence as set forth in SEQ ID NO: 65, and CDR-H3 with the sequence as set forth in SEQ ID NO: 70; and/or,
a light chain variable region (VL) comprising the following 3 CDRs: CDR-L1 with the sequence as set forth in SEQ ID NO:72, CDR-L2 with the sequence as set forth in SEQ ID NO: 76, and CDR-L3 with the sequence as set forth in SEQ ID NO: 79;
or
(g) the heavy chain variable region (VH) comprising the following 3 CDRs: CDR-H1 with the sequence as set forth in SEQ ID NO:61, CDR-H2 with the sequence as set forth in SEQ ID NO: 66, and CDR-H3 with the sequence as set forth in SEQ ID NO: 71; and/or,
a light chain variable region (VL) comprising the following 3 CDRs: CDR-L1 with the sequence as set forth in SEQ ID NO:73, CDR-L2 with the sequence as set forth in SEQ ID NO: 77, and CDR-L3 with the sequence as set forth in SEQ ID NO: 80.

In some embodiments, an antibody or an antigen binding fragment thereof of the present invention comprises the following heavy chain variable region (VH) and/or a light chain variable region (VL), said VH and/or VL comprises at least one CDR with a mutation compared with any of the VH and/or VL of (a) to (g) defined according to IMGT, Chothia, Kabat or AbM numbering system, said mutation is a substitution, deletion, or addition of one or several amino acids (such as a substitution, deletion, or addition of 1, 2, or 3 amino acids); preferably, the substitution is a conservative substitution.

In some preferred embodiments, the VH of an antibody or antigen-binding fragment thereof of the invention includes framework regions (FR) of heavy chain variable region (VH) derived from a mouse immunoglobulin, and/or the VL of an antibody or antigen-binding fragment thereof includes framework regions (FR) of light chain variable region (VL) derived from a mouse immunoglobulin. Therefore, in certain preferable embodiments, an antibody or an antigen-binding fragment thereof of the invention is a mouse antibody.

In some preferred embodiments, the VH of an antibody or antigen-binding fragment thereof of the present invention includes framework regions (FR) of heavy chain variable region (VH) derived from a human immunoglobulin, and/or the VL of an antibody or antigen-binding fragment thereof includes framework regions (FR) of light chain variable region (VL) derived from a human immunoglobulin. Therefore, in certain preferable embodiments, an antibody or an antigen-binding fragment thereof of the invention is a humanized antibody. In these embodiments, the heavy chain variable region FR and/or the light chain variable region FR of an antibody or antigen-binding fragment thereof of the invention comprises one or more non-human (e.g., mouse) amino acid residues. For example, the heavy chain framework region FR and/or the light chain framework region FR comprises one or more amino acid back mutations, with corresponding mouse amino acid residues in these back mutations.

In some embodiments, an antibody or an antigen binding fragment thereof of the present invention comprises:

(a) a heavy chain FR of a human immunoglobulin or a variant thereof, wherein the variant has a conservative substitution of up to 20 amino acids (for example, a conservative substitution of up to 15, up to 10, or up to 5 amino acids; for example, a conservative substitution of 1, or 2, or 3, or 4, or 5 amino acids) compared with the germline antibody gene sequence from which it is derived; and/or (b) a light chain FR of a human immunoglobulin or a variant thereof, wherein the variant has a conservative substitution of up to 20 amino acids (for example, a conservative substitution of up to 15, up to 10, or up to 5 amino acids; for example, a conservative substitution of 1, or 2, or 3, or 4, or 5 amino acids) compared with the germline antibody gene sequence from which it is derived.

In some preferred embodiments, an antibody or an antigen-binding fragment of the present invention has a humanization degree of at least 75%, at least 80%, at least 85%, at least 90%, at least 91%, at least 92%, at least 93%, at least 94%, at least 95%, at least 96%, at least 97%, at least 98%, at least 99% or 100%.

In some preferred embodiments, an antibody or antigen binding fragment thereof of present invention comprises (a) a heavy chain variable region (VH), comprising an amino acid sequence selected from the following:

(i) any one of the sequences as set forth in SEQ ID NOs: 1, 29, 30, 31, 32; or (ii) a sequence comprising a substitution, deletion, or addition of one or several amino acids (e.g., a substitution, deletion, or addition of 1, 2, 3, 4, or 5 amino acids) compared with any one of the sequences as set forth in SEQ ID NOs: 1, 29, 30, 31, 32; or (iii) a sequence having at least 75%, at least 80%, at least 85%, at least 90%, at least 91%, at least 92%, at least 93%, at least 94%, at least 95%, at least 96%, at least 97%, at least 98%, at least 99% or 100% identity to any one of the sequences as set forth in SEQ ID NOs: 1, 29, 30, 31, 32;

and/or (b) a light chain variable region (VL), comprising an amino acid sequence selected from the following:

(iv) any one of the sequences as set forth in SEQ ID NOs: 2, 33, 34, 35, 36, 37, 38;

(v) a sequence comprising a substitution, deletion, or addition of one or several amino acids (e.g., a substitution, deletion, or addition of 1, 2, 3, 4, or 5 amino acids) compared with any one of the sequences as set forth in SEQ ID NOs: 2, 33, 34, 35, 36, 37, 38; or (vi) a sequence having at least 75%, at least 80%, at least 85%, at least 90%, at least 91%, at least 92%, at least 93%, at least 94%, at least 95%, at least 96%, at least 97%, at least 98%, at least 99% or 100% identity to any one of the sequences as set forth in SEQ ID NOs: 2, 33, 34, 35, 36, 37, 38.

In some embodiments, an antibody or antigen binding fragment thereof of present invention comprises:

(a) a heavy chain variable region (VH), comprising an amino acid sequence selected from the following:

(i) any one of the sequences as set forth in SEQ ID NOs: 3, 39, 40;

(ii) a sequence comprising a substitution, deletion, or addition of one or several amino acids (e.g., a substitution, deletion, or addition of 1, 2, 3, 4, or 5 amino acids) compared with any one of the sequences as set forth in SEQ ID NOs: 3, 39, 40; or (iii) a sequence having at least 75%, at least 80%, at least 85%, at least 90%, at least 91%, at least 92%, at least 93%, at least 94%, at least 95%, at least 96%, at least 97%, at least 98%, at least 99% or 100% identity to any one of the sequences as set forth in SEQ ID NOs: 3, 39, 40;

and/or (b) a light chain variable region (VL), comprising an amino acid sequence selected from the following:

(iv) one of the sequences as set forth in SEQ ID NOs: 4, 41;

(v) a sequence comprising a substitution, deletion, or addition of one or several amino acids (e.g., a substitution, deletion, or addition of 1, 2, 3, 4, or 5 amino acids) compared with any one of the sequences as set forth in SEQ ID NOs: 4, 41; or (vi) a sequence having at least 75%, at least 80%, at least 85%, at least 90%, at least 91%, at least 92%, at least 93%, at least 94%, at least 95%, at least 96%, at least 97%, at least 98%, at least 99% or 100% identity to any one of the sequences as set forth in SEQ ID NOs: 4, 41.

In some embodiments, an antibody or an antigen binding fragment thereof of the present invention comprises the following heavy chain variable region (VH) and/or a light chain variable region (VL): a VH sequence shown in any one of SEQ ID NOs: 1, 29, 30, 31, 32; and/or, a VL sequence shown in any one of SEQ ID NOs: 2, 33, 34, 35, 36, 37, 38.

In some embodiments, an antibody or an antigen binding fragment thereof of the present invention comprises the following heavy chain variable region (VH) and/or a light chain variable region (VL): a VH sequence shown in any one of SEQ ID NOs: 3, 39, 40; and/or, a VL sequence shown in any one of SEQ ID NOs: 4, 41.

In some preferred embodiments, an antibody or an antigen binding fragment thereof of the present invention comprises a VH having the sequence of SEQ ID NO: 44 and/or a VL having the sequence of SEQ ID NO: 45.

In some embodiments, the VH and/or VL of the antibody or an antigen-binding fragment thereof has at least 70%, at least 80%, at least 85%, at least 90%, at least 91%, at least 92%, at least 93%, at least 94%, at least 95%, at least 96%, at least 97%, at least 98%, at least 99% or 100% identity to the VH sequence of SEQ ID NO: 44, and/or the VL sequence of SEQ ID NO: 45.

In some embodiments, the VH and/or VL of the antibody or an antigen-binding fragment thereof has a substitution, deletion, or addition of one or several amino acids (e.g., a substitution, deletion, or addition of 1, 2, 3, 4, or 5 amino acids) compared with the VH sequence of SEQ ID NO: 44, and/or the VL sequence of SEQ ID NO: 45. In preferred embodiments, the substitution is a conservative substitution.

In some preferred embodiments, an antibody or an antigen binding fragment thereof of the present invention comprises a VH having the sequence of SEQ ID NO: 46 and/or a VL having the sequence of SEQ ID NO 47.

In some embodiments, the VH and/or VL of the antibody or an antigen-binding fragment thereof has at least 70%, at least 80%, at least 85%, at least 90%, at least 91%, at least 92%, at least 93%, at least 94%, at least 95%, at least 96%, at least 97%, at least 98%, at least 99% or 100% identity to the VH sequence of SEQ ID NO: 46 and/or the VL sequence of SEQ ID NO: 47.

In some embodiments, the VH and/or VL of the antibody or an antigen-binding fragment thereof has a substitution, deletion, or addition of one or several amino acids (e.g., a substitution, deletion, or addition of 1, 2, 3, 4, or 5 amino acids) compared with the VH sequence of SEQ ID NO: 46 and/or the VL sequence of SEQ ID NO: 47. In preferred embodiments, the substitution is a conservative substitution.

In some preferred embodiments, an antibody or an antigen binding fragment thereof of the present invention comprises a VH having the sequence of SEQ ID NO: 48 and/or a VL having the sequence of SEQ ID NO: 49.

In some embodiments, the VH and/or VL of the antibody or an antigen-binding fragment thereof has at least 70%, at least 80%, at least 85%, at least 90%, at least 91%, at least 92%, at least 93%, at least 94%, at least 95%, at least 96%, at least 97%, at least 98%, at least 99% or 100% identity to the VH sequence of SEQ ID NO: 48 and/or the VL sequence of SEQ ID NO: 49.

In some embodiments, the VH and/or VL of the antibody or an antigen-binding fragment thereof has a substitution, deletion, or addition of one or several amino acids (e.g., a substitution, deletion, or addition of 1, 2, 3, 4, or 5 amino acids) compared with the VH sequence of SEQ ID NO: 48 and/or the VL sequence of SEQ ID NO: 49. In preferred embodiments, the substitution is a conservative substitution.

In some preferred embodiments, an antibody or an antigen binding fragment thereof of the present invention comprises a VH having the sequence of SEQ ID NO: 50 and/or a VL having the sequence of SEQ ID NO:51.

In some embodiments, the VH and/or VL of the antibody or an antigen-binding fragment thereof has at least 70%, at least 80%, at least 85%, at least 90%, at least 91%, at least 92%, at least 93%, at least 94%, at least 95%, at least 96%, at least 97%, at least 98%, at least 99% or 100% identity to the VH sequence of SEQ ID NO: 50 and/or the VL sequence of SEQ ID NO: 51.

In some embodiments, the VH and/or VL of the antibody or an antigen-binding fragment thereof has a substitution, deletion, or addition of one or several amino acids (e.g., a substitution, deletion, or addition of 1, 2, 3, 4, or 5 amino acids) compared with the VH sequence of SEQ ID NO: 50 and/or the VL sequence of SEQ ID NO:51. In preferred embodiments, the substitution is a conservative substitution.

In some preferred embodiments, an antibody or an antigen binding fragment thereof of the present invention comprises a VH having the sequence of SEQ ID NO: 52 and/or a VL having the sequence of SEQ ID NO: 53.

In some embodiments, the VH and/or VL of the antibody or an antigen-binding fragment thereof has at least 70%, at least 80%, at least 85%, at least 90%, at least 91%, at least 92%, at least 93%, at least 94%, at least 95%, at least 96%, at least 97%, at least 98%, at least 99% or 100% identity to the VH sequence of SEQ ID NO: 52 and/or the VL sequence of SEQ ID NO: 53.

In some embodiments, the VH and/or VL of the antibody or an antigen-binding fragment thereof has a substitution, deletion, or addition of one or several amino acids (e.g., a substitution, deletion, or addition of 1, 2, 3, 4, or 5 amino acids) compared with the VH sequence of SEQ ID NO: 52 and/or the VL sequence of SEQ ID NO: 53. In preferred embodiments, the substitution is a conservative substitution.

In some embodiments, an antibody or an antigen-binding fragment thereof of the present invention comprises:
(a) a VH having the sequence of SEQ ID NO: 1 and a VL having the sequence of SEQ ID NO: 2;
(b) a VH having the sequence of SEQ ID NO: 29 and a VL having the sequence of SEQ ID NO: 33;
(c) a VH having the sequence of SEQ ID NO: 29 and a VL having the sequence of SEQ ID NO: 34;
(d) a VH having the sequence of SEQ ID NO: 29 and a VL having the sequence of SEQ ID NO: 35;
(e) a VH having the sequence of SEQ ID NO: 29 and a VL having the sequence of SEQ ID NO: 36;
(f) a VH having the sequence of SEQ ID NO: 29 and a VL having the sequence of SEQ ID NO: 37;
(g) a VH having the sequence of SEQ ID NO: 29 and a VL having the sequence of SEQ ID NO: 38;
(h) a VH having the sequence of SEQ ID NO: 30 and a VL having the sequence of SEQ ID NO: 33;
(i) a VH having the sequence of SEQ ID NO: 31 and a VL having the sequence of SEQ ID NO: 33;
(j) a VH having the sequence of SEQ ID NO: 32 and a VL having the sequence of SEQ ID NO: 33;
(k) a VH having the sequence of SEQ ID NO: 3 and a VL having the sequence of SEQ ID NO: 4;
(l) a VH having the sequence of SEQ ID NO: 39 and a VL having the sequence of SEQ ID NO: 41;
(m) a VH having the sequence of SEQ ID NO: 40 and a VL having the sequence of SEQ ID NO: 41;
(n) a VH having the sequence of SEQ ID NO: 44 and a VL having the sequence of SEQ ID NO: 45;
(o) a VH having the sequence of SEQ ID NO: 46 and a VL having the sequence of SEQ ID NO: 47;
(p) a VH having the sequence of SEQ ID NO: 48 and a VL having the sequence of SEQ ID NO: 49;
(q) a VH having the sequence of SEQ ID NO: 50 and a VL having the sequence of SEQ ID NO: 51;
(r) a VH having the sequence of SEQ ID NO: 52 and a VL having the sequence of SEQ ID NO: 53.

In some preferred embodiments, the heavy chain variable region (VH) has at least 70%, at least 80%, at least 85%, at least 90%, at least 91%, at least 92%, at least 93%, at least 94%, at least 95%, at least 96%, at least 97%, at least 98%, at least 99% or 100% identity to the VH in any of (a) to (r); and/or, the light chain variable region (VL) has at least 70%, at least 80%, at least 85%, at least 90%, at least 91%, at least 92%, at least 93%, at least 94%, at least 95%, at least 96%, at least 97%, at least 98%, at least 99% or 100% identity to the VL in any of (a) to (r).

In some preferred embodiments, the heavy chain variable region (VH) comprises a substitution, deletion, or addition of one or several amino acids (e.g., a substitution, deletion, or addition of 1, 2, 3, 4, 5 amino acids) compared with the VH in any of (a) to (r); and/or, the light chain variable region (VL) comprises a substitution, deletion, or addition of one or several amino acids (e.g., a substitution, deletion, or addition of 1, 2, 3, 4, 5 amino acids) compared with the VL in any of (a) to (r); Preferably, the substitution is a conservative substitution.

In any respect of the above, an antibody or antigen-binding fragment thereof of the present invention can comprise a constant region sequence derived from mammal (e.g., mouse or human) immunoglobulin or a variant thereof. In some embodiments, the heavy chain of the antibody or antigen-binding fragment thereof of the present invention comprises the heavy chain constant region (CH) of a human or murine immunoglobulin or a variant thereof, wherein said variant comprises a substitution, deletion, or addition of one or several amino acids (e.g., a substitution, deletion, or addition of up to 20, up to 15, up to 10, or up to 5 amino acids; e.g., a substitution, deletion, or addition of 1, 2, 3, 4, or 5 amino acids) compared with the wild type sequence from which it is derived; and/or, the light chain of the antibody or antigen-binding fragment thereof of the present invention comprises a light chain constant region (CL) derived from a human or mouse immunoglobulin or a variant thereof, wherein said variant comprises a substitution, deletion, or addition of one or several amino acids (e.g., a substitution, deletion, or addition of up to 20, up to 15, up to 10, or up to 5 amino acids; e.g., a substitution, deletion, or addition of 1, 2, 3, 4, or 5 amino acids) compared with the wild type sequence from which it is derived.

In some preferred embodiments, an antibody or antigen-binding fragment thereof of the present invention comprises a heavy chain constant region (CH) derived from human immunoglobulin or a variant thereof, wherein said variant comprises a conservative substitution of up to 20 amino acids (e.g., a conservative substitution of up to 15, up to 10, or up to 5 amino acids; e.g., a conservative substitution of 1, 2, 3, 4, or 5 amino acids) compared with the wild type sequence from which it is derived; and/or, an antibody or antigen-binding fragment thereof of the present invention comprises a light chain constant region (CL) derived from human immunoglobulin or a variant thereof, wherein said variant comprises a conservative substitution of up to 20 amino acids (e.g., a conservative substitution of up to 15, up to 10, or up to 5 amino acids; e.g., a conservative substitution of 1, 2, 3, 4, or 5 amino acids) compared with the wild type sequence from which it is derived.

In some embodiments, an antibody or antigen-binding fragment thereof of the present invention comprises a heavy chain constant region (CH) derived from mouse immunoglobulin or a variant thereof, wherein said variant comprises a conservative substitution of up to 20 amino acids (e.g., a conservative substitution of up to 15, up to 10, or up to 5 amino acids; e.g., a conservative substitution of 1, 2, 3, 4, or 5 amino acids) compared with the wild type sequence from which it is derived; and/or, an antibody or antigen-binding fragment thereof of the present invention comprises a light chain constant region (CL) derived from mouse immunoglobulin or a variant thereof, wherein said variant comprises a conservative substitution of up to 20 amino acids (e.g., a conservative substitution of up to 15, up to 10, or up to 5 amino acids; e.g., a conservative substitution of 1, 2, 3, 4, or 5 amino acids) compared with the wild type sequence from which it is derived.

In some embodiments, the constant region is altered, e.g., mutated, to modify the properties of the anti-CLDN18.2 antibody (e.g., to alter one or more of the following properties: binding of Fc receptor, antibody glycosylation, amount of cysteine residues, functions on effector cells or complements). At least one amino acid residue in the constant region of antibody can be replaced with other ones to alter the function. For example, effector function can be altered (e.g., enhanced) by altering the antibody affinity to an effector ligand (such as FcR or C1q). The Fc region of an antibody mediates key effector functions, such as ADCC, Phagocytosis, CDC, etc. In some situations, these effector functions are necessary for a therapeutic antibody.

In some embodiments, the anti-CLDN18.2 antibody or antigen-binding fragment thereof of present invention comprises a heavy chain constant region (Fc), which can be selected from, for example the heavy chain constant region of IgG1, IgG2, IgG3, IgG4, IgM, IgA1, IgA2, IgD and IgE; preferably, selected from the heavy chain constant region of IgG1, IgG2, IgG3 or IgG4, more preferably, selected from the heavy chain constant region of IgG1 or IgG4 (for example, human IgG1 or IgG4). In some embodiments, the anti-CLDN18.2 antibody molecule has a light chain constant region, which can be selected from a light chain constant region of kappa or lambda, preferably a kappa light chain constant region (e.g., a human kappa light chain).

In some embodiments, an antibody or antigen-binding fragment thereof of present invention comprising a heavy chain constant region (CH) selected from the group consisting of:
(1) human IgG1 heavy chain constant region; or
(2) human IgG4 heavy chain constant region.

In some preferred embodiments, an antibody or antigen binding fragment thereof of present invention comprises:
(a) a heavy chain constant region (CH), comprising an amino acid sequence selected from the group consisting of:
(i) a sequence as set forth in SEQ ID NO: 42;
(ii) a sequence having a substitution, deletion, or addition of one or several amino acids (e.g., a substitution, deletion, or addition of 1, 2, 3, 4, or 5 amino acids) compared with the sequence as set forth in SEQ ID NO: 42; or
(iii) a sequence having at least 80%, at least 85%, at least 90%, at least 91%, at least 92%, at least 93%, at least 94%, at least 95%, at least 96%, at least 97%, at least 98%, at least 99% or 100% identity to the sequence as set forth in SEQ ID NO:42;
and/or
(b) a light chain constant region (CL), comprising an amino acid sequence selected from the group consisting of:
(iv) a sequence as set forth in SEQ ID NO: 43;
(v) a sequence having a substitution, deletion, or addition of one or several amino acids (e.g., a substitution, deletion, or addition of 1, 2, 3, 4, or 5 amino acids) compared with the sequence as set forth in SEQ ID NO: 43; or
(vi) a sequence having at least 80%, at least 85%, at least 90%, at least 91%, at least 92%, at least 93%, at least 94%, at least 95%, at least 96%, at least 97%, at least 98%, at least 99% or 100% identity to the sequence as set forth in SEQ ID NO:43.

In some preferred embodiments, the substitution in (ii) or (v) is a conservative substitution.

In some preferred embodiments, an antibody or antigen-binding fragment thereof of the invention comprising a CH having a sequence as set forth in SEQ ID NO: 42, and a CL having a sequence as set forth in SEQ ID NO: 43.

In some preferred embodiments, an antibody of present invention comprises a heavy chain comprising a VH having the amino acid sequence of SEQ ID NO: 1 and a CH having the amino acid sequence of SEQ ID NO: 42, and a light chain comprising a VL having the amino acid sequence of SEQ ID NO: 2 and a CL having the amino acid sequence of SEQ ID NO: 43.

In some preferred embodiments, an antibody of present invention comprises a heavy chain comprising a VH having the amino acid sequence of SEQ ID NO: 29 and a CH having the amino acid sequence of SEQ ID NO: 42, and a light chain comprising a VL having the amino acid sequence of SEQ ID NO: 33 and a CL having the amino acid sequence of SEQ ID NO: 43.

In some preferred embodiments, an antibody of present invention comprises a heavy chain comprising a VH having the amino acid sequence of SEQ ID NO: 29 and a CH having the amino acid sequence of SEQ ID NO: 42, and a light chain comprising a VL having the amino acid sequence of SEQ ID NO: 34 and a CL having the amino acid sequence of SEQ ID NO: 43.

In some preferred embodiments, an antibody of present invention comprises a heavy chain comprising a VH having the amino acid sequence of SEQ ID NO: 29 and a CH having the amino acid sequence of SEQ ID NO: 42, and a light chain comprising a VL having the amino acid sequence of SEQ ID NO: 35 and a CL having the amino acid sequence of SEQ ID NO: 43.

In some preferred embodiments, an antibody of present invention comprises a heavy chain comprising a VH having the amino acid sequence of SEQ ID NO: 29 and a CH having the amino acid sequence of SEQ ID NO: 42, and a light chain comprising a VL having the amino acid sequence of SEQ ID NO: 36 and a CL having the amino acid sequence of SEQ ID NO: 43.

In some preferred embodiments, an antibody of present invention comprises a heavy chain comprising a VH having the amino acid sequence of SEQ ID NO: 29 and a CH having the amino acid sequence of SEQ ID NO: 42, and a light chain comprising a VL having the amino acid sequence of SEQ ID NO: 37 and a CL having the amino acid sequence of SEQ ID NO: 43.

In some preferred embodiments, an antibody of present invention comprises a heavy chain comprising a VH having the amino acid sequence of SEQ ID NO: 29 and a CH having the amino acid sequence of SEQ ID NO: 42, and a light chain comprising a VL having the amino acid sequence of SEQ ID NO: 38 and a CL having the amino acid sequence of SEQ ID NO: 43.

In some preferred embodiments, an antibody of present invention comprises a heavy chain comprising a VH having the amino acid sequence of SEQ ID NO: 30 and a CH having the amino acid sequence of SEQ ID NO: 42, and a light chain comprising a VL having the amino acid sequence of SEQ ID NO: 33 and a CL having the amino acid sequence of SEQ ID NO: 43.

In some preferred embodiments, an antibody of present invention comprises a heavy chain comprising a VH having the amino acid sequence of SEQ ID NO: 31 and a CH having the amino acid sequence of SEQ ID NO: 42, and a light chain comprising a VL having the amino acid sequence of SEQ ID NO: 33 and a CL having the amino acid sequence of SEQ ID NO: 43.

In some preferred embodiments, an antibody of present invention comprises a heavy chain comprising a VH having the amino acid sequence of SEQ ID NO: 32 and a CH having the amino acid sequence of SEQ ID NO: 42, and a light chain comprising a VL having the amino acid sequence of SEQ ID NO: 33 and a CL having the amino acid sequence of SEQ ID NO: 43.

In some preferred embodiments, an antibody of present invention comprises a heavy chain comprising a VH having the amino acid sequence of SEQ ID NO: 3 and a CH having the amino acid sequence of SEQ ID NO: 42, and a light chain comprising a VL having the amino acid sequence of SEQ ID NO: 4 and a CL having the amino acid sequence of SEQ ID NO: 43.

In some preferred embodiments, an antibody of present invention comprises a heavy chain comprising a VH having the amino acid sequence of SEQ ID NO: 39 and a CH having the amino acid sequence of SEQ ID NO: 42, and a light chain comprising a VL having the amino acid sequence of SEQ ID NO: 41 and a CL having the amino acid sequence of SEQ ID NO: 43.

In some preferred embodiments, an antibody of present invention comprises a heavy chain comprising a VH having the amino acid sequence of SEQ ID NO: 40 and a CH having the amino acid sequence of SEQ ID NO: 42, and a light chain comprising a VL having the amino acid sequence of SEQ ID NO: 41 and a CL having the amino acid sequence of SEQ ID NO: 43.

In some preferred embodiments, an antibody of present invention comprises a heavy chain comprising a VH having the amino acid sequence of SEQ ID NO: 44 and a CH having the amino acid sequence of SEQ ID NO: 42, and a light chain comprising a VL having the amino acid sequence of SEQ ID NO: 45 and a CL having the amino acid sequence of SEQ ID NO: 43.

In some preferred embodiments, an antibody of present invention comprises a heavy chain comprising a VH having the amino acid sequence of SEQ ID NO: 46 and a CH having the amino acid sequence of SEQ ID NO: 42, and a light chain comprising a VL having the amino acid sequence of SEQ ID NO: 47 and a CL having the amino acid sequence of SEQ ID NO: 43.

In some preferred embodiments, an antibody of present invention comprises a heavy chain comprising a VH having the amino acid sequence of SEQ ID NO: 48 and a CH having the amino acid sequence of SEQ ID NO: 42, and a light chain comprising a VL having the amino acid sequence of SEQ ID NO: 49 and a CL having the amino acid sequence of SEQ ID NO: 43.

In some preferred embodiments, an antibody of present invention comprises a heavy chain comprising a VH having the amino acid sequence of SEQ ID NO: 50 and a CH having the amino acid sequence of SEQ ID NO: 42, and a light chain comprising a VL having the amino acid sequence of SEQ ID NO: 51 and a CL having the amino acid sequence of SEQ ID NO: 43.

In some preferred embodiments, an antibody of present invention comprises a heavy chain comprises a VH having the amino acid sequence of SEQ ID NO: 52 and a CH having the amino acid sequence of SEQ ID NO: 42, and a light chain comprising a VL having the amino acid sequence of SEQ ID NO: 53 and a CL having the amino acid sequence of SEQ ID NO: 43.

In some preferred embodiments, an antibody or antigen binding fragment thereof of present invention comprises
(a) a heavy chain, comprising an amino acid sequence selected from the group consisting of:
    (i) a sequence as set forth in SEQ ID NO: 102;
    (ii) a sequence having a substitution, deletion, or addition of one or several amino acids (e.g., a substitution, deletion, or addition of 1, 2, 3, 4, or 5 amino acids) compared with SEQ ID NO: 102; or
    (iii) a sequence having at least 80%, at least 85%, at least 90%, at least 91%, at least 92%, at least 93%, at least 94%, at least 95%, at least 96%, at least 97%, at least 98%, at least 99% or 100% identity to SEQ ID NO: 102;
    and
(b) a light chain, comprising an amino acid sequence selected from the group consisting of:
    (iv) a sequence as set forth in SEQ ID NO: 103;
    (v) a sequence having a substitution, deletion, or addition of one or several amino acids (e.g., a substitution, deletion, or addition of 1, 2, 3, 4, or 5 amino acids) compared with SEQ ID NO: 103; or
    (vi) a sequence having at least 80%, at least 85%, at least 90%, at least 91%, at least 92%, at least 93%, at least 94%, at least 95%, at least 96%, at least 97%, at least 98%, at least 99% or 100% identity to SEQ ID NO: 103.

In some preferred embodiments, the substitution in (ii) or (v) is a conservative substitution.

In some preferred embodiments, an antibody or antigen binding fragment thereof of present invention comprises
(a) a heavy chain, comprising an amino acid sequence selected from the group consisting of:
    (i) a sequence as set forth in SEQ ID NO: 106;
    (ii) a sequence having a substitution, deletion, or addition of one or several amino acids (e.g., a substitution, deletion, or addition of 1, 2, 3, 4, or 5 amino acids) compared with SEQ ID NO: 106; or
    (iii) a sequence having at least 80%, at least 85%, at least 90%, at least 91%, at least 92%, at least 93%, at least 94%, at least 95%, at least 96%, at least 97%, at least 98%, at least 99% or 100% identity to SEQ ID NO: 106;
    and
(b) a light chain, comprising an amino acid sequence selected from the group consisting of:
    (iv) a sequence as set forth in SEQ ID NO: 107;
    (v) a sequence having a substitution, deletion, or addition of one or several amino acids (e.g., a substitution, deletion, or addition of 1, 2, 3, 4, or 5 amino acids) compared with SEQ ID NO: 107; or
    (vi) a sequence having at least 80%, at least 85%, at least 90%, at least 91%, at least 92%, at least 93%, at least 94%, at least 95%, at least 96%, at least 97%, at least 98%, at least 99% or 100% identity to SEQ ID NO: 107.

In some preferred embodiments, the substitution in (ii) or (v) is a conservative substitution.

In some preferred embodiments, an antibody or antigen binding fragment thereof of present invention comprises a heavy chain of SEQ ID NO:102 and a light chain of SEQ ID NO:103.

In some preferred embodiments, an antibody or antigen binding fragment thereof of present invention comprises a heavy chain of SEQ ID NO:106 and a light chain of SEQ ID NO:107.

In some preferred embodiments, an antibody of present invention is a chimeric or humanized antibody. In some preferred embodiment, an antibody or antigen-binding fragment thereof of the invention is selected from scFv, Fab, Fab', (Fab')$_2$, Fv fragment, disulfide-linked Fv (dsFv), diabody, bispecific antibodies, and multi-specificity antibodies.

In some embodiments, an antibody or antigen binding fragment thereof of the invention has at least one of the following characteristics:
(a) binding to CLDN18.2 (for example human CLDN18.2) with a KD value less than about 100 nM, for example, less than about 10 nM, 1 nM, 0.1 nM, or less. For example, the KD value is determined by Bio-Layer Interferometry (BLI) (for example, ForteBio Octet®);
(b) binding to CLDN18.2 (for example human CLDN18.2) with a EC50 value less than about 500 nM, for example, less than about 100 nM, 10 nM, 1 nM, 0.9 nM, 0.8 nM, 0.7 nM, 0.6 nM, 0.5 nM, 0.4 nM, 0.3 nM, 0.2 nM, 0.1 nM, or less; for example, the EC50 value is determined by flow cytometry or a competitive ELISA technique;
(c) the antibody or antigen-binding fragment does not bind to CLDN18.1 (e.g., human CLDN18.1).

In some embodiments, the antibody or antigen binding fragment thereof has ADCC activity.

In some embodiments, the antibody or antigen binding fragment thereof has CDC activity.

In some preferred embodiments, the antibody or antigen binding fragment thereof has ADCC activity and CDC activity.

In some preferred embodiments, the antibody or antigen binding fragment thereof has enhanced ADCC activity and/or CDC activity.

In some preferred embodiments, an antibody or antigen binding fragment thereof of the invention has at least one of the following biological functions:
(a) inducing apoptosis in tumor cells;
(b) inhibiting tumor cell proliferation;
(c) increasing immune cell activity in vitro or in a subject (e.g., human);
(d) enhancing immune response in a subject (e.g., human);
(e) treating tumor in a subject (e.g., human);
(f) inducing and/or increasing T cell infiltration;
(g) inducing and/or enhancing immune reaction;
(h) inducing and/or increasing complement dependent cytotoxicity;
(i) inducing and/or increasing antibody-dependent cytotoxicity;
(j) increasing NK cell activity;
(k) inhibiting the expression and activation of CLDN18.2; or
(l) inhibiting CLDN18.2-mediated cell signaling pathway.

In some preferred embodiments, an antibody or antigen binding fragment thereof of present invention has a biological function of any combination of (a) to (l).

Antibody Derivatives

An antibody or antigen-binding fragment thereof of the invention can be derivatized, for example, linked to another molecule (e.g., another polypeptide or protein). In general, derivatization (e.g., labeling) of an antibody or antigen-binding fragment thereof does not adversely affect its binding to CLDN 18.2 (particularly human CLDN18.2). Thus, an antibody or antigen-binding fragment thereof of the invention is also intended to include such derivatized forms. For example, an antibody or antigen-binding fragment thereof of the invention can be functionally linked (by chemical coupling, gene fusion, non-covalent attachment or other manners) to one or more other molecular groups, such as another antibody (e.g., to form a bispecific antibody), a detection reagent, a pharmaceutical agent, and/or a protein or polypeptide (e.g., an avidin or a poly-histidine tag) which mediates binding of an antibody or antigen-binding fragment herein to bind to another molecule.

One type of derivatized antibody (e.g., a bispecific antibody) is produced by cross-linking two or more antibodies (of the same type or different types). Methods for obtaining bispecific antibodies are well known in the art, and examples thereof include, but are not limited to, chemical cross-linking, cell engineering (hybrid hybridoma) or genetic engineering.

Another type of derivatized antibody is a labeled antibody. For example, an antibody or antigen-binding fragment thereof herein of the invention is ligated to a detectable label. The detectable label of the present invention can be any substance detectable by fluorescence, spectroscopic, photochemical, biochemical, immunological, electrical, optical or chemical means. Such labels are well known in the art, examples of which include, but are not limited to, enzymes (e.g., horseradish peroxidase, alkaline phosphatase, beta-galactosidase, urease, glucose oxidase, etc.), radionuclides (e.g., 3H, 125I, 35S, 14C or 32P), fluorescent dyes (e.g., fluorescein isothiocyanate (FITC), fluorescein, tetramethylrhodamine isothiocyanate (TRITC), phycoerythrin (PE), Texas Red, Rhodamine, quantum dot or cyanine dye derivatives (e.g., Cy7, Alexa 750), acridinium esters, magnetic beads (e.g., Dynabeads®), calorimetric labels such as colloids Gold or tinted glass or plastic (e.g., polystyrene, polypropylene, latex, etc.) beads, and biotin for binding to the above-described label modified avidin (e.g., streptavidin). Patents that teach the use of such markers include, but are not limited to, U.S. Pat. Nos. 3,817,837; 3,850,752; 3,939,350; 3,996,345; 4,277,437; 4,275,149, and 4,366,241 (each incorporated herein by references). The detectable label as described above can be detected by methods known in the art. For example, the radioactive label can be detected using a photographic film or a scintillation counter, and the fluorescent label can be detected using a photodetector to detect the emitted light. Enzyme labels are typically detected by providing a substrate for the enzyme and detecting the reaction product produced by the action of the enzyme on the substrate, and the thermo-label is detected by simply visualizing the stained label. In certain embodiments, such markers can be adapted for use in immunological assays (e.g., enzyme-linked immunoassays, radio-immunoassays, fluorescent immunoassays, chemiluminescent immunoassays, etc.). In some embodiments, a detectable label as described above can be linked to an antibody or antigen-binding fragment thereof of the invention by a linker of varying length to reduce potential steric hindrance.

The antibodies or antigen-binding fragments thereof of the invention may also be derivatized with a chemical group, such as polyethylene glycol (PEG), methyl or ethyl, or a glycosyl group. These groups can be used to improve the biological properties of the antibody, such as increasing serum half-life.

As an example of the antibody derivatives, the present invention provides a conjugate comprising the monoclonal antibody or antigen-binding fragment thereof herein and a coupling moiety selected from: a detectable label, a radio-isotope, fluorescent substances, luminescent substances, colored substances, enzymes, polyethylene glycol (PEG), nuclides, nucleic acids, small molecule toxins, polypeptides having binding activities, proteins, receptors, ligands, and other active substance that inhibits tumor cell growth or promotes apoptosis or necrosis of tumor cells.

As an example of the antibody derivatives, the present invention provides a chimeric antigen receptor containing the monoclonal antibody or antigen binding fragment disclosed herein. In some preferred embodiments, the chimeric antigen receptor comprises a monoclonal antibody or antigen-binding fragment thereof herein (e.g., a scFv antibody), a transmembrane domain, and one or more intracellular T cell signaling domains. The present invention also provides host cells, for example immune cells (e.g., T lymphocytes, NK cells), that contain or express the chimeric antigen receptor.

As an example of the antibody derivatives, the present invention provides a multi-specific antibody which is formed by coupling a first antibody or fragments with other antibodies or fragments or antibody analogs thereof. Each antibody or fragment or antibody analog thereof retains the original binding specificity, and the first antibody or fragment thereof is an antibody or antigen-binding fragment thereof of the present invention; preferably, the multi-specific antibody is a bispecific antibody or a tri-specific antibody or tetra-specific antibodies.

Preparation of an Antibody

An antibody disclosed herein can be prepared by a variety of methods known in the art, such as by gene recombination engineering techniques. For example, a DNA molecule encoding a heavy chain or a light chain gene of an antibody of the present invention is obtained by chemical synthesis or PCR amplification. The resulting DNA molecule is inserted into an expression vector and then transfected into a host cell. The transfected host cells are then cultured under specific conditions and the antibodies of the invention are expressed.

The antigen-binding fragment of the present invention can be obtained by hydrolyzing intact antibody molecules (see Morimoto et al., J. Biochem. Biophys. Methods 24: 107-117 (1992) and Brennan et al., Science 229: 81 (1985)). In addition, these antigen-binding fragment also can be produced directly by recombinant host cells (reviewed in Hudson, Curr. Opin. Immunol. 11: 548-557 (1999); Little et al., Immunol. Today, 21: 364-370 (2000)). For example, Fab' fragments can be directly obtained from host cells, and Fab' fragments can be chemically coupled to form F(ab')$_2$ fragments (Carter et al., Bio/Technology, 10: 163-167 (1992)). Moreover, Fv, Fab or F(ab')$_2$ fragment can also be directly isolated from the recombinant host cell culture medium. Other techniques for preparing these antigen-binding fragments are well known to those of ordinary skill in the art.

Accordingly, in another aspect, the present invention provides an isolated nucleic acid molecule comprising a nucleotide sequence encoding an antibody or antigen-binding fragment thereof, or a heavy chain variable region and/or a light chain variable region, disclosed herein. According to codon degeneracy in the art, in some embodiments, the nucleotide sequence is replaceable according to codon degeneracy. In some embodiments, the nucleotide sequence is codon optimized.

In some preferred embodiments, the isolated nucleic acid molecule comprises a first nucleic acid and a second nucleic acid encoding a heavy chain variable region and a light chain variable region of an antibody or antigen-binding fragment thereof of the invention respectively, or comprises a first nucleic acid encoding the variable region and constant region of a heavy chain of an antibody or antigen-binding fragment thereof of the present disclosure and a second nucleic acid encoding the variable region and constant region of a light chain of the antibody or antigen-binding fragment thereof of the present disclosure, or comprises a first nucleic acid and a second nucleic acid encoding the heavy and light chain of the antibody or antigen-binding fragment thereof the present disclosure respectively, or comprises a sequence substantially identical to the aforementioned first nucleic acid and the second nucleic acid; wherein the antibody is selected from any one of the group consisting of: 1E9.2, 19H11.6, 16A9.11, 9C8.1, 6B9.22, 19G10.14, 2C6.9, 1E9.2hz11, 1E9.2hz12, 1E9.2hz13, 1E9.2hz14, 1E9.2hz15, 1E9.2hz17, 1E9.2hz21, 1E9.2hz31, 1E9.2hz41, 2C6.9hz11, and 2C6.9hz21; or comprises sequences substantially identical to the first and second nucleic acids. For example, the isolated nucleic acid molecule may comprise: the nucleotide sequences set forth in SEQ ID NO: 54, SEQ ID NO:55, SEQ ID NO:56, SEQ ID NO:57, SEQ ID NO: 104, SEQ ID NO: 105, SEQ ID NO: 108, SEQ ID NO: 109; or, a sequence substantially identical thereto (e.g., a sequence having at least about 85%, 90%, 95%, 99% or more identity to the aforementioned sequences or a sequence having one or several nucleotide substitutions, or a sequence that differs from the aforementioned sequence no more than 3, 6, 15, 30 or 45 nucleotides).

In some preferred embodiments, the present invention provides an isolated nucleic acid comprising a nucleic acid molecule encoding an antibody heavy chain variable region, and/or a nucleic acid molecule encoding an antibody light chain variable region, wherein said nucleic acid molecule encoding antibody heavy chain variable region has a sequence selected from the group consisting of: (a) the nucleotide sequence as set forth in SEQ ID NO: 54, or (b) a sequence substantially identical to that of (a) (e.g., having at least about 85%, 90%, 95%, 99% or more identity to the sequence of (a), or having one or several substituted nucleotides), or (c) a sequence that differs from the nucleotide sequence of (a) by no more than 3, 6, 15, 30 or 45 nucleotides; the nucleic acid molecule encoding antibody light chain variable region has a sequence selected from the group consisting of: (d) the nucleotide sequence as set forth in SEQ ID NO: 55, or (e) a sequence substantially identical to that of (d) (e.g., having at least about 85%, 90%, 95%, 99% or more identity to the sequence of (d), or having one or several substituted nucleotides), or (f) a sequence that differs from the nucleotide sequence of (d) by no more than 3, 6, 15, 30 or 45 nucleotides.

In some preferred embodiments, the present invention provides an isolated nucleic acid comprising a nucleic acid molecule encoding an antibody heavy chain variable region, and/or a nucleic acid molecule encoding an antibody light chain variable region, wherein said nucleic acid molecule encoding antibody heavy chain variable region has a sequence selected from the group consisting of: (a) the nucleotide sequence as set forth in SEQ ID NO: 56, or (b) a sequence substantially identical to that of (a) (e.g., having at least about 85%, 90%, 95%, 99% or more identity to the sequence of (a), or having one or several substituted nucleotides), or (c) a sequence that differs from the nucleotide sequence of (a) by no more than 3, 6, 15, 30 or 45 nucleotides; the nucleic acid molecule encoding antibody light chain variable region has a sequence selected from the group consisting of: (d) the nucleotide sequence as set forth in SEQ ID NO: 57, or (e) a sequence substantially identical to that of (d) (e.g., having at least about 85%, 90%, 95%, 99% or more identity to the sequence of (d), or having one or several substituted nucleotides), or (f) a sequence that differs from the nucleotide sequence of (d) by no more than 3, 6, 15, 30 or 45 nucleotides.

In some preferred embodiments, the nucleic acid molecule encoding an antibody heavy chain variable region has a nucleotide sequence as set forth in SEQ ID NO: 54, and the nucleic acid molecule encoding an antibody light chain variable region has a nucleotide sequence as set forth set forth in SEQ ID NO:55. In some preferred embodiments, the isolated nucleic acid molecule of the invention comprises a nucleotide sequence as set forth in SEQ ID NO: 54, which encodes an antibody heavy chain variable region, and/or a nucleotide sequence as set forth in SEQ ID NO: 55, which encodes an antibody light chain variable region.

In some preferred embodiments, the nucleic acid molecule encoding an antibody heavy chain variable region has a nucleotide sequence as set forth in SEQ ID NO: 56, and the nucleic acid molecule encoding an antibody light chain variable region has a nucleotide sequence as set forth set forth in SEQ ID NO:57. In some preferred embodiments, the isolated nucleic acid molecule of invention comprises a nucleotide sequence as set forth in SEQ ID NO: 56, which encodes an antibody heavy chain variable region, and/or a nucleotide sequence as set forth in SEQ ID NO: 57, which encodes an antibody light chain variable region.

In some preferred embodiments, the present invention provides an isolated nucleic acid comprising a nucleic acid molecule encoding an antibody heavy chain variable region, and/or a nucleic acid molecule encoding an antibody light chain variable region, wherein said nucleic acid molecule encoding antibody heavy chain variable region has a sequence selected from the group consisting of: (a) the nucleotide sequence as set forth in SEQ ID NO: 104 or 108, or (b) a sequence substantially identical to that of (a) (e.g., having at least about 85%, 90%, 95%, 99% or more identity to the sequence of (a), or having one or several substituted nucleotides), or (c) a sequence that differs from the nucleotide sequence of (a) by no more than 3, 6, 15, 30 or 45 nucleotides; the nucleic acid molecule encoding antibody light chain variable region has a sequence selected from the group consisting of: (d) the nucleotide sequence as set forth in SEQ ID NO: 105 or 109, or (e) a sequence substantially identical to that of (d) (e.g., having at least about 85%, 90%, 95%, 99% or more identity to the sequence of (d), or having one or several substituted nucleotides), or (f) a sequence that differs from the nucleotide sequence of (d) by no more than 3, 6, 15, 30 or 45 nucleotides.

In some preferred embodiments, the nucleic acid molecule encoding an antibody heavy chain variable region has a nucleotide sequence as set forth in SEQ ID NO: 104, and/or the nucleic acid molecule encoding an antibody light chain variable region has a nucleotide sequence as set forth set forth in SEQ ID NO:105.

In some preferred embodiments, the nucleic acid molecule encoding an antibody heavy chain variable region has a nucleotide sequence as set forth in SEQ ID NO: 108, and/or the nucleic acid molecule encoding an antibody light chain variable region has a nucleotide sequence as set forth set forth in SEQ ID NO:109.

Another aspect of the present invention provides a vector (such as cloning vector or expression vector), which comprises the isolated nucleic acid molecule of this invention. In some preferred embodiments, the vectors for the present invention are plasmid, cosmid, phagemid or lentivirus etc. In some preferable embodiments, said vector can express the antibody, or the antigen-binding fragment described herein in subjects (such as mammals, and human).

In some embodiments, the antibody or the antigen-binding fragment in the present invention can be used to construct Chimeric Antigen Receptor (CAR), which consists of extracellular antigen-binding domain specific for CLDN18.2 (such as scFv), transmembrane domain and one or more intracellular T cell signaling domains. In these embodiments, the isolated nucleic acid molecule of invention can include a nucleotide sequence encoding CAR, which further includes a nucleotide sequence encoding the antibody or the antigen-binding fragment (such as scFv) of the present invention. In some embodiments, the isolated nucleic acid molecule of invention encodes CAR comprising an antigen-binding fragment (such as scFv) of the antibody of the invention.

In some embodiments, the antibody or the antigen-binding fragment of the present invention can be used in chimeric antigen receptor-modified immune cells. The chimeric antigen receptor-modified immune cells include a chimeric antigen receptor (CAR), and immune cells (such as T lymphocytes, NK cells).

Another aspect of the present invention relates to a host cell, which comprises the isolated nucleic acid molecule or the vector described herein. Host cells can be eukaryotic cells (such as mammal cells, insect cells or yeast cells) or prokaryotic cells (such as *Escherichia coli*). Suitable eukaryotic cells include, but not limited to NSO cells, Vero cells, Hela cells, COS cells, CHO cells, HEK293 cells, BHK cells and MDCKII cells. Suitable insect cells include, but not limited to Sf9 cells. In some preferred embodiments, the host cell of the present invention is a mammal cell, such as CHO (such as CHO-K1, CHO-S, CHO-DXB11 or CHO DG44).

In some embodiments, the host cells for the present invention can be Chimeric Antigen Receptor T-cells (CAR-T). In these embodiments, the isolated nucleic acid molecules in the said host cells can include nucleotide sequences encoding Chimeric Antigen Receptor, which further include nucleotide sequences encoding the antibody or the antigen-binding fragment (such as scFv) of the present invention. In some embodiments, the isolated nucleic acid molecules in the said host cells encode the chimeric antigen receptor comprising an antigen-binding fragment (such as scFv) of the antibody of the present invention.

Another aspect of the present invention relates to a method for preparing the antibody or an antigen binding fragment thereof described above, which comprises culturing the host cell of the invention under conditions suitable for expression of the antibody or antigen-binding fragment thereof and recovering the antibody or antigen-binding fragment thereof from host cell cultures.

Therapeutic Methods and Pharmaceutical Compositions

Another aspect of the present invention relates to a pharmaceutical composition, comprising the antibody or antigen-binding fragment thereof, vector, host cell, conjugate, Chimeric Antigen Receptor, or the multi-specific antibody of the present invention, and a pharmaceutically acceptable carrier and/or an excipient.

In some preferred embodiments, the pharmaceutical composition of the present invention comprises the antibody or the antigen binding fragment thereof of the invention, and a pharmaceutically acceptable carrier and/or an excipient.

In some preferred embodiments, the pharmaceutical composition of the present invention comprises the vector or the host cell described herein, and a pharmaceutically acceptable carrier and/or an excipient. In these embodiments, the isolated nucleic acid molecule comprised in said vector comprises a nucleotide sequence encoding a chimeric antigen receptor, wherein the nucleotide sequence encoding a chimeric antigen receptor further comprises a nucleotide sequence encoding the antibody or antigen-binding fragment thereof (e.g., scFv) of the invention; the host cell comprises isolated nucleic acid molecule or vector as described above. In some preferred embodiments, said isolated nucleic acid molecule encodes chimeric antigen receptor, which comprises an antigen-binding fragment (such as scFv) of the antibody of the invention. In some preferred embodiments, said host cell is T cell. In some preferred embodiments, said host cell is chimeric antigen receptor T cell (CAR-T).

In some preferred embodiments, said pharmaceutical composition comprises other pharmaceutical active agents. In some preferred embodiments, said other pharmaceutical active agents are drugs used to treat immune related diseases. In some preferred embodiments, said other pharmaceutical active agents are drugs with anti-tumor activities. In some preferred embodiments, said other pharmaceutical active agents are interferon or IL-2 or chemotherapy drugs.

In some preferred embodiments, in the said pharmaceutical composition, the antibody of the present invention or the antigen-binding fragment thereof may be provided as separate components or as components of a single composition. Therefore, the antibody or the antigen-binding fragment thereof of the present invention may be used with other said pharmaceutical active agents simultaneously, separately or successively.

In some preferred embodiments, the said pharmaceutical composition may further comprise an additional pharmaceutical active agent. The additional pharmaceutical active agents is one or more agents selected from a group of epirubicin, oxaliplatin, capecitabine, 5-fluorouracil, leucovorin, paclitaxel, albumin-bound paclitaxel, combination of epirubicin+oxaliplatin+5-fluorouracil, FOLFOX4, FOLFOX6, mFOLFOX6 (including oxaliplatin, leucovorin and 5-fluorouracil).

In another aspect, the antibody and an antigen-binding fragment thereof, the vector, the host cell, the conjugate, the chimeric antigen receptor or the multi-specific antibody in the pharmaceutical composition of the present invention are sufficient in the subject to:
 (a) induce apoptosis in tumor cells;
 (b) inhibit tumor cell proliferation;
 (c) induce and/or increase T cell infiltration;
 (d) induce and/or enhance the immune response;
 (e) induce and/or increase complement dependent cytotoxicity;
 (f) induce and/or increase antibody-dependent cytotoxicity;
 (g) increase NK cell activity;
 (h) inhibit the expression and activation of CLDN18.2;
 (i) inhibit CLDN18.2-mediated cell signaling pathway; or
 (j) any combination of (a) to (i).

In another aspect, a pharmaceutical composition of the present invention further includes a second antibody or a nucleic acid encoding the second antibody, the antibody specifically binds to a receptor or ligand selected from the group consisting of: PD-1, PD-L1, PD-L2, TIM-3, LAG-3, VISTA, CTLA-4, OX40, BTLA, 4-1BB, CD96, CD27, CD28, CD40, LAIR1, CD160, 2B4, TGF-R, KIR, ICOS, GITR, CD3, CD30, BAFFR, HVEM, CD7, LIGHT, SLAMF7, NKp80, B7-H3 and any combination thereof.

Another aspect of the present invention relates to the use of the antibody or an antigen-binding fragment thereof, the vector, the host cell, the conjugate, the chimeric antigen receptor or the multi-specific antibody of the present invention in the manufacture of a medicament, wherein said medicament is used to:
 (a) induce apoptosis in tumor cells;
 (b) inhibit tumor cell proliferation;
 (c) increase immune cell activities in vitro or in subjects (e.g., humans);
 (d) enhance an immune response in subjects (e.g., humans);
 (e) treat a tumor in subjects (e.g., humans);
 (f) induce and/or increase T cell infiltration;
 (g) induce and/or enhance an immune reaction;
 (h) inducing and/or increase complement dependent cytotoxicity;
 (i) induce and/or increase antibody-dependent cytotoxicity;
 (j) increase NK cell activity;
 (k) inhibit the expression and activation of CLDN18.2;
 (l) inhibit CLDN18.2-mediated cell signaling pathway; or
 (m) any combination of (a) to (l).

In some preferred embodiments, when the vector or the host cell of the present invention is used to prepare drugs, the isolated nucleic acid molecule comprised in said vector comprises a nucleotide sequence encoding a chimeric antigen receptor, wherein the nucleotide sequence encoding a chimeric antigen receptor further comprises a nucleotide sequence encoding the antibody or antigen-binding fragment thereof (e.g., scFv) of the invention; the host cell comprises isolated nucleic acid molecule or vector as described above. In some preferred embodiments, said isolated nucleic acid molecule encodes chimeric antigen receptor, which comprises the antigen-binding fragment (such as scFv) of the antibody of the present invention. In some preferred embodiments, said host cell is T cell. In some preferred embodiments, said host cell is chimeric antigen receptor T cell (CAR-T).

In some preferred embodiments, when the vector or the host cell of the present invention is used to prepare drugs, said drugs are used to treat tumor in subjects (such as human).

In some preferred embodiments, the antibody or an antigen-binding fragment thereof, the vector, the host cell, the conjugate, the chimeric antigen receptor or the multi-specific antibody of the present invention relates to tumors including a solid tumor, a hematological tumor (such as leukemia, lymphoma and myeloma, e.g., multiple myeloma) or a metastatic, refractory or recurrent lesion of cancer, such as, but not limited to esophageal cancer, gastrointestinal cancer, pancreatic cancer, thyroid cancer, colorectal cancer, kidney cancer, lung cancer (e.g., non-small cell lung cancer), liver cancer, stomach cancer, gastroesophageal junction (GEJ) adenocarcinoma, head and neck cancer, bladder cancer, breast cancer, uterine cancer, cervical cancer, ovarian cancer, prostate cancer, testicular cancer, germ cell cancer, bone cancer, skin cancer, thymic cancer, cholangiocarcinoma, gallbladder cancer, melanoma, mesothelioma, lymphoma, myeloma (e.g., multiple myeloma), sarcoma, glioblastoma, leukemia.

In some preferred embodiments, the antibody of the present invention or an antigen-binding fragment thereof relates to tumors including gastric cancer, gastroesophageal junction (GEJ) adenocarcinoma, esophageal cancer, gastrointestinal cancer, pancreatic cancer, lung cancer (e.g., non-small cell lung cancer).

In some preferred embodiments, the antibody of the present invention or an antigen-binding fragment thereof relates to tumors including gastric cancer or gastroesophageal junction (GEJ) adenocarcinoma, such as a locally advanced unresectable gastric cancer or GEJ adenocarcinoma, or a metastatic gastric cancer or GEJ adenocarcinoma.

In some preferred embodiments, the antibody of the present invention or an antigen-binding fragment thereof relates to tumor which is CLDN 18.2 positive, further, the tumor is HER2 negative.

In some preferred embodiments, the antibody of the present invention or an antigen-binding fragment thereof relates to tumor which is HER2 negative.

In another aspect, the present invention provides a method to prevent and/or treat tumor in subjects. In another aspect, the present invention provides a method to delay tumor progress in subjects. In another aspect, the present invention provides a method to reduce or inhibit tumor recurrence in subjects. The methods include administrating to a subject in need thereof with an effective amount of the antibody or an antigen-binding fragment thereof, the vector, the host cell, the conjugate, the chimeric antigen receptor, the multi-specific antibody or the pharmaceutical composition of the present invention.

In some embodiments, the present invention provides a method for preventing and/or treating a tumor in a subject, comprising administering to the subject in need thereof an effective amount of the antibody or an antigen-binding fragment thereof, the vector, the host cell, the conjugate, the chimeric antigen receptor, the multi-specific antibody of the invention and a pharmaceutically acceptable carrier and/or excipient; which is administered separately, in combination, simultaneously, or sequentially with an additional active pharmaceutical agent.

In some preferred embodiments, the additional active pharmaceutical agent is one or more agents selected from a group consist of: epirubicin, oxaliplatin, capecitabine, 5-fluorouracil, leucovorin, paclitaxel, albumin-bound paclitaxel, combination of epirubicin+oxaliplatin+5-fluorouracil, FOLFOX4, FOLFOX6, mFOLFOX6 (including oxaliplatin, leucovorin and 5-fluorouracil).

When the host cell of the present invention is used for the abovementioned methods, said host cell expresses chimeric antigen receptor, which comprises the antigen-binding fragment (such as scFv) of the antibody of the invention. Therefore, in some preferred embodiments, said isolated nucleic acid molecule comprised by host cell comprises a nucleotide sequence encoding chimeric antigen receptor; said nucleotide sequence encoding chimeric antigen receptor further comprises nucleotide sequence encoding the antibody of the present invention or the antigen-binding fragment thereof (such as scFv). In some preferred embodiments, said isolated nucleic acid molecule encodes chimeric antigen receptor, which comprises the antigen-binding fragment of the antibody of the present invention (such as scFv). In some preferred embodiments, said host cell is T cell. In some preferred embodiments, said host cell is chimeric antigen receptor T cell (CAR-T).

In another aspect, the above described method also includes administrating a second therapy to the subject, the second therapy being selected from the group consisting of surgery, chemotherapy, radiation therapy, immunotherapy, gene therapy, DNA therapy, RNA therapy, nano therapy, viral therapy, adjuvant therapy, and any combination thereof.

In some embodiments, the second therapy can be administered separately or in combination with the method described above; or, the second therapy can be administered separately or in combination, simultaneously or sequentially with the method described above.

In some preferred embodiments, the chemotherapy is selected from the group consisting of: epirubicin, oxaliplatin, capecitabine, 5-fluorouracil, leucovorin, paclitaxel, albumin-bound paclitaxel, combination of epirubicin+oxaliplatin+5-fluorouracil, FOLFOX4, FOLFOX6, mFOLFOX6 (including oxaliplatin, leucovorin and 5-fluorouracil).

In some preferred embodiments, the antibody or an antigen-binding fragment thereof, the vector, the host cell, the conjugate, the chimeric antigen receptor or a modified immune cell thereof or the multi-specific antibody of the present invention relates to tumors including a solid tumor, a hematological tumor (such as leukemia, lymphoma and myeloma, e.g., multiple myeloma) or a metastatic, refractory or recurrent lesion of cancer, such as, but not limited to esophageal cancer, gastrointestinal cancer, pancreatic cancer, thyroid cancer, colorectal cancer, kidney cancer, lung cancer (e.g., non-small cell lung cancer), liver cancer, stomach cancer, gastroesophageal junction (GEJ) adenocarcinoma, head and neck cancer, bladder cancer, breast cancer, uterine cancer, cervical cancer, ovarian cancer, prostate cancer, testicular cancer, germ cell cancer, bone cancer, skin cancer, thymic cancer, cholangiocarcinoma, gallbladder cancer, melanoma, mesothelioma, lymphoma, myeloma (e.g., multiple myeloma), sarcoma, glioblastoma, leukemia.

In some preferred embodiments, the antibody of the present invention or an antigen-binding fragment thereof relates to tumors selected from the group consisting of gastric cancer, gastroesophageal junction (GEJ) adenocarcinoma, esophageal cancer, gastrointestinal cancer, pancreatic cancer, lung cancer (e.g., non-small cell lung cancer).

In some preferred embodiments, the antibody of the present invention or an antigen-binding fragment thereof relates to tumors including gastric cancer or gastroesophageal junction (GEJ) adenocarcinoma, such as a locally advanced unresectable gastric cancer or GEJ adenocarcinoma, or a metastatic gastric cancer or GEJ adenocarcinoma.

In some preferred embodiments, the antibody of the present invention or an antigen-binding fragment thereof relates to tumor which is CLDN 18.2 positive, further, the tumor is HER2 negative.

In some preferred embodiments, the antibody of the present invention or an antigen-binding fragment thereof relates to tumor which is HER2 negative.

In some preferred embodiments, the antibody of the present invention or an antigen-binding fragment thereof relates to tumor which is HER2 negative.

In another aspect, the above described method also includes administrating a second therapy to the subject, the second therapy being selected from the group consisting of surgery, chemotherapy, radiation therapy, immunotherapy, gene therapy, DNA therapy, RNA therapy, nano-therapy, viral therapy, adjuvant therapy, and any combination thereof.

The antibody or an antigen-binding fragment thereof or the pharmaceutical composition of the present invention can be formulated into any pharmaceutical formulations known in the medical field, such as tablets, pills, suspensions, emulsions, solutions, gels, capsules, powders, granules, elixirs, lozenges, suppositories, injections (including injection, sterile powder for injection and concentrated solution for injection), inhalant, spray, or the like. Preferred dosage form depends on the intended mode of administration and therapeutic use. The pharmaceutical composition of the invention should be sterile and stable under manufacture and storage condition. A preferred pharmaceutical formulation is injection. The injection may be sterile injection solution. For example, the following methods could be used to prepare sterile injection solution: a necessary dosage of the recombinant protein is dispersed in a proper carrier, optionally with other desired ingredients (including but not limited to pH adjusting agent, surfactant, adjuvant, ionic strength enhancer, isotonicity agent, preservative, diluent, or any combination thereof), followed by filtration sterilization. In addition, sterile injection solution can be used to prepare sterile lyophilized powder (such as by vacuum drying or lyophilizing) to facilitate storage and usage. The sterile lyophilized powder can be dispersed in a suitable carrier before use, such as sterile pyrogen-free water.

Furthermore, the antibody or antigen-binding fragment thereof of the present invention may be present in a pharmaceutical composition in the form of a unit dose to facilitate administration.

The antibody or an antigen-binding fragment thereof or pharmaceutical composition of the invention may be administered by any suitable method known in the art, including but not limited to, oral, buccal, sublingual, ocular, topical, parenteral, rectal, intrathecal, intra-cisterna, in the groin, intravesical, local (such as powder, ointment or drops), or nasal route. However, for many therapeutic uses, the preferred route/mode of administration is parenteral (such as intravenous, subcutaneous, intraperitoneal, intramuscular). The skill person will appreciate that the route and/or manner of administration will vary depending on the intended purpose. In a preferred embodiment, the antibody or antigen-binding fragment thereof, pharmaceutical composition of the invention is administered by intravenous infusion or injection.

The pharmaceutical compositions of the invention may comprise a "therapeutically effective dose" or a "prophylactically effective dose" of the antibody of the invention or an antigen-binding fragment thereof. "Prophylactically effective dose" means an amount sufficient to prevent, inhibit, or delay the onset of a disease. "Therapeutically effective amount" means an amount sufficient to cure or at least partially inhibit the disease and its complications in a patient already suffering from the disease. The therapeutically effective dose of the antibody or an antigen-binding fragment thereof of the present invention may vary depending on factors such as the severity of the disease to be treated, the overall state of the patient's own immune system, the general condition of the patient such as age, weight and sex, and administration of drug, as well as other treatments for simultaneous administration, and the like.

In the present invention, the dosage regimen can be adjusted to achieve an optimal intended response (such as therapeutic or prophylactic response). For example, it may be administered in a single administration, may be administered multiple times over a period of time, or may be administrated in proportionally reduced or increased dosage according to the urgency of the treatment.

A typical non-limiting therapeutically or prophylactically effective dose range of the recombinant protein of the invention is from 0.02 to 100 mg/kg, such as from 0.1 to 100 mg/kg, from 0.1 to 50 mg/kg, or from 1 to 50 mg/kg. It should be noted that the dosage may vary depending on the type and severity of the condition to be treated. Moreover, it will be understood by those skilled in the art that for any particular patient, the particular dosage regimen should be adjusted over time according to the needs of the patient and the professional evaluation by the physician; the dosage ranges given herein are for illustrative purposes only and are not for limiting the use or range of the pharmaceutical compositions of the invention.

In the present invention, the subject may be a mammal, such as a human.

Detection Method and Kit

The antibody or an antigen-binding fragment thereof of the invention is capable of specifically binding to CLDN 18.2 and thus can be used to detect the presence or level of CLDN 18.2 in a sample.

Thus, in another aspect, the invention provides a kit comprising the antibody of the invention or an antigen binding fragment thereof. In some preferred embodiments, the antibody of the invention or antigen-binding fragment thereof carries a detectable label. In a preferred embodiment, the kit further comprises a second antibody that specifically recognizes the antibody of the invention or an antigen-binding fragment thereof. Preferably, the second antibody further comprises a detectable label.

In the present invention, the detectable label can be any substance detectable by fluorescence, spectroscopic, photochemical, biochemical, immunological, electrical, optical or chemical means. It is particularly preferred that such markers are suitable for use in immunological assays (such as enzyme-linked immunoassays, radio immunoassays, fluorescent immunoassays, chemiluminescent immunoassays, etc.). Such labels are well known in the art, examples of which include, but are not limited to, enzymes (e.g., horseradish peroxidase, alkaline phosphatase, beta-galactosidase, urease, glucose oxidase, etc.), radionuclides (e.g., 3H, 125I, 35S, 14C or 32P), fluorescent dyes (e.g., fluorescein isothiocyanate (FITC), fluorescein, tetramethylrhodamine isothiocyanate (TRITC), phycoerythrin (PE), Texas Red, Rhodamine, quantum dot or cyanine dye derivatives (e.g., Cy7, Alexa 750), acridinium esters, magnetic beads (e.g., Dynabeads®), calorimetric labels such as colloids Gold or tinted glass or plastic (e.g., polystyrene, polypropylene, latex, etc.) beads, and biotin for binding to the above-described label modified avidin (e.g., streptavidin). Patents that teach the use of such markers include, but are not limited to, U.S. Pat. Nos. 3,817,837, 3,850,752, 3,939,350, 3,996,345, 4,277,437, 4,275,149, and 4,366,241 (each incorporated herein by references). The detectable label as described above can be detected by methods known in the art. For example, the radioactive label can be detected using a photographic film or a scintillation counter, and the fluorescent label can be detected using a photodetector to detect the emitted light. Enzyme labels are typically detected by providing a substrate for the enzyme and detecting the reaction product produced by the action of the enzyme on the substrate, and the thermo-label is detected by simply visualizing the stained label. Enzyme labels are typically detected by providing a substrate for the enzyme and detecting the reaction product produced by the action of the enzyme on the substrate, and the thermo-label is detected by simply visualizing the stained label. In certain embodiments, a detectable label as described above can be linked to a recombinant protein of the invention by a linker of varying length to reduce potential steric hindrance.

In another aspect, the invention provides a method of detecting the presence or level of CLDN18.2 in a sample, which comprises a step of using an antibody of the invention or an antigen-binding fragment thereof. In a preferred embodiment, the antibody of the invention or the antigen-binding fragments thereof also carries a detectable label. In another preferred embodiment, the method further comprises detecting the antibody of the invention or the antigen-binding fragment thereof using a reagent with a detectable label. The method can be used for diagnostic purposes, or for non-diagnostic purposes (for example, the sample is a cell sample, not a sample from a patient).

In another aspect, the invention provides a method of detecting the presence or level of CLDN18.2 in a sample. The method comprises contacting the sample with an antibody or antigen-binding fragments thereof to enable the formation of a complex between the antibody or antigen-binding fragment thereof and CLDN 18.2, and detecting the presence of the complex between the antibody or fragment and CLDN 18.2.

In another aspect, the use of an antibody of the invention or an antigen-binding fragment thereof in the preparation of a kit is provided. The kit is used for detecting the presence or level of CLDN 18.2 in a sample. In another aspect, the invention provides a diagnostic or therapeutic kit comprising an antibody or an antigen-binding fragment thereof, a vector, a host cell, a conjugate, a chimeric antigen receptor, or a multi-specific antibody of the invention, and an instruction for use.

In view of the low or no expression of Claudin 18.2 in normal tissues and the expression or high expression in some cancers, tumors and tumor metastasis can be diagnosed by detecting the presence or level of CLDN 18.2 in samples. For example, if CLDN 18.2 is detected in lung tissues, it can be basically judged that the lung tissue has become cancerous. Combined with some other indicators, such as pathological morphology, it can be further judged whether the cancer is gastric cancer metastasis or non-small cell lung cancer, so as to identify the subtype of cancer. Therefore, the antibodies or antigen-binding fragments, conjugates, multi-specific antibodies, or kits of the present invention can be used to diagnose tumors and tumor metastasis. Therefore, in another aspect, the use of the antibody or antigen-binding fragment, conjugate, multi-specific antibody, or kit of the present invention in the diagnosis of tumors and tumor metastasis is provided.

The antibody of the present invention has a high binding affinity and extremely high specificity to CLDN18.2. Thus, the antibodies of the invention have the potential to prevent and/or treat tumors. The humanized antibodies of the invention retain the functions and properties of the parental mouse antibody. Moreover, the humanized antibodies of the present invention have a high degree of humanization so that they can be safely administered to a human subject without eliciting an immunogenic response. Therefore, the antibodies (especially humanized antibodies) of the invention have significant clinical values.

ABBREVIATION

CDR Complementarity-determine region of immunoglobulins
FR Framework region of antibody; including amino acid residues in antibody variable region other than CDR
VH Variable region of antibody heavy chain
VL Variable region of antibody light chain
IgG Immunoglobulin G
AbM The definition of AbM CDR comes from Martin's related research (Martin A C R, Cheetham J C, Rees A R (1989) Modelling antibody hypervariable loops: A combined algorithm. Proc Natl Acad Sci USA 86:9268-9272), this definition method integrates the partial definitions of Kabat and Chothia.
Kabat An Immunoglobulin reference and numbering system proposed by Elvin A. Kabat (see, for example, Kabat et al., Sequences of Proteins of Immunological Interest, 5th Ed. Public Health Service, National Institutes of Health, Bethesda, Md., 1991)
Chothia An Immunoglobulin numbering system proposed by Chothia et al., which is a classic rule for identifying the boundaries of CDR regions based on the location of the structural loop region. (see, for example, Chothia & Lesk (1987) J. Mol. Biol. 196:901-917; Chothia et al. (1989) Nature 342:878-883)
IMGT A numbering system based on the international ImMunoGeneTics information System® (IMGT) initiated by Lefranc et al., See, Lefranc et al., Dev. Comparat. Immunol. 27:55-77, 2003
mAb Monoclonal antibody
EC50 A concentration at which 50% efficacy or binding is produced
IC50 A concentration at which 50% inhibition is produced
ELISA Enzyme-linked immunosorbent assay
PCR Polymerase chain reaction
HRP Horseradish peroxidase
IL-2 Interleukin 2
KD Equilibrium dissociation constant
Ka Association rate constant
Kd Dissociation rate constant
ADCC Antibody-dependent cell-mediated cytotoxicity
CDC Complement dependent cytotoxicity
FAC S Fluorescence-activated cell sorting
CDR-H1 Complementarity-determining region 1 of heavy chain variable region
CDR-H2 Complementarity-determining region 2 of heavy chain variable region
CDR-H3 Complementarity-determining region 3 of heavy chain variable region
CDR-L1 Complementarity-determining region 1 of light chain variable region
CDR-L2 Complementarity-determining region 2 of light chain variable region
CDR-L3 Complementarity-determining region 3 of light chain variable region Definitions of Terms In the present invention, unless otherwise specified, the scientific and technical terms used herein have the meanings commonly understood by those skilled in the art. Moreover, laboratory procedures of cell culture, biochemistry, nucleic acid chemistry, immunology used herein are all routine steps widely used in the corresponding fields. At the same time, in order to better understand the present invention, definitions and explanations of related terms are provided below.

As used herein, the term "antibody" refers to an immunoglobulin molecule usually composed of two pairs of polypeptide chains (each pair has a light chain (LC) and a heavy chain (HC)). Antibody light chains can be classified into κ (kappa) and λ, (lambda) light chains. Heavy chains can be classified into μ, δ, γ, α or ε heavy chains, and the isotypes of antibody are therefore defined as IgM, IgD, IgG, IgA and IgE, respectively. Within the light and heavy chains, the variable and constant regions are connected by a "J" region of about 12 or more amino acids, and the heavy chain also includes a "D" region of about 3 or more amino acids. Each heavy chain is composed of a heavy chain variable region (VH) and a heavy chain constant region (CH). The heavy chain constant region is composed of 3 domains (CH1, CH2 and CH3). Each light chain is composed of a light chain variable region (VL) and a light chain constant region (CL). The light chain constant region consists of one domain CL. The constant domains are not directly involved in the binding of antibodies and antigens, but exhibit a variety of effector functions, such as mediating the binding of immunoglobulins to host tissues or factors, including various cells (for example, effector cells) of immune system and the first component (C1q) of classical complement system. The VH and VL regions can also be subdivided into hypervariable regions (called complementarity determining regions (CDR)), interspersed with more conservative regions (called framework regions (FR)). Each VH and VL consists of 3 CDRs and 4 FRs arranged in the following order: FR1, CDR1, FR2, CDR2, FR3, CDR3, FR4 from the amino terminus to the carboxy terminus. The variable regions (VH and VL) of each heavy chain/light chain pair form antigen binding sites respectively. The assignment of amino acids in each region or domain may follow the definition of Kabat, Sequences of Proteins of Immunological Interest (National Institutes of Health, Bethesda, Md. (1987 and 1991)), or Chothia & Lesk (1987) J. Mol. Biol. 196: 901-917; Chothia et al. (1989) Nature 342:878-883, or AbM, Martin's related research (Martin A C R, Cheetham J C, Rees A R (1989) Modelling antibody hypervariable loops: A combined algorithm. Proc Natl Acad Sci USA 86:9268-9272).

In this context, unless the context clearly dictates otherwise, when the term "antibody" is referred to, it includes not only intact antibody but also antigen-binding fragments of antibody.

As used herein, the term "complementarity determining region" or "CDR" refers to the amino acid residues in antibody variable region that are responsible for antigen binding. The precise boundaries of these amino acid residues can be defined according to various numbering systems known in the art, for example, according to the Kabat numbering system (Kabat et al., Sequences of Proteins of Immunological Interest, 5th Ed. Public Health Service, National Institutes of Health, Bethesda, Md., 1991), Chothia numbering system (Chothia & Lesk (1987) J. Mol. Biol. 196:901-917; Chothia et al. (1989) Nature 342:878-883), IMGT numbering system (Lefranc et al., Dev. Comparat. Immunol. 27:55-77, 2003), or the definition of Martin's related research (Martin A C R, Cheetham J C, Rees A R (1989) Modelling antibody hypervariable loops: A combined algorithm. Proc Natl Acad Sci USA 86:9268-9272), the definition method of which integrates the parts of definitions of Kabat and Chothia, and was first applied in Oxford Molecular antibody modeling software (Martin A C R. Protein sequence and structure analysis of antibody variable domains[M]//Antibody engineering. Springer, Berlin, Heidelberg, 2010: 33-51.). For a given antibody, those skilled in the art will easily identify the CDRs defined by each numbering system. Moreover, the correspondence between different numbering systems is well known to those skilled in the art (for example, see Lefranc et al., Dev. Comparat. Immunol. 27:55-77, 2003).

In the present invention, the CDR contained in the antibody or antigen-binding fragment thereof of the present invention can be determined according to various numbering systems known in the art. In certain embodiments, the CDRs contained in the antibody or antigen-binding fragment thereof of the present invention are preferably determined by the Kabat, Chothia, IMGT or AbM numbering system.

As used herein, the term "framework region" or "FR" residues refer to those amino acid residues in the variable region of antibody other than the CDR residues as defined above.

The "germline antibody gene" is an immunoglobulin sequence encoded by non-lymphocytes, which has not undergone a maturation process that can lead to genetic rearrangement and maturation for expression of a particular immunoglobulin. One advantage provided by various embodiments of the present invention is derived from the recognition that a germline antibody gene retains more important amino acid sequence structures characterizing individual animal species than a mature antibody gene. Therefore, when applied therapeutically to this species, it is less recognized as a foreign substance by this species.

The term "antibody" is not limited by any specific method for producing antibodies. For example, it includes recombinant antibody, monoclonal antibody, and polyclonal antibody. The antibody may be an antibody of any isotypes, for example, an antibody of IgG (e.g., IgG1, IgG2, IgG3 or IgG4 subtype), IgA1, IgA2, IgD, IgE or IgM.

As used herein, the term "antigen-binding fragment" of antibody refers to a polypeptide of antibody fragment, such as a polypeptide of fragment of full-length antibody, which retains the ability to specifically bind to the same antigen to which the full-length antibody binds, and/or compete with the full-length antibody for specific binding to the antigen, which is also called "antigen-binding portion". See generally, Fundamental Immunology, Ch. 7 (Paul, W., ed., 2nd edition, Raven Press, NY (1989), which is incorporated herein by reference in its entirety for all purposes. Recombinant DNA technology or enzymatic or chemical cleavage of an intact antibody can be used to produce an antigen-binding fragment of the antibody. Non-limiting examples of antigen-binding fragment include Fab, Fab', F(ab')$_2$, Fd, Fv, dAb, and complementarity determining region (CDR) fragment, single chain antibody (e.g., scFv), chimeric antibody, diabody, linear antibody, nanobody (technology of which is from Domantis), domain antibody (technology of which is from Ablynx), and such polypeptides, which contain at least a portion of antibody that is sufficient to confer the polypeptide a specific antigen binding ability. Engineered antibody variants are reviewed by Holliger et al., 2005; Nat Biotechnol, 23: 1126-1136.

As used herein, the term "full-length antibody" refers to an antibody composed of two "full-length heavy chains" or "heavy chains" and two "full-length light chains" or "light chains", wherein the "full-length heavy chain" or "heavy chain" refers to a polypeptide chain that consists of a heavy chain variable region (VH), a heavy chain constant region CH1 domain, a hinge region (HR), a heavy chain constant region CH2 domain, and a heavy chain constant region CH3 domain in the N-terminal to C-terminal direction; and, when the full-length antibody is of the IgE isotype, it optionally also comprises a heavy chain constant region CH4 domain. Preferably, the "full-length heavy chain" is a polypeptide chain composed of VH, CH1, HR, CH2 and CH3 in the N-terminal to C-terminal direction. The "full-length light chain" or "light chain" is a polypeptide chain composed of a light chain variable region (VL) and a light chain constant region (CL) in the N-terminal to C-terminal direction. The two pairs of full-length antibody chains are connected by a disulfide bond between the CL and CH1 and a disulfide bond between the HR of the two full-length heavy chains. The full-length antibody of the present invention can be from a single species, such as a human; it can also be a chimeric antibody or a humanized antibody. The full-length antibody of the present invention comprises two antigen binding sites formed by a pair of VH and VL respectively, and the two antigen binding sites specifically recognize/bind the same antigen.

As used herein, the term "Fd fragment" refers to an antibody fragment composed of VH and CH1 domains; the term "dAb fragment" refers to an antibody fragment composed of VH domains (Ward et al., Nature 341:544 546 (1989)); the term "Fab fragment" refers to an antibody fragment composed of VL, VH, CL and CH1 domains; the term "F(ab')$_2$ fragment" refers to an antibody fragment comprising two Fab fragments connected by a disulfide bridge of the hinge region; the term "Fab' fragment" refers to a fragment obtained by reducing the disulfide bond connecting the two heavy chain fragments in F(ab')$_2$ fragment, consisting of an intact light chain and a heavy chain Fd fragment (consisting of VH and CH1 domains).

As used herein, the term "Fv fragment" refers to an antibody fragment composed of the VL and VH domains of a single arm of antibody. Fv fragment is generally considered to be the smallest antibody fragment that can form a complete antigen binding site. It is generally believed that six CDRs can confer antigen binding specificity to antibody. However, even a variable region (e.g., a Fd fragment, which contains only three antigen-specific CDRs) can recognize and bind an antigen, although its affinity may be lower than that of the complete binding site.

As used herein, the term "Fc fragment" refers to an antibody fragment formed with the second and third constant regions of first heavy chain and the second and third constant regions of second heavy chain of an antibody that are bound through a disulfide bond. The Fc fragment of antibody has many different functions, but does not participate in antigen binding.

As used herein, the term "scFv" refers to a single polypeptide chain comprising VL and VH domains, wherein the VL and VH are connected by a linker (see, for example, Bird et al., Science 242:423-426 (1988); Huston et al., Proc. Natl. Acad. Sci. USA 85:5879-5883 (1988); and Pluckthun, The Pharmacology of Monoclonal Antibodies, Volume 113, edited by Roseburg and Moore, Springer-Verlag, New York, pp. 269-315 (1994)). Such scFv molecule may have a general structure: NH$_2$-VL-linker-VH-COOH or NH$_2$-VH-linker-VL-COOH. A suitable linker of prior art consists of a repeated GGGGS amino acid sequence or variants thereof. For example, a linker having amino acid sequence (GGGGS)$_4$ can be used, but variants thereof can also be used (Holliger et al. (1993), Proc. Natl. Acad. Sci. USA 90: 6444-6448). Other linkers that can be used in the present invention are described by Alfthan et al. (1995), Protein Eng. 8:725-731, Choi et al. (2001), Eur. J. Immunol. 31: 94-106, Hu et al. (1996), Cancer Res. 56:3055-3061, Kipriyanov et al. (1999), J. Mol. Biol. 293:41-56 and Roovers et al. (2001), Cancer Immunol. In some cases, there may also be a disulfide bond between the VH and VL of scFv. As used herein, the term "di-scFv" refers to an antibody fragment formed by linking two scFvs.

As used herein, the term "diabody" refers to that its VH and VL domains are expressed on a single polypeptide chain, but the linker used is too short to allow the pairing between the two domains of the same chain, so that the domains are forced to pair with the complementary domains of another chain and create two antigen binding sites (see, for example, Holliger P. et al., Proc. Natl. Acad. Sci. USA 90: 6444-6448 (1993), and Poljak R J et al., Structure 2:1121-1123 (1994)).

Each of the aforementioned antibody fragments maintains the ability to specifically bind to the same antigen to which the full-length antibody binds, and/or compete with the full-length antibody for specific binding to the antigen.

As used herein, "bispecific antibody" refers to a conjugate formed by a first antibody (fragment) and a second antibody (fragment) or antibody mimetics through a coupling arm. The coupling mode includes but is not limited to chemical reaction, gene fusion, protein fusion, polypeptide fusion and enzymatic reaction. "Multispecific antibody" comprises, for example, trispecific antibody and tetraspecific antibody, in which the former is an antibody with three different antigen binding specificities, and the latter is an antibody with four different antigen binding specificities.

As used herein, "antibody mimetics" refers to substances that specifically bind to an antigen as an antibody does, but do not have the structure of antibody. They are usually artificial peptides or proteins with a molar mass of about 3 to 20 kDa, such as ankyrin repeat protein (DARPin) and fynomer. The designed ankyrin repeat protein (DARPin) is linked to IgG antibody, scFv-Fc antibody fragment or a combination thereof, as in CN104341529A. The anti-IL-17a fynomer binds to anti-IL-6R antibody, as in WO2015141862A1.

As used herein, "Chimeric Antigen Receptor (CAR)" refers to a tumor antigen binding domain fused to an intracellular signal transduction domain, which can activate T cells. Commonly, the extracellular binding domain of CAR is derived from a mouse or humanized or human monoclonal antibody.

As used herein, "immunoglobulin" or "Ig" can refer to a type of protein that functions as an antibody. The antibodies expressed by B cells are sometimes called chimeric antigen receptors or antigen receptors. The five members included in this class of proteins are IgA, IgG, IgM, IgD, and IgE, wherein IgG is the most common circulating antibody, which is the most effective immunoglobulin in agglutination, complement fixation and other antibody responses, and is important in defense against bacteria and viruses.

In this context, the antigen-binding fragment (e.g., the above-mentioned antibody fragment) of antibody can be obtained from a given antibody (e.g., the antibody provided by the present invention) using a conventional technique known to those skilled in the art (e.g., recombinant DNA technology or enzymatic or chemical fragmentation methods), and can be screened for specificity in the same manner by which intact antibodies are screened.

As used herein, the terms "monoclonal antibody" and "mAb" have the same meaning and are used interchangeably, which refer to an antibody or a fragment of an antibody derived from a group of highly homologous antibody molecules, that is, a group of identical antibody molecules except for natural mutations that may occur spontaneously. The monoclonal antibody has high specificity for a single epitope on antigen. Polyclonal antibodies are mentioned relative to the monoclonal antibody, and usually comprise at least two or more different antibodies, and these different antibodies usually recognize different epitopes on the antigen. In addition, the modifier "monoclonal" merely indicates the character of the antibody as being obtained from a highly homogeneous population of antibodies, and is not to be construed as requiring production of the antibody by any particular method.

The monoclonal antibody of the present invention can be prepared by a variety of techniques, such as hybridoma technology (see, for example, Kohler et al. Nature, 256:495, 1975), recombinant DNA technology (see, for example, U.S. Pat. No. 4,816,567), or phage antibody library technology (see, for example, Clackson et al. Nature 352:624-628, 1991, or Marks et al. J. Mol. Biol. 222:581-597, 1991).

For example, monoclonal antibodies can be prepared as follows. The mice or other suitable host animals are first immunized with immunogen (with addition of an adjuvant if necessary). The method of injection of immunogen or adjuvant is usually multi-point subcutaneous injection or intra-peritoneal injection. Immunogen can be pre-coupled to certain known proteins, such as serum albumin or soybean trypsin inhibitors, to enhance the immunogenicity of the antigen in the host. The adjuvant may be Freund's adjuvant or MPL-TDM or the like. After the animal is immunized, the body will produce lymphocytes that secrete antibodies that specifically bind to the immunogen. In addition, lymphocytes can also be obtained by in vitro immunization. The lymphocytes of interest are collected and fused with myeloma cells using a suitable fusing agent, such as PEG, to obtain hybridoma cells (Goding, Monoclonal Antibodies: Principles and Practice, pp. 59-103, Academic Press, 1996). The hybridoma cells prepared above may be inoculated into a suitable culture medium which preferably contains one or more substances capable of inhibiting the growth of unfused, parental myeloma cells. For example, for parental myeloma cells lacking hypoxanthine guanine phosphotransferase (HGPRT or HPRT), the addition of hypoxanthine, aminopterin, and thymine (HAT medium) to the culture medium will inhibit growth of HGPRT-defective cells. Preferred myeloma cells should have a high fusion rate, stable antibody secretion capacity, and sensitivity to HAT culture medium. Among them, murine myeloma is preferred for myeloma cells, such as MOP-21 or MC-11 mouse tumor-derived strains (THE Salk Institute Cell Distribution Center, San Diego, Calif. USA), and SP-2/0 or X63-Ag8-653 cell line (American Type Culture Collection, Rockville, Md. USA). In addition, studies have also reported the use of human myeloma and human-murine heterologous myeloma cell lines to prepare human monoclonal antibodies (Kozbor, J. Immunol., 133: 3001 (1984); Brodeur et al., Monoclonal Antibody Production Techniques and Applications, pp 51-63, Marcel Dekker, Inc., New York, 1987). The culture medium for growing hybridoma cells is used to detect the production of monoclonal antibodies against specific antigens. Methods for determining the binding specificity of monoclonal antibodies produced by hybridoma cells include, for example, immunoprecipitation or in vitro binding assays such as radioimmunoassay (RIA), enzyme-linked immunosorbent assay (ELISA). For example, the affinity of the monoclonal antibody can be determined using the Scatchard assay described by Munson et al., Anal. Biochem. 107: 220 (1980). After determining the specificity, affinity, and reactivity of the antibody produced by the hybridoma, the cell strain of interest can be subcloned by the standard limiting dilution method described in Goding, Monoclonal Antibodies: Principles and Practice, pp. 59-103, Academic Press, 1996. A suitable culture medium may be DMEM or RPMI-1640 or the like. In addition, hybridoma cells can also be grown in animals in the form of ascites tumors. Utilizing traditional immunoglobulin purification methods, such as protein A agarose gel, hydroxyapatite chromatography, gel electrophoresis, dialysis or affinity chromatography, the monoclonal antibodies secreted by the subcloned cells can be isolated from the cell culture medium, ascites or serum.

Monoclonal antibodies can also be obtained by genetic engineering recombinant techniques. A DNA molecule encoding the heavy chain and light chain genes of a monoclonal antibody can be isolated from a hybridoma cell by PCR amplification using a nucleic acid primer that specifically binds to the monoclonal antibody heavy chain and light chain genes. The obtained DNA molecule is inserted into an expression vector, and then transfected into a host cell (such as E. coli cells, COS cells, CHO cells, or other myeloma cells that do not produce immunoglobulin), and cultured under appropriate conditions, thereby obtaining the desired recombinant antibody.

The antibody can be purified by well-known techniques, for example, affinity chromatography using Protein A or Protein G. Subsequently or alternatively, the specific antigen (the target molecule recognized by the antibody) or its antigenic epitope can be immobilized on a column and the immunospecific antibody can be purified by immunoaffinity chromatography. Purification of immunoglobulins can be found, for example, in D. Wilkinson (The Scientist, published by The Scientist, Inc., Philadelphia Pa., Vol. 14, No. 8 (Apr. 17, 2000), pp. 25-28).

As used herein, the term "murine antibody" refers to an antibody that is prepared by fusing B cells of immunized mice with myeloma cells, selecting murine hybrid fusion cells that can proliferate indefinitely and secrete the antibody, followed by screening, antibody preparation and antibody purification; or an antibody that is secreted by plasma cells which is formed by differentiation and proliferation of B cells after antigen invades the mouse body. For the antibody produced under the stimulation of specific antigen, the production of antibody is due to the interaction of various immune cells caused by the antigen invading the human body, resulting in differentiation and proliferation of B cells into plasma cells, which can produce and secrete the antibody.

As used herein, the term "Chimeric antibody" refers to an antibody in which a portion of the light or/and heavy chain thereof is derived from one antibody (which may be derived from a specific species or belong to a certain specific antibody class or subclass), and another portion of the light chain or/and heavy chain is derived from another antibody (which may be derived from the same or different species or belong to the same or different antibody class or subclass), nonetheless, it still retains binding activity to the antigen of interest (U.S. Pat. No. 4,816,567 to Cabilly et al.; Morrison et al., Proc. Natl. Acad. Sci. USA, 81:6851 6855 (1984)). For example, the term "chimeric antibody" can include an antibody (e.g., a human-murine chimeric antibody) wherein the heavy and light chain variable regions of the antibody are derived from a first antibody (e.g., a murine antibody), while the heavy chain and light chain variable regions of the antibody are derived from a second antibody (e.g., a human antibody).

As used herein, the term "humanized antibody" refers to a genetically engineered non-human antibody whose amino acid sequence has been modified to increase homology to the sequence of a human antibody. Generally, all or part of the CDR regions of a humanized antibody are derived from a non-human antibody (donor antibody), and all or part of the non-CDR regions (e.g., variable region FRs and/or constant region) are derived from a human immunoglobulin (receptor antibody). Humanized antibodies typically retain the desired properties of the donor antibody, including, but not limited to, antigen specificity, affinity, reactivity, ability to increase immune cell activity, ability to enhance an immune response, and the like. A donor antibody can be an antibody from mouse, rat, rabbit, or non-human primate (e.g., cynomolgus) having desirable properties (e.g., antigen specificity, affinity, reactivity, ability to increase immune cell activity and/or enhance immune response).

Humanized antibody can not only retain the expected properties of non-human donor antibody (e.g., murine antibody), but also effectively reduce the immunogenicity of non-human donor antibody (e.g., murine antibody) in a human subject, and thus is particularly advantageous. However, due to the matching problem between the CDR of donor antibody and the FR of receptor antibody, the expected properties of humanized antibody (e.g., antigen specificity, affinity, reactivity, ability to improve immune cell activity, and/or ability to enhance immune response) are generally lower than that of the non-human donor antibody (e.g., murine antibody).

Therefore, although researchers in the field have carried out in-depth research on the humanization of antibodies and have made some progresses (see, for example, Jones et al., Nature, 321:522 525 (1986); Reichmann et al., Nature, 332: 323 329 (1988); Presta, Curr. Op. Struct. Biol., 2:593 596 (1992); and Clark, Immunol. Today 21: 397 402 (2000)), the prior art does not provide detailed guidance on how to fully humanize donor antibody so that the humanized antibody produced not only has the highest degree of humanization, but also retains the expected properties of the donor antibody as much as possible. Technicians need to perform exploration, investigation and modification for a specific donor antibody, and pay a lot of creative work to obtain a humanized antibody that not only has a high degree of humanization (for example, a humanization degree of at least 75%, at least 80%, at least 85%, at least 90%, at least 91%, at least 92%, at least 93%, at least 94%, at least 95%, at least 96%, at least 97%, at least 98%, at least 99%), but also retains the expected properties of the specific donor antibody.

In the present invention, in order to make the humanized antibody retain the properties (including, for example, antigen specificity, affinity, reactivity, ability to improve immune cell activity and/or ability to enhance immune response) of the donor antibody as much as possible, the framework region (FR) of the humanized antibody of the present invention may comprise both the amino acid residues of human receptor antibody and the amino acid residues of corresponding non-human donor antibody.

The chimeric antibody or humanized antibody of the present invention can be prepared based on the sequence of the murine monoclonal antibody prepared above. The DNA encoding the heavy and light chains can be obtained from the target murine hybridoma and engineered using standard molecular biology techniques to contain non-mouse (e.g., human) immunoglobulin sequences.

To prepare a chimeric antibody, a variable region of murine immunoglobulin can be linked to a constant region of human immunoglobulin using a method known in the art (see, for example, U.S. Pat. No. 4,816,567 to Cabilly et al.). For example, a DNA encoding VH is operably linked to another DNA molecule encoding heavy chain constant region so as to obtain a full-length heavy chain gene. The sequence of human heavy chain constant region gene is known in the art (see, for example, Kabat, E A et al. (1991) Sequences of Proteins of Immunological Interest, Fifth Edition, U.S. Department of Health and Human Services, NIH Publication No. 91-3242), a DNA fragment containing these regions can be obtained by standard PCR amplification. The heavy chain constant region may be an IgG1, IgG2, IgG3, IgG4, IgA, IgE, IgM or IgD constant region, but is generally preferably an IgG1 or IgG4 constant region. For example, a DNA encoding VL is operably linked to another DNA molecule encoding light chain constant region CL so as to obtain a full-length light chain gene (as well as a Fab light chain gene). The sequence of human light chain constant region gene is known in the art (see, for example, Kabat, E A et al. (1991) Sequences of Proteins of Immunological Interest, Fifth Edition, US Department of Health and Human Services, NIH Publication No. 91-3242), a DNA fragment containing these regions can be obtained by standard PCR amplification. The light chain constant region may be a κ or λ constant region, but is generally preferably a κ constant region.

To prepare a humanized antibody, murine CDR regions can be grafted onto a human framework sequence by using any methods known in the art (see U.S. Pat. No. 5,225,539 to Winter; U.S. Pat. Nos. 5,530,101, 5,585,089, 5,693,762, and 6,180,370 to Queen et al.; And Lo, Benny, KC, editor, in Antibody Engineering: Methods and Protocols, volume 248, Humana Press, New Jersey, 2004). Alternatively, a transgenic animal can also be used, which is capable of producing a complete human antibody library without producing an endogenous immunoglobulin after immunization. For example, it has been reported that the homozygous deletion of the antibody heavy chain joining region (JH) gene in chimeric and germ-line mutant mice results in complete inhibition of endogenous antibody production, and transfer of the human germ-line immunoglobulin gene array in such germ-line mutant mice will result in the production of human antibodies upon antigen challenge (see, for example, Jakobovits et al., 1993, Proc. Natl. Acad. Sci. USA 90: 2551; Jakobovits et al., 1993, Nature 362: 255-258; Bruggermann et al., 1993, Year in Immunology 7: 33; and Duchosal et al., 1992, Nature 355: 258). Non-limiting examples of the above-mentioned transgenic animal include HuMAb mice (Medarex, Inc.) which comprises human immunoglobulin gene miniloci encoding unrearranged human heavy chains (μ and γ) and κ light chain immunoglobulin sequences, and a targeted mutation that inactivates endogenous μ and κ chain loci (see, for example, Lonberg et al. (1994) Nature 368 (6474): 856-859); or "KM Mouse™" which carries a human heavy chain transgene and human light chain transchromosome (see: patent application WO02/43478). Other methods of humanizing antibodies include phage display technology (Hoogenboom et al., 1991, J. Mol. Biol. 227: 381; Marks et al., J. Mol. Biol. 1991, 222: 581-597; Vaughan et al., 1996, Nature Biotech 14: 309).

As used herein, the term "humanization degree" refers to an index used to evaluate the number of non-human amino acid residues in a humanized antibody. The humanization degree of a humanized antibody can be assessed, for example, by predicting the homology of the variable region sequence to the human V domain with the DomainGapAlign of IMGT web site.

As used herein, "homologous antibody" refers to a variant of an antibody, in which the amino acid sequences in the heavy and light chain variable regions contained therein are homologous to the amino acid sequence of the antibody or antigen-binding fragment thereof provided herein, and the variant retains the desired functional properties of the anti-CLDN18.2 antibody of the present invention.

Methods of sequence alignment for comparison are well known in the art. Various procedures and alignment algorithms are described in: Smith T F and Waterman M S, Adv. Appl. Math., 2:482, 1981; Higgins D G and Sharp P M, CABIOS 5:151, 1989. Altschul S F et al., Nature Genet., 6:119, 1994 provides detailed ideas for sequence alignment and homology calculations.

As used herein, the term "specific binding" refers to a non-random binding reaction between two molecules, such as a reaction between an antibody and an antigen to which it is directed. The strength or affinity of a specific binding interaction can be expressed in term of the equilibrium dissociation constant (KD) or half-maximum effect concentration (EC50) of the interaction.

The specific binding properties between two molecules can be determined using methods known in the art. One method involves measuring the rate of formation and dissociation of the antigen binding site/antigen complex. Both the "binding rate constant" (ka or kon) and the "dissociation rate constant" (kdis or koff) can be calculated from the concentration and the actual rate of association and dissociation (see Malmqvist M, Nature, 1993, 361: 186-187). The ratio of kdis/kon is equal to the dissociation constant KD (see Davies et al, Annual Rev Biochem, 1990; 59: 439-473). The KD, kon and kdis values can be measured in any effective way. In certain embodiments, the dissociation constant can be measured using bioluminescence interferometry (e.g., the ForteBio Octet method). In addition, the dissociation constant can be measured by surface plasmon resonance techniques (for example, Biacore) or Kinexa.

As used herein, the term "vector" refers to a nucleic acid vehicle into which a polynucleotide can be inserted. When a vector enables the expression of a protein encoded by an inserted polynucleotide, the vector is referred to as an expression vector. A vector can be introduced into a host cell by transformation, transduction or transfection, so that the genetic material elements carried by the vector can be expressed in the host cell. Vectors are well known to those skilled in the art and include, but are not limited to: plasmids; phagemids; cosmids; artificial chromosomes, such as yeast artificial chromosomes (YAC), bacterial artificial chromosomes (BAC) or P1-derived artificial chromosomes (PAC); bacteriophages such as λ phage or M13 phage and animal viruses. Animal viruses that can be used as vectors include, but are not limited to, retroviruses (including lentiviruses), adenoviruses, adeno-associated viruses, herpes viruses (e.g., herpes simplex virus), poxviruses, baculoviruses, papillomaviruses, papovavirus (e.g., SV40). A vector may comprise a variety of elements that control expression, including, but not limited to, promoter sequence, transcription initiation sequence, enhancer sequence, selection element, and reporter gene. In addition, the vector may comprise a replication initiation site.

Expression and cloning vectors contain a nucleic acid sequence that enables the vectors to replicate in one or more selected host cells. Generally, in cloning vectors, this sequence is one that enables the vector to replicate independently of the host chromosomal DNA, and includes an origin of replication or an autonomously replicating sequence. The term "expression vector" as used herein refers to a vector containing a recombinant polynucleotide, which comprises an expression control sequence operatively linked to the nucleotide sequence to be expressed. The expression vector contains sufficient cis-acting elements for expression; other elements for expression can be provided by host cells or in vitro expression systems. Expression vectors include all those known in the art, such as cosmids, plasmids (e.g., naked or contained in liposomes), and viruses (e.g., lentivirus, retrovirus, adenovirus, and adeno-associated virus).

As used herein, the term "host cell" refers to a cell into which a vector can be introduced, which includes, but is not limited to, prokaryotic cell such as *E. coli* or *Bacillus subtilis*, fungal cells such as yeast cells or *aspergillus*, insect cells such as S2 *drosophila* cells or Sf9, or animal cells such as fibroblast cells, CHO cells, COS cells, NSO cells, HeLa cells, BHK cells, HEK 293 cells, or human cells. In this context, host cells also include immune cells used to construct chimeric antigen receptor T cells (CAR-T), such as T lymphocytes, NK cells, etc.

As used herein, the term "identity" refers to the match degree between two polypeptides or between two nucleic acids. When two sequences for comparison have the same monomer sub-unit of base or amino acid at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by using a computer program such as Align program (DNAstar, Inc.) which is based on the method of Needleman, et al. (J. Mol. Biol. 48:443-453, 1970). The percent identity between two amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

As used herein, the term "conservative substitution" means an amino acid substitution that does not adversely affect or alter the expected properties of a protein/polypeptide comprising an amino acid sequence, and the antibody variant obtained by conservative substitution retains the biological activity of its original sequence, such as specifically binding to CLDN 18.2. For example, conservative substitutions can be introduced by standard techniques known in the art, such as site-directed mutagenesis and PCR-mediated mutagenesis. Conservative amino acid substitutions include substitutions wherein an amino acid residue is substituted with another amino acid residue having a similar side chain, for example, a residue physically or functionally similar (e.g., having similar size, shape, charge, chemical properties, including ability of forming a covalent bond or a hydrogen bond, etc.) to the corresponding amino acid residue. A family of amino acid residues having similar side chains has been defined in the art. These families include amino acids having basic side chains (e.g., lysine, arginine, and histidine), acidic side chains (e.g., aspartic acid, glutamic acid), uncharged polar side chains (e.g., glycine, asparagine, glutamine, serine, threonine, tyrosine, cysteine, tryptophan), non-polar side chains (e.g. alanine, valine, leucine, isoleucine, valine, phenylalanine, methionine), beta branch side chains (e.g., threonine, valine, isoleucine) and aromatic side chains (e.g., tyrosine, phenylalanine, tryptophan, histidine). Therefore, it is preferred to replace the corresponding amino acid residue with another amino acid residue from the same side chain family. Methods for identifying conservative substitutions of amino acids are well known in the art (see, for example, Brummell et al, Biochem. 32: 1180-1187 (1993); Kobayashi et al., Protein Eng. 12(10): 879-884 (1999); and Burks et al. Proc. Natl Acad. Set USA 94: 412-417 (1997), which is incorporated herein by reference).

The twenty conventional amino acids involved herein are expressed in routine manners. See, for example, Immunology-A Synthesis (2nd Edition, E. S. Golub and D. R. Gren, Eds., Sinauer Associates, Sunderland, Mass. (1991)), which is incorporated herein by reference. In the present disclosure, the terms "polypeptide" and "protein" have the same meaning and are used interchangeably. Also in the present disclosure, amino acids are generally represented by single letter and three letter abbreviations as known in the art. For example, alanine can be represented by A or Ala.

The term "pharmaceutically acceptable carrier and/or excipient" as used herein refers to a carrier and/or excipient that is pharmacologically and/or physiologically compatible with the subject and the active ingredient, which is well known in the art (see, for example, Remington's Pharmaceutical Sciences. Edited by Gennaro A R, 19th ed. Pennsylvania: Mack Publishing Company, 1995) and includes, but is not limited to, pH adjusting agents, surfactants, adjuvants, ionic strength enhancers, diluents, agents that maintain osmotic pressure, agents that delay absorption, preservatives. For example, pH adjusting agents include, but are not limited to, phosphate buffers. Surfactants include, but are not limited to, cationic, anionic or nonionic surfactants such as Tween-80. Ionic strength enhancers include, but are not limited to, sodium chloride. Preservatives include, but are not limited to, various antibacterial and antifungal agents, such as parabens, chlorobutanol, phenol, sorbic acid, and the like. Agents that maintain osmotic pressure include, but are not limited to, sugars, NaCl, and the like. Agents that delay absorption include, but are not limited to, monostearate and gelatin. Diluents include, but are not limited to, water, aqueous buffers (such as buffered saline), alcohols and polyols (such as glycerin), and the like. Preservatives include, but are not limited to, various antibacterial and antifungal agents, such as thimerosal, 2-phenoxyethanol, parabens, chlorobutanol, phenol, sorbic acid, and the like. Stabilizers have the meaning commonly understood by those skilled in the art which can stabilize the desired activity of the active ingredient in the drug, including but not limited to sodium glutamate, gelatin, SPGA, sugars (e.g., sorbitol, mannitol, starch, sucrose, lactose, dextran, or glucose), amino acids (such as glutamic acid, glycine), proteins (such as dried whey, albumin or casein) or degradation products thereof (such as lactalbumin hydrolysate).

As used herein, the term "treatment" refers to a clinical intervention in the process of trying to change a person or treating cells in which a disease is induced, which can be used for prevention or intervention in a clinical pathological process. The therapeutic effects include, but are not limited to, preventing the occurrence or recurrence of disease, reducing symptoms, reducing the direct or indirect pathological consequences of disease, preventing metastasis, slowing the progression of disease, improving or relieving condition, relieving or improving prognosis, etc.

As used herein, the term "prevention" refers to a method performed to prevent or delay the occurrence of a disease or disorder or symptom (e.g., a tumor, infection, or autoimmune disease) in a subject. As used herein, the term "treatment" refers to a method performed to obtain a beneficial or desired clinical result. For the purposes of the present invention, the beneficial or desired clinical result includes, but is not limited to, alleviating symptom, reducing the extent of disease, stabilizing (i.e., no longer exacerbating) the state of disease, delaying or slowing the development of disease, improving or alleviating the status of disease, and alleviating a symptom (either in part or in whole), either detectable or undetectable. In addition, the term "treatment" can also refer to prolonging survival time as compared to the expected survival time (if not receiving treatment).

As used herein, the term "subject" refers to a mammal, such as a primate mammal, such as a human. In certain embodiments, the subject (e.g., a human) suffers from tumor, infection or autoimmune disease, or is at risk of suffering from the aforementioned diseases.

As used herein, the term "effective amount" refers to an amount sufficient to obtain or at least partially obtain a desired effect. For example, an effective amount to prevent a disease (e.g., tumor, infection, or autoimmune disease) refers to an amount sufficient to prevent, stop or delay the occurrence of a disease (e.g., tumor, infection, or autoimmune disease); an effective amount for treating a disease refers to an amount sufficient to cure or at least partially prevent a disease and complications thereof in a patient who has already suffered from the disease. It is completely within the ability of those skilled in the art to determine such an effective amount. For example, the effective amount for a therapeutic use will depend on the severity of the disease to be treated, the overall state of the patient's own immune system, the patient's general conditions such as age, weight and gender, the manner in which the drug is administered, and other therapies administered simultaneously, etc..

As used herein, the term "immune cell" includes cells that have a hematopoietic origin and play a role in immune response, for example, lymphocytes, such as B cells and T cells; natural killer cells; myeloid cells, such as monocytes, macrophages, eosinophils, mast cells, basophils and granulocytes.

As used herein, the term "immune response" refers to an effect of immune cells (e.g., lymphocytes, antigen-presenting cells, phagocytes, or granulocytes) and soluble macromolecules (including antibodies, cytokines, and complements) produced by the immune cells or liver, which leads to selective damage or destruction of invasive pathogens, cells or tissues infected with pathogens, cancer cells, or normal human cells or tissues in the context of autoimmune or pathological inflammation, or removal of them from the body. In the present invention, the term "antigen-specific T cell response" refers to an immune response produced by a T cell, which is generated when the T cell is stimulated by the T cell specific antigen. Non-limiting examples of response produced by T cell upon antigen-specific stimulation include the proliferation of T cell and the production of cytokine such as IL-2.

As used herein, the term "effector function" refers to those biological activities attributable to the Fc region of an antibody (Fc region of a natural sequence or an amino acid sequence variant), which varies as the isotype of an antibody. Examples of antibody effector functions include, but are not limited to, Fc receptor binding affinity, antibody-dependent cell-mediated cytotoxicity (ADCC), complement dependent cytotoxicity (CDC), antibody-dependent cellular phagocytosis (ADCP), downregulation of cell surface receptors (e.g., B cell receptors), B cell activation, cytokine secretion, half-life/clearance of antibodies and antigen-antibody complexes, and the like. Methods for altering the effector function of an antibody are known in the art, for example by introducing a mutation in the Fc region.

As used herein, the term "antibody-dependent cell-mediated cytotoxicity (ADCC)" refers to a form of cytotoxicity, in which cytotoxic effector cells specifically bind to the target cells to which the antigen is attached, through the binding of Ig to an Fc receptor (FcR) presented on cytotoxic cells (e.g., natural killer (NK) cells, neutrophils or macrophages), and then kills the target cells by secreting cytotoxins. Methods for detecting ADCC activity of an antibody are known in the art and can be evaluated, for example, by measuring the binding activity between an antibody to be tested and an Fc receptor (e.g., CD16a).

As used herein, the term "complement dependent cytotoxicity (CDC)" refers to a form of cytotoxicity in which the complement cascade is activated by the binding of complement component Cq to Fc of an antibody. Methods for detecting the CDC activity of an antibody are known in the art and can be evaluated, for example, by measuring the binding activity between an antibody to be tested and an Fc receptor (e.g., C1q).

The terms "cancer" and "tumor" are used interchangeably and refer to a large group of diseases characterized by the uncontrolled growth of abnormal cells in the body. Unregulated cell division may lead to the formation of malignant tumors or cells that invade adjacent tissues, and may metastasize to distant parts of the body through the lymphatic system or bloodstream. Cancers include benign and malignant cancers as well as dormant tumors or micrometastasis. Cancers also include hematological malignancies.

The term "hematological malignancy" includes lymphoma, leukemia, myeloma or lymphoid malignancies, as well as spleen cancer and lymph node tumors. Exemplary lymphomas include B-cell lymphoma and T-cell lymphoma. B-cell lymphoma includes, for example, Hodgkin's lymphoma. T cell lymphoma includes, for example, skin T cell lymphoma. Hematological malignancies also include leukemia, such as secondary leukemia or acute lymphocytic leukemia. Hematological malignancies also include myeloma (e.g., multiple myeloma) and other hematological and/or B cell or T cell related cancers.

As used herein, the term "pharmaceutically acceptable" means that when a molecular itself, molecular fragment or composition is suitably administered to an animal or a human, it does not produce an adverse, allergic or other untoward reaction. Specific examples of some substances which can be used as a pharmaceutically acceptable carrier or a component thereof include sugars such as lactose, starch, cellulose and derivatives thereof, vegetable oils, gelatin, polyols such as propylene glycol, alginic acid and the like.

In this context, a combination therapy includes the use of combination of the anti-CLDN18.2 antibody or antigen-binding fragment thereof covered by the present invention with one or more additional active therapeutic agents (e.g., chemotherapeutics) or other preventive or therapeutic modalities (e.g., radiotherapy).

Exemplary anticancer agents for the second therapy may include chemotherapeutic agents (e.g., mitotic inhibitors), alkylating agents (e.g., Nitrogen Mustard), antimetabolites (e.g., folate analogs), natural products (e.g., *Vinca* Alkaloid), various reagents (e.g., platinum coordination complexes), hormones and antagonists (e.g., adrenal corticosteroids), immunomodulators (e.g., Bropirimine, Upjohn), etc. Other anti-cancer treatments include other antibodies that specifically target cancer cells.

In this type of combination therapy, various active agents often have different complementary mechanisms of action, and the combination therapy may result in a synergistic effect. The combination therapy includes therapeutic agents that affect the immune response (e.g., enhancing or activating the response) and therapeutic agents that affect (e.g., inhibiting or killing) tumor/cancer cells. The combination therapy can reduce the possibility of occurrence of drug-resistant cancer cells. The combination therapy may allow the dosage of one or more of the agents to be reduced so as to reduce or eliminate an adverse effect associated with one or more of the agents. Such combination therapy may have a synergistic therapeutic or preventive effect on a potential disease, disorder or condition.

In this context, the "combination" includes therapies that can be administered separately, such as separately formulated for separate administration (for example, can be provided in a kit), and therapies that can be administered together as a single formulation (i.e., "co-formulation"). In certain embodiments, the anti-CLDN18.2 antibodies or antigen-binding fragments thereof of the present invention can be administered sequentially. In other embodiments, the anti-CLDN18.2 antibodies or antigen-binding fragments thereof can be administered simultaneously. The anti-CLDN18.2 antibodies or antigen-binding fragments thereof of the present invention can be used in any combination with at least one other (active) agent.

In this context, "Claudin 18.2 positive" is obtained by immunohistochemistry and evaluation of staining intensity by a professional clinician pathologist. "HER2 negative", includes IHC 1+, or IHC 2+/FISH negative, as well as the range of IHC 0 to 1+ and IHC 1+ to 2+.

The embodiments of the present invention will be described in detail below with reference to the accompanying drawings and examples. However, those skilled in the art will understand that the following drawings and examples are only used to illustrate the present invention, but not to limit the scope of the present invention. According to the accompanying drawings and the following detailed description of preferred embodiments, various objects and advantageous aspects of the present invention will become implementable for those skilled in the art.

SEQUENCE INFORMATION

Figure 1A:
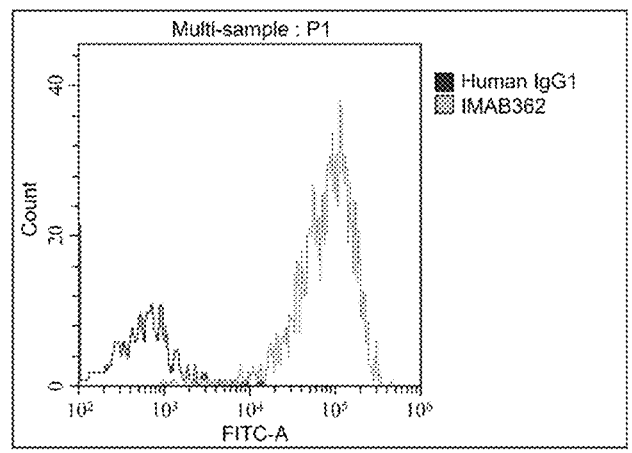
FIG. 1A: Detection of the monoclonal stable cell line of HEK293T-Claudin18.2 by flow cytometry.
Figure 1B:
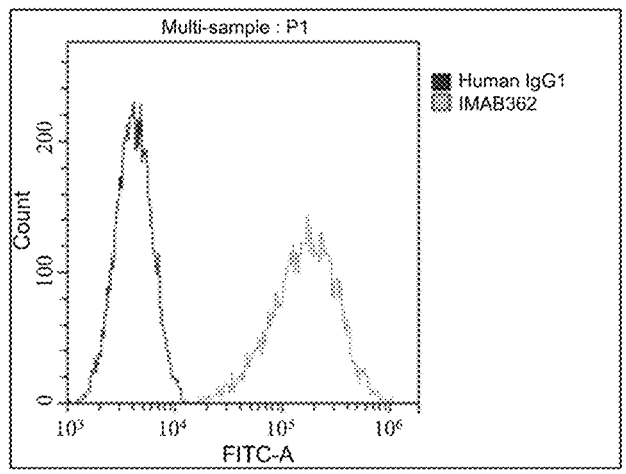
FIG. 1B: Detection of the monoclonal stable cell line of L929-Claudin18.2 by flow cytometry.
Figure 1C:
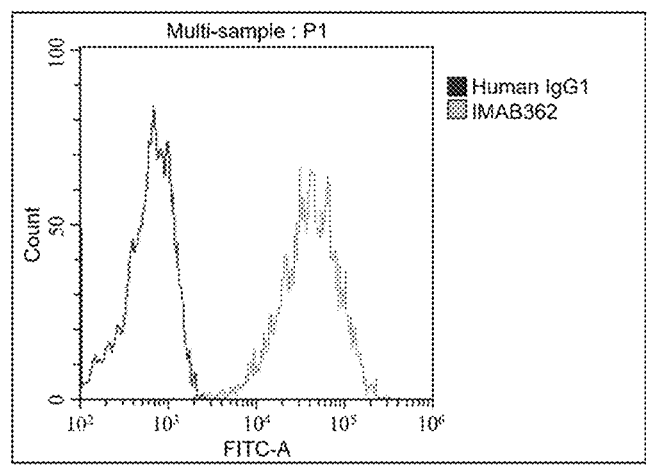
FIG. 1C: Detection of the monoclonal stable cell line of KATOIII-Claudin18.2 by flow cytometry.
Figure 1D:
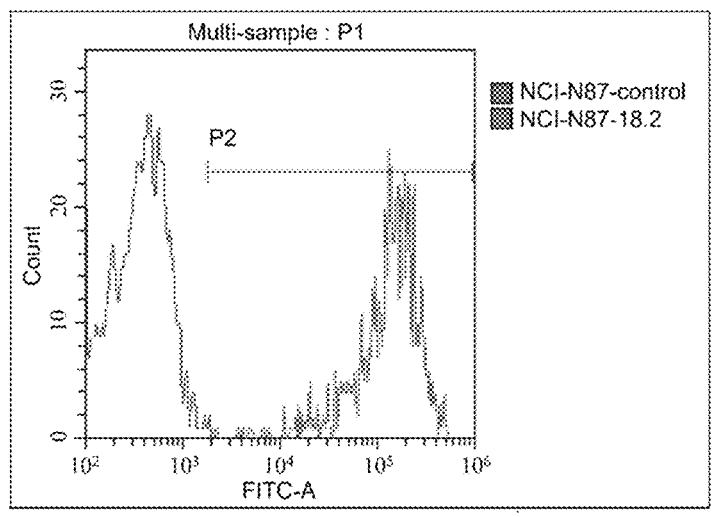
FIG. 1D: Detection of the monoclonal stable cell line of NCI-N87-Claudin18.2 by flow cytometry.

The sequence information involved in the invention is provided in the table below.

| SEQ ID NO | Description |
|---|---|
| 1 | heavy chain variable region of mouse antibody 1E9.2 |
| 2 | light chain variable region of mouse antibody 1E9.2 |
| 3 | heavy chain variable region of mouse antibody 2C6.9 |
| 4 | light chain variable region of mouse antibody 2C6.9 |
| 5 | IMGT 1E9.2 CDR-H1 |
| 6 | IMGT 1E9.2 CDR-H2 |
| 7 | IMGT 1E9.2 CDR-H3 |
| 8 | IMGT 1E9.2 CDR-L1 |
| 9 | IMGT 1E9.2 CDR-L2 |
| 10 | IMGT 1E9.2 CDR-L3 |
| 11 | IMGT 2C6.9/2C6.9-hz11/2C6.9-hz21 CDR-H1 |
| 12 | IMGT 2C6.9/2C6.9-hz11 CDR-H2 |
| 13 | IMGT 2C6.9/2C6.9-hz11/2C6.9-hz21 CDR-H3 |
| 14 | IMGT 2C6.9/2C6.9-hz11/2C6.9-hz21 CDR-L1 |
| 15 | IMGT 2C6.9/2C6.9-hz11/2C6.9-hz21 CDR-L2 |
| 16 | IMGT 2C6.9/2C6.9-hz11/2C6.9-hz21 CDR-L3 |
| 17 | AbM 1E9.2 CDR-H1 |
| 18 | AbM 1E9.2 CDR-H2 |
| 19 | AbM 1E9.2 CDR-H3 |
| 20 | AbM 1E9.2 CDR-L1 |
| 21 | AbM 1E9.2 CDR-L2 |
| 22 | AbM 1E9.2 CDR-L3 |
| 23 | AbM 2C6.9/2C6.9-hz11/2C6.9-hz21 CDR-H1 |
| 24 | AbM 2C6.9/2C6.9-hz11 CDR-H2 |
| 25 | AbM 2C6.9/2C6.9-hz11/2C6.9-hz21 CDR-H3 |
| 26 | AbM 2C6.9/2C6.9-hz11/2C6.9-hz21 CDR-L1 |
| 27 | AbM 2C6.9/2C6.9-hz11/2C6.9-hz21 CDR-L2 |
| 28 | AbM 2C6.9/2C6.9-hz11/2C6.9-hz21 CDR-L3 |
| 29 | heavy chain variable region of humanized antibody 1E9.2hz11/1E9.2hz12/1E9.2hz13/1E9.2hz14/1E9.2hz15/1E9.2hz17 |
| 30 | heavy chain variable region of humanized antibody 1E9.2hz21 |
| 31 | heavy chain variable region of humanized antibody 1E9.2hz31 |
| 32 | heavy chain variable region of humanized antibody 1E9.2hz41 |
| 33 | light chain variable region of humanized antibody 1E9.2hz11/1E9.2hz21/1E9.2hz31/1E9.2hz41 |
| 34 | light chain variable region of humanized antibody 1E9.2hz12 |
| 35 | light chain variable region of humanized antibody 1E9.2hz13 |

-continued

| SEQ ID NO | Description |
|---|---|
| 36 | light chain variable region of humanized antibody 1E9.2hz14 |
| 37 | light chain variable region of humanized antibody 1E9.2hz15 |
| 38 | light chain variable region of humanized antibody 1E9.2hz17 |
| 39 | Heavy chain variable region of humanized antibody 2C6.9hz11 |
| 40 | heavy chain variable region of humanized antibody 2C6.9hz21 |
| 41 | light chain variable region of humanized antibody 2C6.9hz11/2C6.9hz21 |
| 42 | human IgG1 heavy chain constant region |
| 43 | human k light chain constant region |
| 44 | heavy chain variable region sequence of mouse antibody 19H11.6 |
| 45 | light chain variable region sequence of mouse antibody 19H11.6 |
| 46 | heavy chain variable region sequence of mouse antibody 16A9.11 |
| 47 | light chain variable region sequence of mouse antibody 16A9.11 |
| 48 | heavy chain variable region sequence of mouse antibody 9C8.1 |
| 49 | light chain variable region sequence of mouse antibody 9C8.1 |
| 50 | heavy chain variable region sequence of mouse antibody 6B9.22 |
| 51 | light chain variable region sequence of mouse antibody 6B9.22 |
| 52 | heavy chain variable region sequence of mouse antibody 19G10.14 |
| 53 | light chain variable region sequence of mouse antibody 19G10.14 |
| 54 | heavy chain variable region sequence of mouse antibody 1E9.2 |
| 55 | light chain variable region sequence of mouse antibody 1E9.2 |
| 56 | heavy chain variable region sequence of mouse antibody 2C6.9 |
| 57 | light chain variable region sequence of mouse antibody 2C6.9 |
| 58 | AbM 19H11.6/16A9.11 CDR-H1 |
| 59 | AbM 9C8.1 CDR-H1 |
| 60 | AbM 6B9.22 CDR-H1 |
| 61 | AbM 19G10.14 CDR-H1 |
| 62 | AbM 19H11.6CDR-H2 |
| 63 | AbM 16A9.11 CDR-H2 |
| 64 | AbM 9C8.1 CDR-H2 |
| 65 | AbM 6B9.22 CDR-H2 |
| 66 | AbM 19G10.14 CDR-H2 |
| 67 | AbM 19H11.6 CDR-H3 |
| 68 | AbM 16A9.11 CDR-H3 |
| 69 | AbM 9C8.1 CDR-H3 |
| 70 | AbM 6B9.22 CDR-H3 |
| 71 | AbM 19G10.14 CDR-H3 |
| 72 | AbM 19H11.6/16A9.11/9C8.1/6B9.22 CDR-L1 |
| 73 | AbM 19G10.14 CDR-L1 |
| 74 | AbM 19H11.6/16A9.11 CDR-L2 |
| 75 | AbM 9C8.1 CDR-L2 |
| 76 | AbM 6B9.22 CDR-L2 |
| 77 | AbM 19G10.14 CDR-L2 |
| 78 | AbM 19H11.6/16A9.11 CDR-L3 |
| 79 | AbM 9C8.1/6B9.22 CDR-L3 |
| 80 | AbM 19G10.14 CDR-L3 |
| 81 | IMGT 19H11.6/16A9.11 CDR-H1 |
| 82 | IMGT 19H11.6CDR-H2 |
| 83 | IMGT 19H11.6 CDR-H3 |
| 84 | IMGT 16A9.11 CDR-H2 |

-continued

| SEQ ID NO | Description |
|---|---|
| 85 | IMGT 16A9.11 CDR-H3 |
| 86 | IMGT 9C8.1 CDR-H1 |
| 87 | IMGT 9C8.1 CDR-H2 |
| 88 | IMGT 9C8.1 CDR-H3 |
| 89 | IMGT 6B9.22 CDR-H1 |
| 90 | IMGT 6B9.22 CDR-H2 |
| 91 | IMGT 6B9.22 CDR-H3 |
| 92 | IMGT 19G10.14 CDR-H1 |
| 93 | IMGT 19G10.14 CDR-H2 |
| 94 | IMGT 19G10.14 CDR-H3 |
| 95 | IMGT 19H11.6/16A9.11/9C8.1/6B9.22/19G10.14 CDR-L1 |
| 96 | IMGT 19H11.6/16A9.11 CDR-L2 |
| 97 | IMGT 19H11.6/16A9.11 CDR-L3 |
| 98 | IMGT 9C8.1/6B9.22 CDR-L2 |
| 99 | IMGT 9C8.1/6B9.22 CDR-L3 |
| 100 | IMGT 19G10.14 CDR-L2 |
| 101 | IMGT 19G10.14 CDR-L3 |
| 102 | heavy chain amino acid sequence of humanized antibody 1E9.2 hz11 |
| 103 | light chain amino acid sequence of humanized antibody 1E9.2 hz11 |
| 104 | heavy chain nucleotide sequence of humanized antibody 1E9.2 hz11 |
| 105 | light chain nucleotide sequence of humanized antibody 1E9.2 hz11 |
| 106 | heavy chain amino acid sequence of humanized antibody 2C6.9 hz21 |
| 107 | light chain amino acid sequence of humanized antibody 2C6.9 hz21 |
| 108 | heavy chain nucleotide sequence of humanized antibody 2C6.9 hz21 |
| 109 | light chain nucleotide sequence of humanized antibody 2C6.9 hz21 |
| 110 | IMGT 2C6.9-hz21 CDR-H2 |
| 111 | AbM 2C6.9-hz21 CDR-H2 |

EXAMPLES

The invention will now be described with reference to the following examples, which are intended to illustrate, but not to limit the invention.

Unless otherwise specified, the molecular biology experimental methods and immunoassays used in the present invention are generally referred to J. Sambrook et al., Molecular Cloning: A Laboratory Manual, 2nd Edition, Cold Spring Harbor Laboratory Press, 1989, and F. M. Ausubel et al., Short Protocols in Molecular Biology, 3rd Edition, John Wiley & Sons, Inc., 1995. It will be understood by a person skilled in the art that the examples are given for the purpose of illustration and are not to be construed to limit the scope of the present invention.

Example 1. Construction and Identification of Human Claudin18.2 and Human Claudin 18.1 Overexpression Cell Lines 1.1 Construction of Human Claudin18.2 and Human Claudin18.1 Overexpression Cell Lines To determine the specificity and function of anti-human Claudin18.2 antibody, the complete coding sequences of human Claudin18.2 (Gene accession number: NM_001002026.2, synthesized by Nanjing Genscript Biotech Corporation) and human Claudin18.1 (Gene accession number: NM_016369.3, synthesized by Nanjing Genscript Biotech Corporation) were cloned into lentivirus vector pLVX-IRES-puro and the viruses were prepared by lentivirus packaging system according to the published method (Mohammadi Z etl., Mol Biotechnol. 2015 September; 57(9):793-800.). The viruses obtained were used to infect HEK293T, L929, KATOIII and NCI-N87 cells. Monoclonal stable cell lines of HEK293T-Claudin 18.1, HEK293T-Claudin 18.2, L929-Claudin 18.2, KATOIII-Claudin 18.2, and NCI-N87-Claudin 18.2 were obtained by puromycin screening and single clone selection. BaF/3 cells (DSMZ, Cat #ACC300) were transfected with plasmids coding human Claudin18.2 or human Claudin18.1 using 4D-Nucleofector X transfection kit (Lonza, Cat #V4XC-3012). 48h after transfection, cells were screened by addition of 1.25 mg/mL hygromycin (Thermo Fisher Sci. Cat #10687010). Single clones were selected 12 days later, thereby obtaining monoclonal cell lines BaF/3-Claud18.1 and BaF/3-Claud18.2.

Figure 1E:
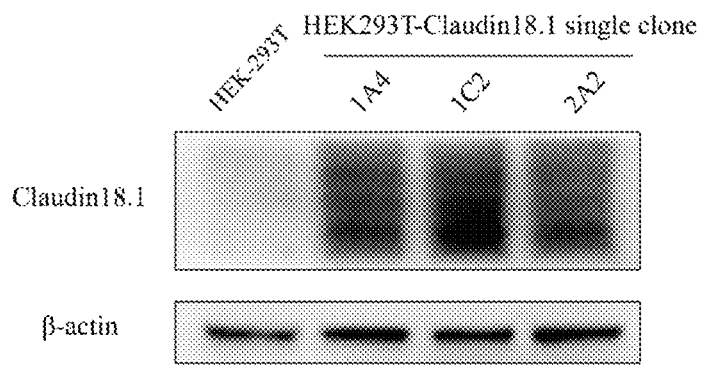
FIG. 1E: Detection of the monoclonal stable cell line of HEK293T-Claudin18.1 by Western blot.

1.2 Detection of Human Claudin18.2 and Human Claudin18.1 Overexpression Cell Lines Western Blot was used to detect HEK293T-Claudin 18.1 (Detection Antibody: Proteintech, 66167-1-Ig) and FACS was used to detect other cell lines (Flow cytometer: Beckman, CytoFlex; Detection Antibody: IMAB362, of which the sequences are from patent: CN 101312989 B). As shown in FIGS. 1A-1D, FACS results demonstrated that HEK293T-Claudin 18.2, L929—Claudin 18.2, KATOIII-Claudin 18.2 and NCI-N87—Claudin 18.2 monoclonal cell lines with high positive rate (close to 100%) and good homogeneity were obtained and were used in the following experiments. Western blot results (FIG. 1E) demonstrated that the three stable cell lines of HEK293T-Claudin 18.1 all overexpressed human Claudin 18.1. The single clone of HEK293T-Claudin 18.1-1C2 showed higher expression level among them and was used in the following experiments.

Example 2. Preparation of Mouse Anti-Human Claudin18.2 Monoclonal Antibodies

DNA/cell immunization was performed in wild type mice to generate mouse anti-human Claudin 18.2 monoclonal antibodies. Each Balb/c mouse was injected with 100 μg plasmid containing the complete coding sequence of human Claudin 18.2 through tail vein. After the fourth and sixth immunizations, serum titers were determined by FACS. Mice with high serum titers were boosted with BaF/3-Claudin18.2 overexpression cell lines 3-5 days prior to fusion. PEG mediated fusion of mouse splenocytes and mouse myeloma cell line Sp2/0 (ATCC, Cat #CRL-1581) was performed with standard fusion protocol, followed by HAT selection. FACS screening was carried out 10-14 days after fusion.

Supernatants of about 6000 hybridomas were screened using flow cytometry (available from Sartorius, as Model iQue Screener Plus) and 43 positive hybridomas binding HEK293T-Claudin18.2 cell line were obtained and subcloned. 14 hybridomas which specifically bound to human Claudin18.2 but not to human Claudin18.1 were selected by FACS using HEK293T-Claudin18.2 and HEK293T-Claudin18.1 cell lines. Single clones were obtained by limited dilution and subclone selection.

Human gastric cancer cell line NUGC4 (purchased from Japan JCRB cell bank, catalog number: JCRB0834) expresses Claudin18.2 endogenously and is widely used to evaluate the binding between antibodies and endogenous Claudin18.2 and develop functional assays. NUGC4 cells were used to evaluate the candidate clones and 7 sub-clones were finally selected, which are named 1E9.2, 2C6.9, 6B9.22, 9C8.1, 16A9.11, 19G10.14 and 19H11.6 respectively.

Example 3. Determination of the Affinity of Mouse Anti-Human Claudin18.2 Antibodies The affinity of the candidates to Claudin18.2 was measured using FACS. Single hybridoma clone 1E9.2, 2C6.9, 6B9.22, 9C8.1, 16A9.11, 19G10.14 and 19H11.6 were cultured in serum-free medium and mouse antibodies were purified from 100 mL supernatant by protein A chromatography (MabSelect SuRe, GE). Ba/F3-Claudin18.1 and Ba/F3-Claudin18.2 cells were incubated with the purified mouse antibodies at various concentrations on ice for 30 min and mouse IgG was used as negative control (Thermo Fisher, Cat: 31903), followed by washing with FACS buffer (PBS+2% FBS) twice. The cells were then incubated with a fluorescent goat-anti-mouse secondary antibody (Jackson ImmunoResearch, Cat: 115-605-071) on ice for 30 min before FACS analysis.

Figure 2A:
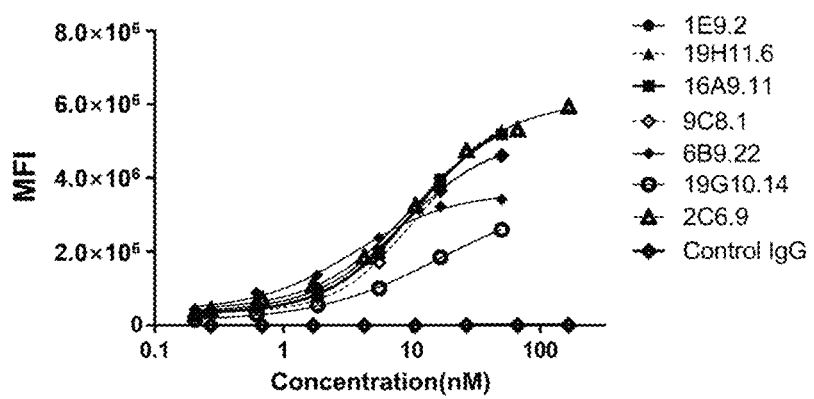
FIG. 2A: Determination of the affinity of mouse anti-human Claudin18.2 antibodies binding to Ba/F3-Claudin 18.2 cells.
Figure 2B:
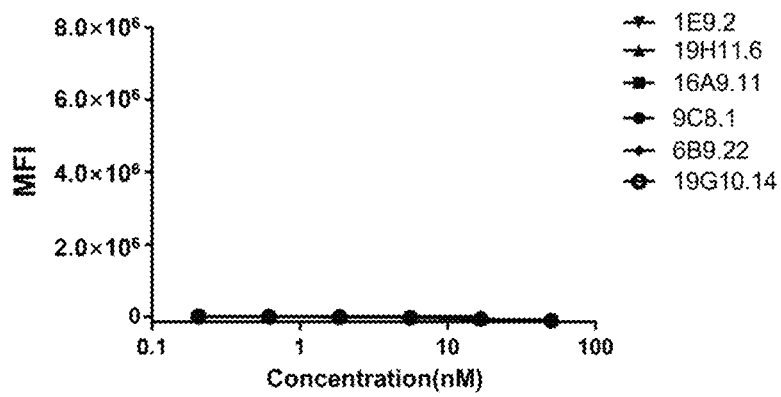
FIG. 2B: Determination of the affinity of mouse anti-human Claudin18.2 antibodies binding to Ba/F3-Claudin 18.1 cells.

As shown in FIGS. 2A-2B, all the seven mouse anti-human Claudin18.2 antibodies could specifically recognize human Claudin18.2 but not human Claudin18.1. Also, as shown in Table 1, the seven mouse anti-human Claudin18.2 antibodies show high affinity to Ba/F3-Claudin18.2 cells, with EC50 between 3-20 nM.

TABLE 1

Determination of the affinity of mouse anti-human Claudin 18.2 antibodies to Ba/F3-Claudin 18.2 cells

| Clone Number | EC50 (nM) | Max MFI* ($\times 10^6$) |
| --- | --- | --- |
| 1E9.2 | 8.506 | 5.085 |
| 19H11.6 | 10.94 | 6.008 |
| 16A9.11 | 10.2 | 5.815 |
| 9C8.1 | 9.399 | 4.969 |
| 6B9.22 | 3.64 | 3.624 |
| 19G10.14 | 16.27 | 3.501 |
| 2C6.9 | 10.57 | 6.111 |
| Control IgG | No binding | No binding |

*Max MFI is Max Mean Fluorescence Intensity

Example 4. Identification of the Subtype of Mouse Anti-Human Claudin18.2 Monoclonal Antibody and Amplification of Variable Regions In order to identify the antibody subtype of the candidate hybridoma clones, Pierce Rapid Isotyping kit (Thermo Fisher Sci. Cat #26179) was used to identify the antibody subtype of the seven candidate clones. The results showed that all candidates have IgG1 heavy chain and Kappa light chain.

Hybridoma cells were expanded and around 8000 cells were harvested and lysed. The first cDNA chain was synthesized by cDNA reverse transcription kit (Thermo Fisher Sci. Cat #18080-200). VH and VK (VL Kappa) genes were amplified by PCR from the cDNA using primers. The PCR products were purified by DNA purification kit (Qiagen, Cat #28104) and ligated to TOPO vector (Thermo Fisher Sci. Cat #K457540). About twelve clones were picked from each ligation reaction and sequenced. The sequences were then analyzed by Vector NTI 11.5 (Thermo Fisher Sci.) and Sequencer 5.4.6 (Genecodes). The variable region and CDR sequences of mouse anti-human Claudin18.2 antibody were shown in Table 2.

TABLE 2

The variable region and CDR amino acid sequences of mouse anti-human Claudin18.2 antibody s

| Clone Number | Heavy chain variable region (SEQ ID NO:) | Light chain variable region (SEQ ID NO:) | Definition mode | Heavy chain CDR1 (SEQ ID NO:) | Heavy chain CDR2 (SEQ ID NO:) | Heavy chain CDR3 (SEQ ID NO:) | Light chain CDR1 (SEQ ID NO:) | Light chain CDR2 (SEQ ID NO:) | Light chain CDR3 (SEQ ID NO:) |
|---|---|---|---|---|---|---|---|---|---|
| 1E9.2 | 1 | 2 | IMGT | 5 | 6 | 7 | 8 | 9 | 10 |
|  |  |  | AbM | 17 | 18 | 19 | 20 | 21 | 22 |
| 2C6.9 | 3 | 4 | IMGT | 11 | 12 | 13 | 14 | 15 | 16 |
|  |  |  | AbM | 23 | 24 | 25 | 26 | 27 | 28 |
| 19H11.6 | 44 | 45 | IMGT | 81 | 82 | 83 | 95 | 96 | 97 |
|  |  |  | AbM | 58 | 62 | 67 | 72 | 74 | 78 |
| 16A9.11 | 46 | 47 | IMGT | 81 | 84 | 85 | 95 | 96 | 97 |
|  |  |  | AbM | 58 | 63 | 68 | 72 | 74 | 78 |
| 9C8.1 | 48 | 49 | IMGT | 86 | 87 | 88 | 95 | 98 | 99 |
|  |  |  | AbM | 59 | 64 | 69 | 72 | 75 | 79 |
| 6B9.22 | 50 | 51 | IMGT | 89 | 90 | 91 | 95 | 98 | 99 |
|  |  |  | AbM | 60 | 65 | 70 | 72 | 76 | 79 |
| 19G10.14 | 52 | 53 | IMGT | 92 | 93 | 94 | 95 | 100 | 101 |
|  |  |  | AbM | 61 | 66 | 71 | 73 | 77 | 80 |

Example 5. Determination of the Affinity of Anti-Human Claudin18.2 Chimeric Antibodies The amino acid sequence of the light chain variable region of 1E9.2, 2C6.9, 6B9.22, 9C8.1, 16A9.11, 19G10.14 or 19H11.6 was linked to the amino acid sequence of the light chain constant region κ (SEQ ID NO: 43) respectively; the amino acid sequence of the heavy chain variable region was linked to the amino acid sequence of IgG1 heavy chain constant region (SEQ ID NO: 42) respectively, to construct the chimeric antibody. Codon optimized cDNA was synthesized and cloned to pcDNA3.4 (synthesized by Nanjing Genscript Biotech Corporation). The pcDNA3.4 plasmids coding the light chain and heavy chain of each antibody were co-transfected to Expi293F cells (purchased from Thermo Fisher). The antibodies were purified from culture supernatant by protein A (MabSelect SuRe, GE). And the purified chimeric antibodies were named 1E9.2-hz00, 2C6.9-hz00, 6B9.22-hz00, 9C8.1-hz00, 16A9.11-hz00, 19G10.14-hz00 and 19H11.6-hz00.

The affinity of the anti-Claudin18.2 chimeric antibodies to Ba/F3-Claudin18.2 cells were determined. Specifically, Ba/F3-Claudin18.2 cells (60000 in 10 ul buffer) were incubated with serially diluted anti-human Claudin18.2 chimeric antibodies or the control antibody IMAB362 on ice for 30 min, followed by washing with FACS buffer (PBS+2% FBS) twice and incubating with fluorescent goat-anti-human secondary antibody (Thermo Fisher Sci., Cat: A-21445) on ice for another 30 min. The cells were then analyzed by FACS.

As shown in Table 3, the values of EC50 of 1E9.2-hz00, 16A9.11-hz00 or 19H11.6-hz00 was lower than that of the positive control IMAB362, indicating that the above anti-human Claudin 18.2 chimeric antibodies had stronger affinity than IMAB362. All 1E9.2-hz00, 6B9.22-hz00, 9C8.1-hz00, 16A9.11-hz00, or 19H11.6-hz00 showed stronger maximal mean fluorescence intensity than IMAB362, indicating that the amount of the antibodies of present invention bound to antigen in a saturated state was higher than that of IMAB362, and the antibody of the invention had stronger binding activity than IMAB362.

TABLE 3

Measurement of affinity of anti-human Claudin 18.2 chimeric antibodies to cells

| Antibody | EC50 (nM) | Max MFI ($\times 10^6$) |
|---|---|---|
| 1E9.2-hz00 | 11.03 | 11.8 |
| 6B9.22-hz00 | 18.24 | 16.70 |
| 9C8.1-hz00 | 23.95 | 14.41 |
| 16A9.11-hz00 | 10.48 | 12.40 |
| 19H11.6-hz00 | 11.64 | 12.97 |
| IMAB362 | 18.03 | 8.97 |

Example 6. Humanization of Anti-Human Claudin18.2 Mouse Antibodies

CDR-grafting method was used to humanize the two mouse antibodies 1E9.2 and 2C6.9. Briefly, the humanization process was involved in the following steps: the amino acid sequences of mouse monoclonal antibodies were aligned with the amino acid sequences of human germline antibody to identify human germline frameworks with high homology and good physical-chemical properties; the affinity to HLA-DR was determined and the human germline frameworks with low affinity to HLA-DR were then selected; the six CDR regions of mouse antibodies were then grafted to the selected heavy chain and light chain frameworks.

Specifically, the heavy chain and light chain CDRs of mouse antibodies 1E9.2 and 2C6.9 were grafted to the frameworks (FR) of the corresponding humanization templates. The humanization template for the heavy chain of 1E9.2 is human germline sequence IGHV3-21*04 (IMGT reference number HM855688). The humanization templates for light chain are human germline sequences IGKV4-1*01 (IMGT reference number Z00023) and IGKV6-21*02 (IMGT reference number KM455568). The humanization templates for heavy chain and light chain of 2C6.9 are human germline sequence IGHV4-59*01 (IMGT reference number AB019438) and IGKV4-1*01 (IMGT reference number Z00023), respectively.

Moreover, with computer simulation, molecular docking was performed to analyze the variable region and its surrounding framework amino acid sequences, in order to determine the spatial stereoscopic binding mode of the antibodies. By calculating electrostatic forces, Van der Waals forces, hydrophobic interactions and entropy, critical amino acid residues which may interact with Claudin18.2 or maintain spatial structure in the amino acid sequence of the mouse antibody were identified, and these mouse amino acids were maintained after grafting. In other words, a series of back mutations were taken in the FR region residues of humanization template so that the affinities of the mouse antibodies could be kept in humanized antibodies to the maximal extent.

Using the previously described methods, 9 humanized antibodies were constructed based on the CDRs of mouse antibody 1E9.2, which were named 1E9.2hz11, 1E9.2hz12, 1E9.2hz13, 1E9.2hz14, 1E9.2hz15, 1E9.2hz17, 1E9.2hz21, 1E9.2hz31 and 1E9.2hz41, respectively. 2 humanized antibodies were constructed based on the CDRs of mouse antibody 2C6.9, which were named 2C6.9hz11 and 2C6.9hz21, respectively. The heavy chain constant regions of the constructed antibodies are the same as wild-type human IgG1 heavy chain constant region (SEQ ID NO: 42). The light chain constant regions are all the same as wild-type human IgG1 light chain constant region (SEQ ID NO: 43).

The amino acid sequences of variable region and constant region of the above humanized antibodies are shown in Table 4.

TABLE 4

The amino acid sequences of variable region and constant region of the humanized antibodies

| Antibody Name | Variable Region of Heavy Chain (SEQ ID NO:) | Variable Region of Light Chain (SEQ ID NO:) | Constant Region of Heavy Chain (SEQ ID NO:) | Constant Region of Light Chain (SEQ ID NO:) |
|---|---|---|---|---|
| 1E9.2hz11 | 29 | 33 | 42 | 43 |
| 1E9.2hz12 | 29 | 34 | | |
| 1E9.2hz13 | 29 | 35 | | |
| 1E9.2hz14 | 29 | 36 | | |
| 1E9.2hz15 | 29 | 37 | | |
| 1E9.2hz17 | 29 | 38 | | |
| 1E9.2hz21 | 30 | 33 | | |
| 1E9.2hz31 | 31 | 33 | | |
| 1E9.2hz41 | 32 | 33 | | |
| 2C6.9hz11 | 39 | 41 | | |
| 2C6.9hz21 | 40 | 41 | | |

Example 7. Evaluation of the Affinity and ADCC Activity of the Anti-Human Claudin18.2 Humanized Antibodies In order to evaluate the anti-Claudin18.2 humanized antibodies, codon optimized cDNAs of the heavy chains and the light chains of the candidate humanized antibodies from Example 6 were synthesized and ligated into pcDNA3.4 (by Nanjing Genscript Biotech Corporation). Expi293F cells (purchased from Thermo Incorporation) were co-transfected with pcDNA3.4 coding the heavy chain and light chain of each antibody. The antibodies were purified from the supernatant using protein A (MabSelect SuRe, GE). The affinity of the humanized antibodies to Claudin18.2 was determined using Ba/F3-Claudin18.2 cells which over-expressed human Claudin18.2. Ba/F3-Claudin18.2 cells (60000 in 10 ul buffer) were incubated with purified humanized antibodies on ice for 30 min, followed by washing with buffer (PBS+2% FBS) twice and addition of Alexa647-labeled goat-anti-human IgG Fc antibody (1:500 dilution). The cells were incubated on ice for another 30 min and analyzed by IntelliCyt.

The results of affinity detected with Ba/F3-Claudin 18.2 cells over-expressing human Claudin 18.2 are shown in Table 5. The Max MFI showed that all the chimeric antibodies and humanized antibodies of 1E9.2 and control antibody IMAB362 could bind to Claudin18.2. The Max MFI of each of the chimeric antibody and humanized antibodies was stronger than that of control antibody IMAB362, indicating that the amount of the candidate antibody bound to antigen in a saturated state was higher than that of IMAB362; in another word, the antibody of present invention has stronger binding activity to the antigen.

TABLE 5

Measurement of affinity for anti-human Claudin 18.2 chimeric and humanized candidate antibodies to Ba/F3-Claudin 18.2 cells

| Candidate Antibody | Max MFI ($\times 10^6$) |
|---|---|
| 1E9.2-hz00 | 11.17 |
| 1E9.2-hz11 | 11.34 |
| 1E9.2-hz21 | 14.56 |
| 1E9.2-hz31 | 10.64 |
| 1E9.2-hz41 | 11.28 |
| 1E9.2-hz12 | 6.71 |
| 1E9.2-hz13 | 6.02 |
| 1E9.2-hz14 | 5.36 |
| 1E9.2-hz15 | 8.99 |
| 1E9.2-hz17 | 5.90 |
| IMAB362 | 4.99* |

*represents that the value is the average of two determinations.

The affinity of 2C6.9-hz21 to human claudin 18.2 on cell membrane was detected using HEK293T-Claudin 18.2 cells, as follows. HEK293T-Claudin 18.2 cells were detached and centrifuged, followed by washing for twice with PBS. And then the cells were resuspended in PBS containing 1% BSA and were plated into 96-well tip bottom plate at 300000 cells per well in a volume of 50 µl for 20 wells in total. 2C6.9-hz21 or IMAB362 antibody was then added with 11 concentrations starting from 1000 nM with three-fold dilution. Human IgG was served as negative control. The reactions were mixed well and incubated for 1 h at 4° C. in the dark. Following by three times of washing with PBS, the FITC-labelled anti-human Fc secondary antibody (Biolegend, 409322) was added and incubated for 0.5h in the dark. Detection was performed by flow cytometry (Beckman, Cytoflex) after washing for three times with PBS.

Figure 2C:
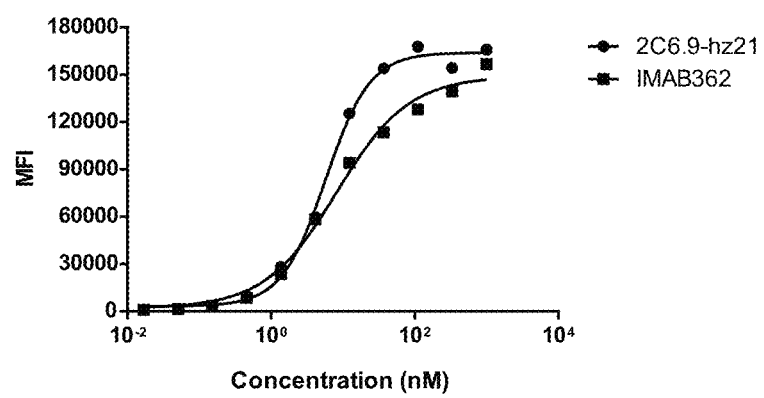
FIG. 2C: Determination of the affinity of 2C6.9-hz21 and IMAB362 by flow cytometry.

As shown in FIG. 2C and Table 6, the EC50 value of the binding affinity of 2C6.9-hz21 to HEK293T-Claudin 18.2 was lower than that of IMAB362; and the max fluorescence value of 2C6.9-hz21 was higher than that of IMAB362, indicating that the affinity of 2C6.9-hz21 to Claudin 18.2 on cell membrane was stronger than that of IMAB362.

TABLE 6

Measurement of affinity for humanized antibody 2C6.9-hz21 to HEK293T-Claudin 18.2 by flow cytometry

| Antibody Name | EC50 (nM) | Max MFI |
|---|---|---|
| 2C6.9-hz21 | 5.767 | 165866.3 |
| IMAB362 | 8.217 | 156715.7 |

In order to evaluate the ADCC activity, ten thousand Ba/F3-Claudin18.2 cells were cultured in 40 µl NK-92 media. Antibodies were serially diluted in 10 μl PBS. Fifty thousand NK-92MI_mCD16 cells in 50 μl NK-92 media were added and the reactions were incubated at 37° C. for 6h. 33.3 μl CytoTox-Glo (Promega, G9290) was added to each reaction and absorbance was read on a plate reader. As shown in Table 7, the EC50 of ADCC killing activity and max killing rate of 1E9.2 chimeric antibody and all 1E9.2 humanized antibodies against Ba/F3-Claudin 18.2 cells were both stronger than that of IMAB362. The results showed that the chimeric antibody and humanized antibody of 1E9.2 had stronger ADCC activity.

TABLE 7

Evaluation of ADCC activity of the chimeric and humanized antibodies against human Claudin 18.2

| | ADCC activity on Ba/F3-Claudin 18.2 cells | |
|---|---|---|
| Antibody Name | EC50 (μg/mL) | Max killing rate % |
| 1E9.2-hz00 | 0.049* | 59.83* |
| 1E9.2-hz11 | 0.041* | 60.17* |
| 1E9.2-hz41 | 0.048 | 55.43 |
| 1E9.2-hz12 | 0.091 | 64.36 |
| 1E9.2-hz13 | 0.068 | 63.78 |
| 1E9.2-hz14 | 0.097 | 60.45 |
| 1E9.2-hz15 | 0.080 | 66.22 |
| 1E9.2-hz17 | 0.113 | 59.64 |
| IMAB362 | 0.351* | 54.17* |

*represents that the value is the average of two determinations.

Example 8 Determination of the Affinity and Specificity of Anti-Human Claudin18.2 Humanized Antibody Human Claudin18.2 is a four transmembrane protein and has a complex structure. Cellular ELISA was thus carried out to maintain the structure of Claudin18.2. The stable cell line L929-Claudin 18.2 constructed in Example 1 were used for detection. Specifically, L929-Claudin 18.2 adherent cells were detached by 2 mM EDTA treatment. The cells were resuspended and adjusted to $2 \times 10^5$/mL and 100 μL of the resuspension was plated into 96 well plate and incubated overnight at 37° C. The next day, the media was removed, and the plate was washed with PBS once. 100 μL/well 4% formaldehyde was added to the plate. After 30 min of incubation at room temperature, formaldehyde was removed, followed by washing twice with PBS. Blocking buffer (PBS containing 2% BSA) was then added to the plate at 100 μL/well, and incubated at 37° C. for 2 h. After removal of blocking buffer, 100 μL/well of serially diluted antibodies (starting from 1 μM, with 4-fold dilution, for a total of 11 concentrations) were added to the corresponding wells, which were incubated at 37° C. for 2h afterwards. The plate was washed with 250 μL PBST for 5 times, and was allowed to stand for 2 min each time. 100 μL/well of horseradish peroxidase labeled anti-Human IgG secondary antibody (HRP-anti-Human IgG, Jackson ImmunoResearch, 109-035-003) diluted 1:10000 in PBS (containing 2% BSA) was added to the plate. The plate was incubated at 37° C. for 1 h and washed with 250 μL PB ST 6 times, wherein the plate was allowed to stand for 2 min each time. 100 μL/well of TMB solution (Thermo, 34029) was added. The reactions were incubated at 37° C. for 20 min and stopped with 50 μL 2 mol/L H2SO4. The absorbance at 450 nm was read on a plate reader (MD, SpectraMax M2) and the results were subjected to curve fitting by Graphpad Prism.

Figure 3A:
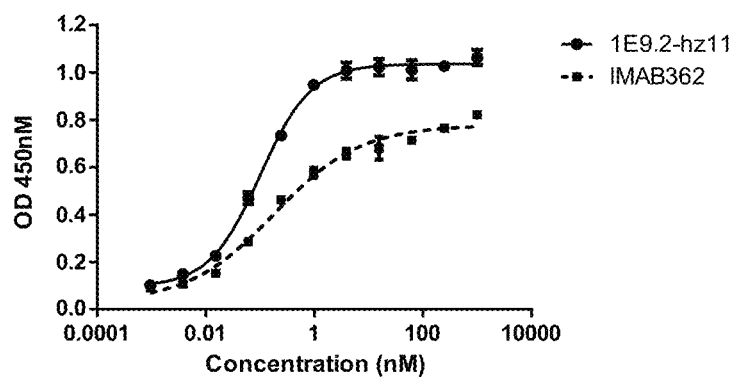
FIG. 3A: Determination of the affinity of 1E9.2-hz11 and IMAB362 binding to L929-Claudin 18.2 cells by ELISA.
Figure 3B:
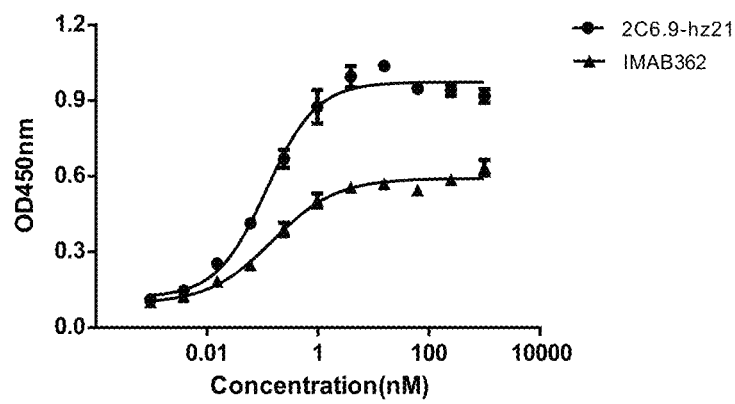
FIG. 3B: Determination of the affinity of 2C6.9-hz21 and IMAB362 binding to L929-Claudin 18.2 cells.
Figure 3C:
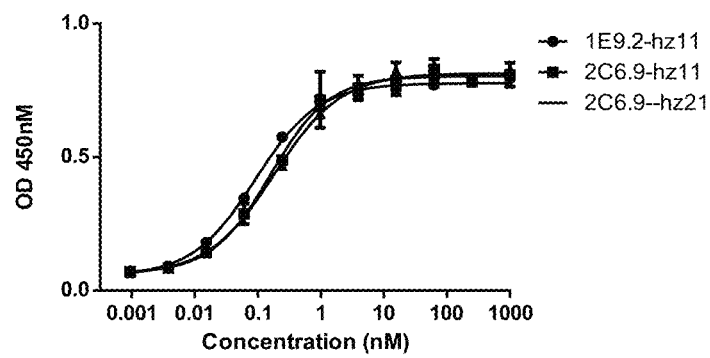
FIG. 3C: Determination of the affinity of 1E9.2-hz11, 2C6.9-hz11 and 2C6.9-hz21 binding to L929-Claudin 18.2 cells.

The results of multiple experiments are shown in FIGS. 3A, 3B, 3C, Table 8, Table 9 and Table 10, indicating that the affinity of humanized antibody 1E9.2-hz11 and 2C6.9-hz21 to human Claudin 18.2 are significantly higher than that of IMAB362.

TABLE 8

The affinity of the humanized antibody 1E9.2-hz1 1 binding to L929-Claudin 18.2 cells using Cellular ELISA

| Antibody Name | EC50 (nM) | Max Signal Value (OD450) |
|---|---|---|
| 1E9.2-hz11 | 0.1 | 1 |
| IMAB362 | 0.18 | 0.82 |

TABLE 9

The affinity of the humanized antibody 2C6.9-hz21 binding to L929-Claudin 18.2 cells using Cellular ELISA

| Antibody Name | EC50 (nM) | Max Signal Value (OD450) |
|---|---|---|
| 2C6.9-hz21 | 0.12 | 0.92 |
| IMAB362 | 0.15 | 0.53 |

TABLE 10

The affinity of the humanized antibody binding to L929-Claudin 18.2 cells using Cellular ELISA

| Antibody Name | EC50 (nM) | Max Signal Value (OD450) |
|---|---|---|
| 1E9.2-hz11 | 0.09 | 0.8 |
| 2C6.9-hz11 | 0.16 | 0.8 |
| 2C6.9-hz21 | 0.18 | 0.8 |

Figure 3D:
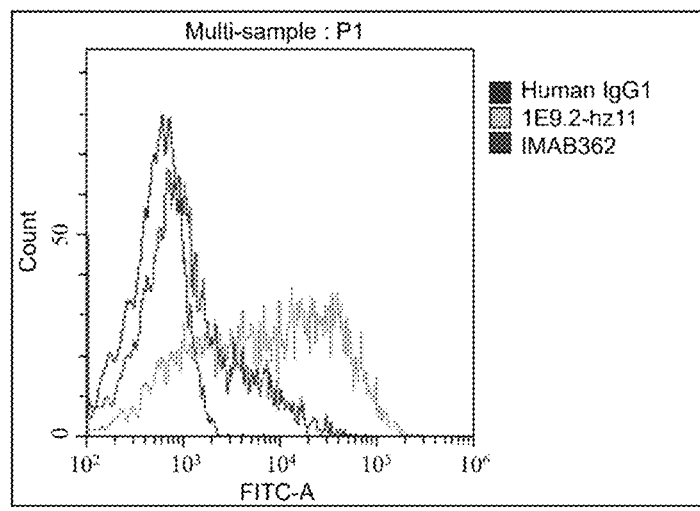
FIG. 3D: Determination of positive rate of NUGC-4 cells by 1E9.2-hz11 and IMAB362.
Figure 3E:
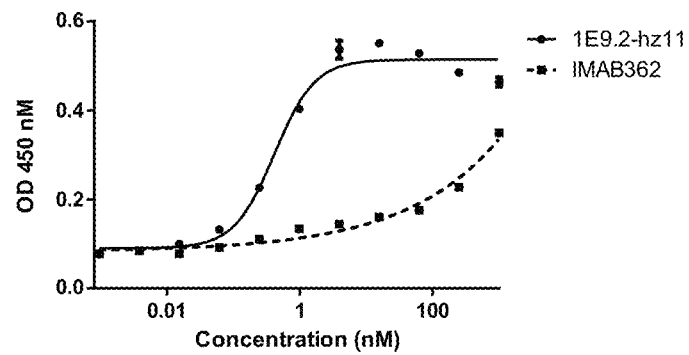
FIG. 3E: Determination of the affinity of 1E9.2-hz11 and IMAB362 binding to NUGC-4 cells.

To determine binding affinity of the candidate antibodies to cell lines endogenously expressing human Claudin18.2, FACS analysis was performed to detect human Claudin18.2 expression level on NUGC-4 cells (purchased from Japan JCRB cell bank, catalog number: JCRB0834) which endogenously expresses human Claudin18.2. As shown in FIG. 3D, 80% of NUGC-4 cells tested positive for Claudin 18.2 by 1E9.2-hz11, while only 20% tested positive by IMAB362; human IgG1 was provided as negative control. The result showed that 1E9.2-hz11 can detect more endogenously expressed human Claudin18.2 than IMAB362. The binding affinity between candidate antibodies and NUGC-4 cells was then determined by Cellular ELISA following the same protocol as above. As shown in FIG. 3E and Table 11, the EC50 and the Max signal value (OD450) showed that 1E9.2-hz11 had higher affinity and binding capability.

TABLE 11

The affinity of the humanized antibody binding to NUGC-4 cells

| Antibody Name | EC50 (nM) | OD450 |
|---|---|---|
| 1E9.2-hz11 | 0.4129 | 0.5 |
| IMAB362 | ≈663.7 | Not detected |

The specificity of candidate antibodies was detected by FACS. The steps are as follows, HEK293T, HEK293T-human Claudin 18.1 and HEK293T-human Claudin18.2 cells were detached and then centrifuged. After washing twice with PBS, the cells were resuspended with PBS containing 1% BSA. 300,000 cells for each cell line were added with the candidate antibodies at a final concentration of 1000 nM, mixed well, and incubated for 1 h at 4° C., protected from light. Then the cells were washed for three times with PBS and FITC-labeled anti-human Fc secondary antibody (BioLegend, 409322) was added, followed by 0.5h of incubation at 4° C. in the dark. Detection was performed by flow cytometry (Beckman, Cytoflex) after washing with PBS for three times.

Figure 3F:
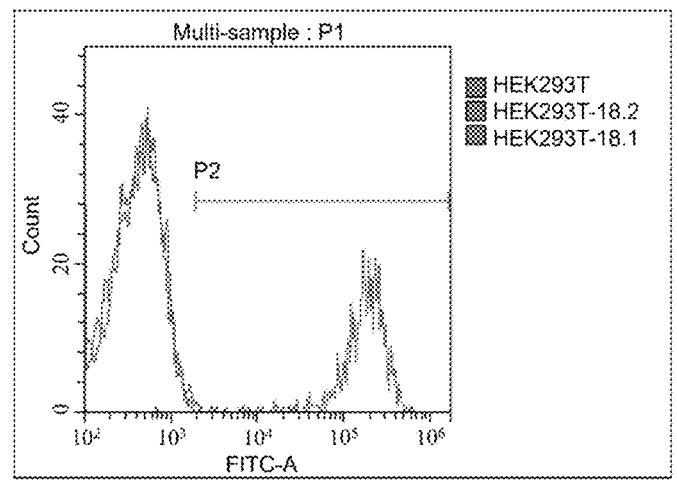
FIG. 3F: Determination of the specificity of 1E9.2-hz11 by flow cytometry.
Figure 3G:
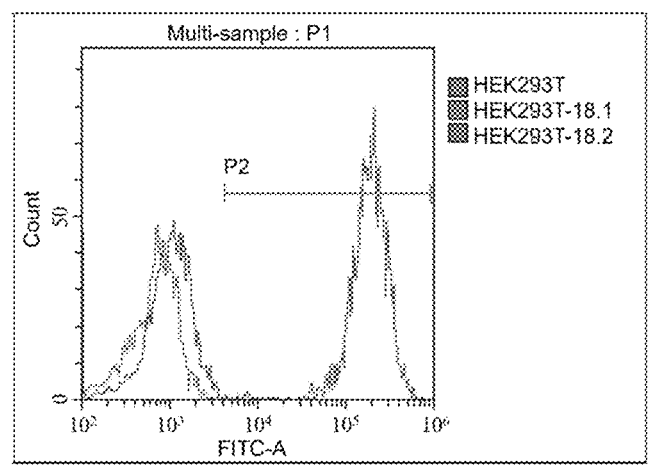
FIG. 3G: Determination of the specificity of 2C6.9-hz21 by flow cytometry.

As shown in FIGS. 3F and 3G, both 1E9.2-hz11 and 2C6.9-hz21 could specifically bind to human Claudin 18.2 but not human Claudin 18.1.

Example 9. Determination of Complement Dependent Cytotoxicity (CDC) of Anti-Claudin18.2 Humanized Antibody 1E9.2-hz11 belongs to IgG1 subtype, which can activate classical complement pathway effectively, and induce complement dependent cytotoxicity (CDC). Guinea pig serum (purchased from Zhengzhou Baiji, catalog number S0001) which is rich in complements was used in our research in order to determine the CDC activity of 1E9.2-hz11. The procedure is described as follows: HEK293T-Claudin 18.2 cells were harvested and centrifuged followed by adjustment of cell density. $5 \times 10^4$/well of cells were plated on a plate and incubated overnight. DMEM containing 20% guinea pig serum was prepared the next day and was used to dilute 1E9.2-hz11 and IMAB362. Starting from 20 μg/mL, 10 concentrations were prepared with two-fold dilution. The original cell culture media for HEK293T-Claudin 18.2 cells was removed, and the antibody dilutions were added to the corresponding wells, 100 μL/well. 10 μl/well lysis buffer was provided as the positive control. The reactions were left to stand in incubator at 37° C., 5% $CO_2$ and incubated for 3 h. Then, CCK8 (Rhinogen, QDY-003-D) was added at 20 μl/well and allowed to react for 2h. Absorbance at 450 nm were taken on a plate reader (MD, SpectraMax M2). The results were subjected to curve fitting by Graphpad Prism.

Figure 4A:
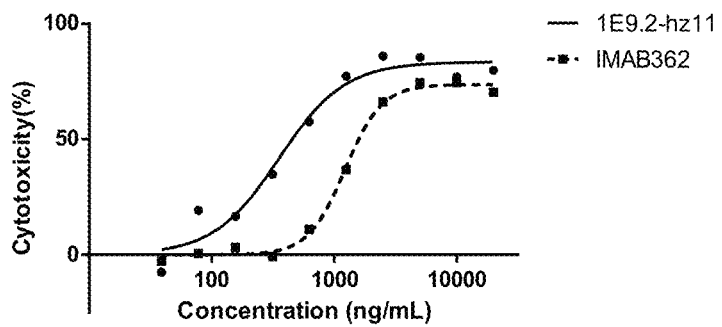
FIG. 4A: Determination of the CDC killing activity of 1E9.2-hz11 and IMAB362 against HEK293T-Claudin18.2 cells.

As shown in FIG. 4, the CDC activity of 1E9.2-hz11 was significantly stronger than that of the control antibody IMAB362, which was 3.5 times higher than that of IMAB362. The maximal killing rate of 1E9.2-hz11 was about 82%, while the rate of IMAB362 was about 70%.

The CDC detection method of antibody 2C6.9-hz21 is similar to that of 1E9.2-hz11. The cells were left to stand in incubator at 37° C., 5% $CO_2$ and incubated for 3h, with the medium containing guinea pig serum. Subsequently, Cell-Titer-Glo Luminescent (CTG, Purchased from Promega, Item No.: G7573) was added at 50 μl/well for staining followed by a 30-second mixing and left to stand for 1 min at room temperature. The fluorescence signal value was then determined by a microplate reader (MD, SpectraMax M2), the results of which were imported into Graphpad Prism for curve fitting.

Figure 4B:
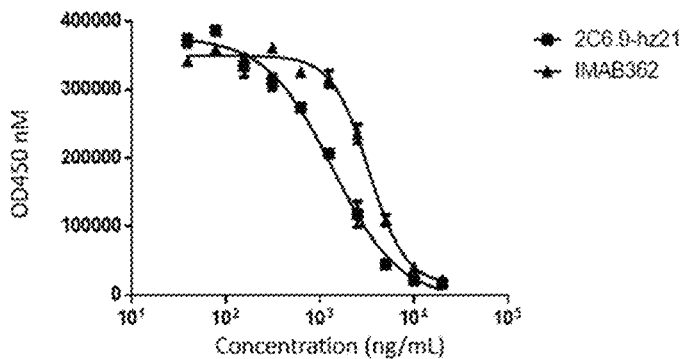
FIG. 4B: Determination of the CDC killing activity of 2C6.9-hz21 and IMAB362 against HEK293T-Claudin18.2 cells.

As shown in FIG. 4B and Table 12, the CDC activity of 2C6.9-hz21 was higher than that of the control antibody IMAB362.

TABLE 12

The CDC activity determination of anti-Claudin 18.2 humanizec antibody

| Antibody Name | EC50 value (ng/mL) |
| --- | --- |
| 2C6.9-hz21 | 1363 |
| IMAB362 | 3317 |

Example 10. Determination of the Antibody-Dependent Cell-Mediated Cytotoxicity (ADCC) of Anti-Human Claudin18.2 Humanized Antibody 1E9.2-hz11 belongs to IgG1 subtype and has relative strong antibody-dependent cell-mediated cytotoxicity (ADCC). NK cell mediated killing assay was used to determine the ADCC activity of 1E9.2-hz11. The steps were as follows: HEK293T-Claudin 18.2, L929-Claudin 18.2, KATOIII-Claudin 18.2 and NUGC-4 cells were harvested and centrifuged followed by adjustment of cell density. $1 \times 10^4$/well of cells were plated on a plate and incubated overnight. The medium was removed on the next day. NK92MI-CD16a cells (Huabo Biopharm) were centrifuged, resuspended in MEMA medium and adjusted to $1 \times 10^6$/mL, then 50 μL/well cells were added to the corresponding wells. 1E9.2-hz11 and IMAB362 antibodies were diluted with MEMA medium. For HEK293T-Claudin18.2, L929-Claudin18.2 and KATOIII-Claudin18.2 cells, ten antibody concentrations were tested, starting from 40 μg/mL with 5-fold dilution. For NUGC-4 cells, eleven antibody concentrations were tested, starting from 2 mg/mL with 5-fold dilution. 50 μL/well of the diluted antibodies were added to the corresponding wells and the reactions were left to stand in incubator at 37° C., 5% $CO_2$ and incubated for 5.5h. Lysis buffer was then added to the positive control well and incubated for another 0.5h. 50 μL/well of Lactate Dehydrogenase (LDH) detection agent (DOJINDO LABORATORISE, CK12) were added to the wells and the absorbance at 490 nm were taken every 10 min on a plate reader (MD, SpectraMax M2). The results were imported into Graphpad Prism for curve fitting.

As shown in FIGS. 5A-5D and Table 13, the ADCC activities of 1E9.2-hz11 on HEK293T-Claudin 18.2, KATOIII-Claudin 18.2 and NUGC-4 are all stronger than those of IMAB362.

TABLE 13

The ADCC activity of the anti-human Claudin 18.2 humanized antibody

| | antibodies | | | |
| --- | --- | --- | --- | --- |
| | 1E9.2-hz11 | | IMAB362 | |
| Cell lines | EC50 (ng/mL) | Max. Cytotoxicity (%) | EC50 (ng/mL) | Max. Cytotoxicity (%) |
| HEK293T-Claudin 18.2 | 52.83 | 83 | 33.58 | 55 |
| L929-Claudin 18.2 | 2.388 | 46 | 78.07 | 52 |
| KATOIII-Claudin 18.2 | 3.586 | 64 | 10.10 | 49 |
| NUGC-4 | 133.6 | 43 | 1219 | 35 |

Figure 5A:
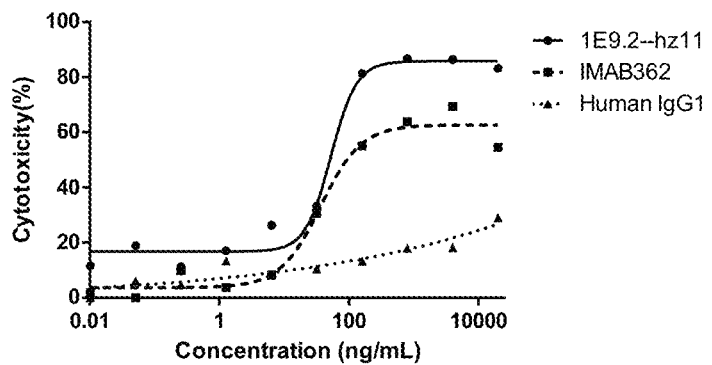
FIG. 5A: Determination of the ADCC activity of 1E9.2-hz11 and IMAB362 against HEK293T-Claudin18.2 cells.
Figure 5B:
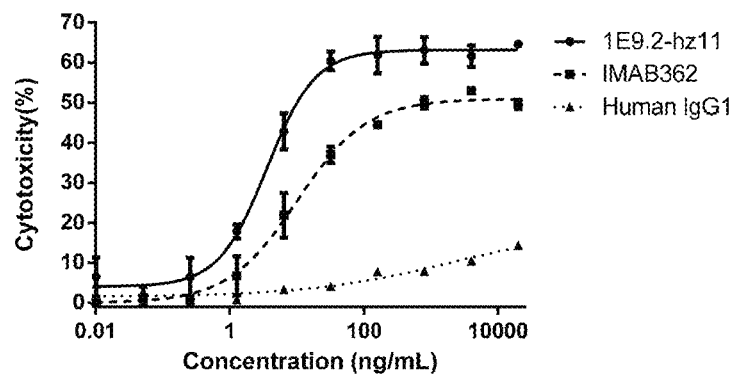
FIG. 5B: Determination of the ADCC activity of 1E9.2-hz11 and IMAB362 against KATOIII-Claudin18.2 cells.
Figure 5C:
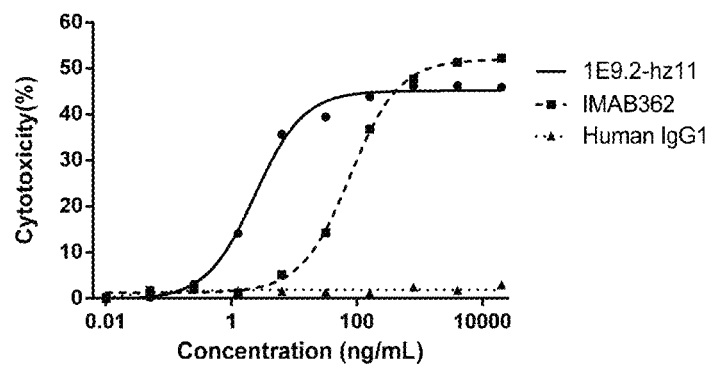
FIG. 5C: Determination of the ADCC activity of 1E9.2-hz11 and IMAB362 against L929-Claudin18.2 cells.
Figure 5D:
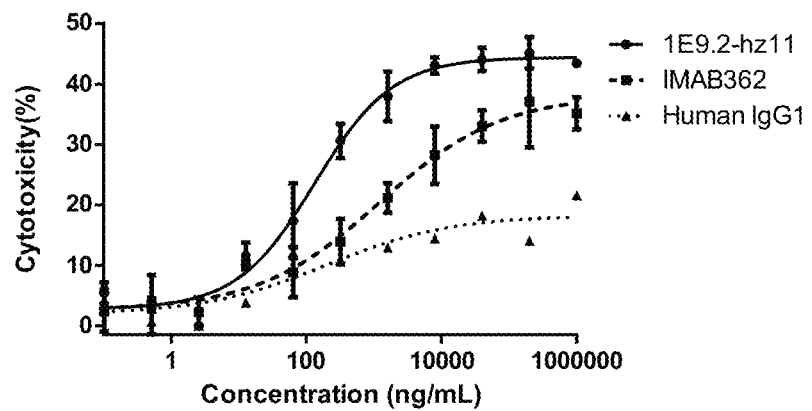
FIG. 5D: Determination of the ADCC activity of 1E9.2-hz11 and IMAB362 against NUGC-4 cells.
Figure 5E:
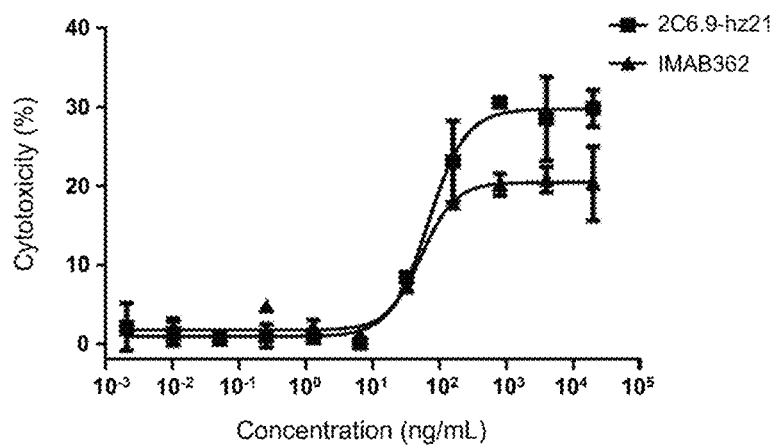
FIG. 5E: Determination of the ADCC activity of 2C6.9-hz21 and IMAB362 against HEK293T-Claudin18.2 cells.

Antibody 2C6.9-hz21 is also of IgG1 subtype, so the method for detecting its ADCC activity is the same as that of antibody 1E9.2-hz11. The cell used was HEK293T-Claudin 18.2. Results are shown in FIG. 5E and Table 14.

The ADCC activity of antibody 2C6.9-hz21 on HEK293T-Claudin 18.2 is stronger than that of IMAB362.

TABLE 14

The ADCC activity of the anti-Claudin 18.2 humanized antibody 2C6.9-hz21

| Antibody Name | EC50 value (ng/mL) | Max Cytotoxicity (%) |
|---|---|---|
| 2C6.9-hz21 | 67.67 | 30 |
| IMAB362 | 57.66 | 20 |

Example 11. Determination of the Pharmacokinetics (PK) Properties of Anti-Human Claudin18.2 Humanized Antibody in Mouse Model To determine the PK properties of 1E9.2-hz11 and IMAB362 in mouse model, 10 mg/kg of 1E9.2-hz11 or IMAB362 were intravenously injected into SCID mice (Beijing Vital River Laboratory Animal Technology Co., Ltd.), 2 mice per group. Blood samples were taken 8 h, 1 d, 3 d, 8 d and 15 d after injection and serum antibody concentrations were determined by Cellular ELISA as described in Example 8. Standard curves were prepared using 1E9.2-hz11 and IMAB362 standards by Graphpad Prism. The data of mouse serum was subjected to curve fitting. The PK properties of 1E9.2-hz11 and IMAB362 were determined.

As shown in Table 15, the half-life of 1E9.2-hz11 and IMAB362 in mouse are 42.5h and 35.77h, respectively. 1E9.2-hz11 is better than IMAB362.

TABLE 15

Determination of the PK properties of anti-human Claudin 18.2 humanized antibody

| | Half-life (hours) | AUC (h*μg/mL) |
|---|---|---|
| 1E9.2-hz11 | 42.50 | 9088.87 |
| IMAB362 | 35.77 | 7391.22 |

Example 12. In Vivo Efficacy of Anti-Claudin18.2 Humanized Antibody

In vivo efficacy of anti-Claudin18.2 humanized antibody was demonstrated through the anti-tumor effect thereof on subcutaneous transplantation tumor model of human gastric cancer cell line NCI-N87-Claudin 18.2 (an engineered NCI-N87 cell line overexpressing human Claudin 18.2) in Balb/c nude mice. Specifically, the anti-Claudin18.2 humanized antibody was injected into a tumor-bearing mouse model subcutaneously implanted with NCI-N87-Claudin 18.2 through tail vein injection, and the tumor volume and the change in animal weight were measured regularly to evaluate the in vivo efficacy of anti-human Claudin18.2 humanized antibody (tumor inhibition efficacy).

Specific steps were as follows: NCI-N87-Claudin18.2 cells were cultured in RPMI1640 medium containing 10% fetal bovine serum at 37° C. and 5% $CO_2$. Cells in exponential growth phase were collected and resuspended in PBS to a suitable concentration, and then inoculated subcutaneously into female Balb/c nude mice (Biocytogen Jiangsu Co., Ltd, permit no. SOCK (Su) 2016-0004) at an amount of $5 \times 10^6$ cells per mouse in 0.1 mL PBS, to establish the subcutaneous transplantation tumor model. The day of inoculation was record as P0. The experiments were performed with three groups: intravenous immunoglobulin (Negative Control, Chengdu Rongsheng Pharmaceuticals Co. Ltd., abbreviated as Human IgG), combination of Epirubicin+Oxaliplatin+5-fluorouracil (abbreviated as EOF chemicals), and combination group of 1E9.2-hz11+EOF chemicals. On day 4, 11, 18 and 25, EOF chemicals (Epirubicin 1.25 mg/kg, Oxaliplatin 3.25 mg/kg, 5-fluorouracil 56.25 mg/kg) were administered intraperitoneally (once a week for 4 weeks); for the combination group of 1E9.2-hz11+EOF chemicals, on the basis of EOF administration, 1E9.2-hz11 antibody (10 mg/kg, 2 times a week for 4 weeks) was further administered via the tail vein on Day 5, 8, 12, 15, 19, 22, 26, and 29. The tumor volume and body weight of mice after administration was observed and measured regularly.

The tumor diameters were measured by vernier caliper. The tumor volume was calculated according to the following formula: $V=0.5 \ a \times b^2$, in which a and b represent the long diameter and short diameter of the tumor respectively. The death of animals was observed and record every day.

The anti-tumor efficacy of antibody expressed as the tumor growth inhibition rate (TGI) was calculated as following formula:

$$TGI(\%)=[1-(V_T End - V_T Int)/(V_C End - V_C Int)] \times 100\%$$

In which $V_T End$ means the mean tumor volume of the treatment group at the end of study;

$V_T Int$ means the mean tumor volume of the treatment group at the beginning of study;

$V_C End$ means the mean tumor volume of the negative control group at the end of study;

$V_C Int$ means the mean tumor volume of the negative control group at the beginning of study.

The anti-tumor efficacy of antibody expressed as the relative tumor growth rate (T/C) was calculated as following formula:

$$T/C(\%)=(T_t/T_0)/(C_t/C_0) \times 100\%$$

In which T0 means the average tumor volume of the treatment group at the time of initiation (i.e., P0);

$T_t$ means the average tumor volume of treatment group at the time of each measurement;

$C_0$ means the average tumor volume of the negative control group at the time of initiation (i.e., P0);

$C_t$ means the average tumor volume of the negative control group at the time of each measurement.

Figure 6A:
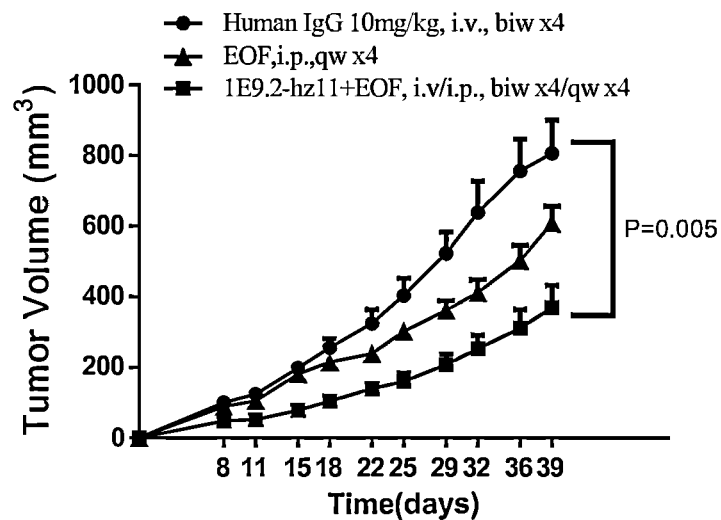
FIG. 6A: Anti-tumor effect detection of 1E9.2-hz11.

The results are shown in Table 16 and FIG. 6A. The EOF group has a certain inhibitory effect on the tumor growth of the transplantation tumor model of gastric cancer using NCI-N87-Claudin 18.2; but the tumor inhibition rate is further improved showing a remarkable anti-tumor effect, when combined with 1E9.2-hz11 antibody (10 mg/kg).

TABLE 16

NCI-N87-Claudin18.2 + Balb/c nude mouse model

P29

| No | Group | Dose (mg/kg) | Tumor Volume (mm³) ($\bar{x}$ ± SEM) | TGI (%) | T/C (%) | P Value (vs. Group 1) |
|---|---|---|---|---|---|---|
| 1 | Human IgG | 10 | 806.10 ± 94.68 | — | — | — |
| 2 | EOF | E: 1.25, O: 3.25, F: 56.25 | 607.87 ± 48.13 | 24.59 | 75.41 | 0.11 |
| 3 | 1E9.2-hz11 + EOF | 10 + [1.25, 3.25, 56.25] | 369.85 ± 61.60 | 54.12 | 45.88 | 0.005 |

Note:
TGI: Tumor Growth Inhibition Rate;
T/C: The Relative Tumor Growth Rate

The mouse subcutaneous xenograft tumor model of NCI-N87-Claudin 18.2 was established by the method mentioned above. When the average volume of the tumors was about 110 mm³, the tumor-bearing mice were grouped randomly according to tumor size. There were 3 groups: the group of anti-chicken lysozyme human IgG1 of isotype control (Negative Control, Chengdu Kelun-Biotech Co. Ltd., abbreviated as IgG1 WT), the group of paclitaxel for injection (Albumin Bound, Hunan Kelun), and the combination group of 2C6.9-hz21+Paclitaxel for injection. All samples were injected via tail vein twice a week for 3 weeks. After administration, the tumor volume and body weight of mice was observed and measured regularly, and the data analysis method is as described above.

Figure 6B:
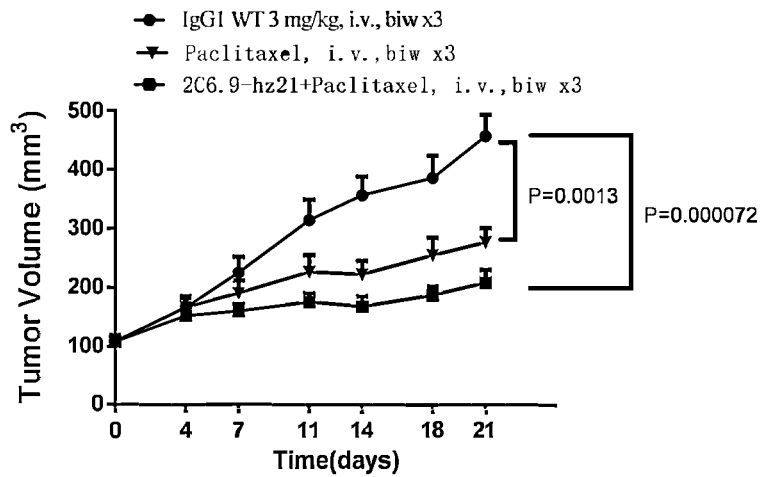
FIG. 6B: Anti-tumor effect detection of 2C6.9-hz21
Figure 6C:
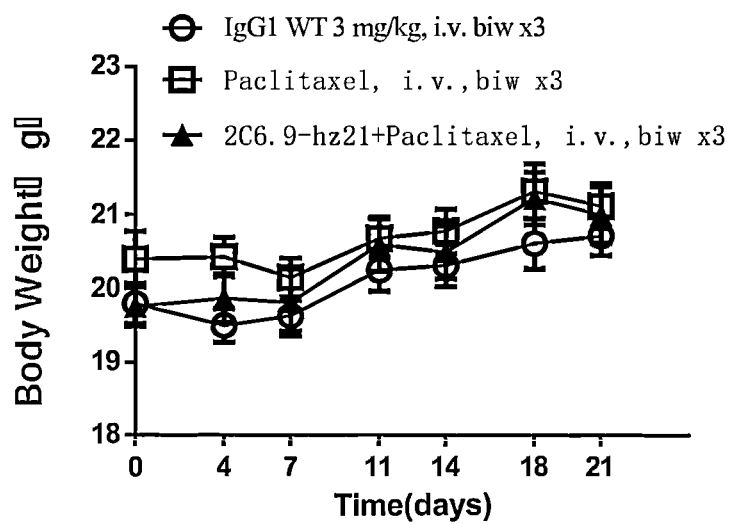
FIG. 6C: Monitoring of body weight changes during the tumor suppression experiment of 2C6.9-hz21.

The results are shown in Table 17 and FIG. 6B. The group of paclitaxel for injection (10 mg/kg) has an obvious anti-tumor efficacy, but the tumor the inhibition rate is further improved showing a remarkable anti-tumor effect when combined with 2C6.9-hz21 antibody. No mouse died and no significant weight loss (FIG. 6C) was observed in all mice during the observation period, indicating that 2C6.9-hz21 has no obvious drug toxicity and the mice tolerated well during the treatment.

TABLE 17

NCI-N87-Claudin 18.2 + Balb/c nude mouse model

P21

| No | Group | DOSE (mg/kg) | Tumor Volume (mm³) ($\bar{\chi}$ × SEM) | TGI (%) | T/C (%) | P Value (vs. Group 1) |
|---|---|---|---|---|---|---|
| 1 | IgG1 WT | 3 | 456.60 ± 36.43 | — | — | — |
| 2 | Paclitaxel for injection | 12 | 276.31 ± 23.46 | 51.60 | 60.86 | 0.0013 |
| 3 | 2C6.9-hz21 + Paclitaxel for injection | 10 + 12 | 207.52 ± 21.25 | 71.43 | 45.58 | 0.000072 |

Note:
TGI: Tumor Growth Inhibition Rate;
T/C: The Relative Tumor Growth Rate

In summary, the combination of humanized antibodies such as 1E9.2-hz11 and 2C6.9-hz21 with chemotherapy drugs (such as EOF or paclitaxel) can effectively inhibit tumor growth.

Although the examples of this invention have been described in detail, the researchers in this area should understand: following the guidance of the published method, modifications and variations of the example details can be made and all these modifications are protected within the scope of this patent.

The invention claimed is:

1. An antibody or antigen-binding fragment thereof that specifically binds to CLDN18.2, wherein the antibody or antigen-binding fragment thereof comprises the following complementarity determining regions (CDRs):
CDR-H1, CDR-H2 and CDR-H3 of the heavy chain variable domain (VH) shown in SEQ ID NO: 3, 39 or 40; and CDR-L1, CDR-L2 and CDR-L3 of the light chain variable domain (VL) shown in SEQ ID NO: 4 or 41.

2. The antibody or antigen binding fragment thereof according to claim 1, wherein the antibody or antigen binding fragment thereof comprises:
(1) the following heavy chain variable region (VH) and/or light chain variable region (VL), wherein CDR is defined according to the IMGT numbering system:
a heavy chain variable region (VH) comprising the following 3 CDRs: CDR-H1 with a sequence as set forth in SEQ ID NO: 11, CDR-H2 with a sequence as set forth in SEQ ID NO: 12 or 110, and CDR-H3 with a sequence as set forth in SEQ ID NO: 13; and/or,
a light chain variable region (VL) comprising the following 3 CDRs: CDR-L1 with a sequence as set forth in SEQ ID NO: 14, CDR-L2 with a sequence as set forth in SEQ ID NO: 15, and CDR-L3 with a sequence as set forth in SEQ ID NO: 16;
or
(2) the following heavy chain variable region (VH) and/or light chain variable region (VL), wherein CDRs are defined according to the AbM numbering system:
a heavy chain variable region (VH) comprising the following 3 CDRs: CDR-H1 with a sequence as set forth in SEQ ID NO:23, CDR-H2 with a sequence as set forth in SEQ ID NO: 24 or 111, and CDR-H3 with a sequence as set forth in SEQ ID NO: 25; and/or,
a light chain variable region (VL) comprising the following 3 CDRs: CDR-L1 with a sequence as set forth in SEQ ID NO: 26, CDR-L2 with a sequence as set forth in SEQ ID NO: 27, and CDR-L3 with a sequence as set forth in SEQ ID NO: 28.

3. The antibody or antigen binding fragment thereof according to claim 1 wherein the antibody or antigen binding fragment thereof comprises:
(a) a VH sequence as shown in any one of SEQ ID NOs: 3, 39, and 40, and/or, a VL sequence as shown in any one of SEQ ID NOs: 4, and 41;

(b) a VH sequence having at least 70%, at least 80%, at least 85%, at least 90%, at least 91%, at least 92%, at least 93%, at least 94%, at least 95%, at least 96%, at least 97%, at least 98%, at least 99% or 100% identity to the VH of (a); and/or a VL sequence having at least 70%, at least 80%, at least 85%, at least 90%, at least 91%, at least 92%, at least 93%, at least 94%, at least 95%, at least 96%, at least 97%, at least 98%, at least 99% or 100% identity to the VL of (a); or (c) a VH sequence comprising a substitution, deletion, or addition of 1, 2, 3, 4, or 5 amino acids compared with the VH of (a); and/or a VL sequence comprising a substitution, deletion, or addition of 1, 2, 3, 4, or 5 amino acids compared with the VL of (a).

4. The antibody or antigen binding fragment thereof according to claim 1 which comprises:

(a) a VH having a sequence of SEQ ID NO: 3 and a VL having a sequence of SEQ ID NO: 4;

(b) a VH having a sequence of SEQ ID NO: 39 and a VL having a sequence of SEQ ID NO: 41;

(c) a VH having a sequence of SEQ ID NO: 40 and a VL having a sequence of SEQ ID NO: 41;

(d) a VH having at least 70%, at least 80%, at least 85%, at least 90%, at least 91%, at least 92%, at least 93%, at least 94%, at least 95%, at least 96%, at least 97%, at least 98%, at least 99% or 100% identity to the VH in any of (a) to (c); and/or, a VL having at least 70%, at least 80%, at least 85%, at least 90%, at least 91%, at least 92%, at least 93%, at least 94%, at least 95%, at least 96%, at least 97%, at least 98%, at least 99% or 100% identity to the VL in any of (a) to (c); or (e) a VH comprising a substitution, deletion, or addition of one or several amino acids compared with the VH in any of (a) to (c); and/or, a VL comprising a substitution, deletion, or addition of one or several amino acids compared with the VL in any of (a) to (c).

5. The antibody or antigen binding fragment thereof according to claim 1, wherein the antibody or antigen binding fragment thereof is a mouse antibody, a chimeric antibody, or a humanized antibody.

6. The antibody or antigen binding fragment thereof according to claim 1, wherein the antibody or antigen binding fragment further comprises:

(a) a heavy chain constant region (CH) of a human immunoglobulin or a variant thereof, wherein said variant comprises a substitution, deletion, or addition of one or several amino acids compared with the sequence from which it is derived; and (b) a light chain constant region (CL) of a human immunoglobulin or a variant thereof, wherein said variant comprises a substitution, deletion, or addition of one or several amino acids compared with the sequence from which it is derived.

7. The antibody or antigen binding fragment thereof according to claim 1, wherein the antibody comprises (a) a heavy chain comprising a VH having a sequence of SEQ ID NO: 3 and a heavy chain constant region (CH) having a sequence of SEQ ID NO: 42, and a light chain comprising a VL having a sequence of SEQ ID NO: 4 and a light chain constant region (CL) having a sequence of SEQ ID NO: 43;

(b) a heavy chain comprising a VH having a sequence of SEQ ID NO: 39 and a heavy chain constant region (CH) having a sequence of SEQ ID NO: 42, and a light chain comprising a VL having a sequence of SEQ ID NO: 41 and a light chain constant region (CL) having a sequence of SEQ ID NO: 43; or, (c) a heavy chain comprising a VH having a sequence of SEQ ID NO: 40 and a heavy chain constant region (CH) having a sequence of SEQ ID NO: 42, and a light chain comprising a VL having a sequence of SEQ ID NO: 41 and a light chain constant region (CL) having a sequence of SEQ ID NO: 43.

8. The antibody or antigen binding fragment thereof according to claim 1, wherein the antibody or antigen binding fragment comprises:

a heavy chain, comprising an amino acid sequence selected from the group consisting of:

(i) a sequence as set forth in SEQ ID NO: 106;

(ii) a sequence having a substitution, deletion, or addition of one or several amino acids compared with SEQ ID NO: 106; or (iii) a sequence having at least 80%, at least 85%, at least 90%, at least 91%, at least 92%, at least 93%, at least 94%, at least 95%, at least 96%, at least 97%, at least 98%, at least 99% or 100% identity to SEQ ID NO: 106; and a light chain, comprising an amino acid sequence selected from the group consisting of:

(iv) a sequence as set forth in SEQ ID NO: 107;

(v) a sequence having a substitution, deletion, or addition of one or several amino acids compared with SEQ ID NO: 107; or (vi) a sequence having at least 80%, at least 85%, at least 90%, at least 91%, at least 92%, at least 93%, at least 94%, at least 95%, at least 96%, at least 97%, at least 98%, at least 99% or 100% identity to SEQ ID NO: 107.

9. The antibody or antigen binding fragment thereof according to claim 1, wherein the antibody or antigen binding fragment thereof is selected from scFv, Fab, Fab', $F(ab')_2$, Fv fragment, disulfide-linked Fv (dsFv), diabody, bispecific antibody, and multi-specificity antibody.

10. The antibody or antigen binding fragment thereof according to claim 1, wherein the antibody or antigen binding fragment thereof is labeled.

11. The antibody or antigen binding fragment thereof according to claim 1, characterized by one or more of the following:

(1) the antibody or antigen binding fragment thereof binds to CLDN18.2 with a KD value of less than about 100 nM;

(2) the antibody or antigen binding fragment thereof binds to CLDN18.2 with an EC50 value of less than about 500 nM;

(3) said antibody or antigen binding fragment does not bind to CLDN18.1 CLDN18.1;

(4) said antibody or antigen binding fragment has antibody-dependent cellular cytotoxicity (ADCC) activity and/or complement-dependent cytotoxicity (CDC) activity; and (5) said antibody or antigen binding fragment has enhanced ADCC activity and/or CDC activity.

12. A conjugate, which comprises an antibody or an antigen binding fragment thereof, and a conjugate moiety, wherein said antibody is the antibody or antigen binding fragment thereof of claim 1, and the conjugate moiety is selected from: a detectable label, radioisotopes, fluorescent substances, luminescent substances, colored substances, enzymes, polyethylene glycol (PEG), nuclides, nucleic acids, small molecule toxins, polypeptides with binding activity, proteins, receptors, ligands, and other active substance that inhibits tumor cell growth or promotes apoptosis or necrosis of tumor cells.

13. A chimeric antigen receptor, which comprises the antibody or antigen binding fragment thereof of claim 1, a transmembrane domain, and one or multiple intracellular T cell signaling domains.

14. A multi-specific antibody, which is formed by conjugation of a first antibody or a fragment thereof with an additional antibody or a fragment thereof or with an antibody mimetic, wherein each antibody or fragment thereof or antibody mimetic retains the original binding specificity, and the first antibody or fragment thereof is the antibody or antigen binding fragment thereof of claim 1.

15. A pharmaceutical composition, which comprises a pharmaceutically acceptable carrier and/or an excipient and comprises one of the following:
   the antibody or antigen binding fragment thereof of claim 1, or
   a vector comprising an isolated nucleic acid molecule encoding the antibody or antigen binding fragment thereof, or
   a host cell comprising an isolated nucleic acid molecule encoding the antibody or antigen binding fragment thereof, or
   a conjugate comprising the antibody or antigen binding fragment thereof and a conjugate moiety, or
   a chimeric antigen receptor comprising the antibody or antigen binding fragment thereof, a transmembrane domain, and one or multiple intracellular T cell signaling domains, or
   a multi-specific antibody formed by conjugation of the antibody or antigen binding fragment thereof with an additional antibody or a fragment thereof or with an antibody mimetic.

16. The pharmaceutical composition according to claim 15, which further comprises a second antibody or a nucleic acid encoding the second antibody, the second antibody specifically binds to a receptor or ligand selected from the group consisting of: PD-1, PD-L1, PD-L2, TIM-3, LAG-3, VISTA, CTLA-4, OX40, BTLA, 4-1BB, CD96, CD27, CD28, CD40, LAIR1, CD160, 2B4, TGF-R, KIR, ICOS, GITR, CD3, CD30, BAFFR, HVEM, CD7, LIGHT, SLAMF7, NKp80, B7-H3 and any combination thereof.

17. A diagnostic or therapeutic kit, which comprises an instruction for use and comprises one of the following:
   the antibody or antigen binding fragment thereof of any one of claim 1, or
   a vector comprising an isolated nucleic acid molecule encoding the antibody or antigen binding fragment thereof, or
   a host cell comprising an isolated nucleic acid molecule encoding the antibody or antigen binding fragment thereof, or
   a conjugate comprising the antibody or antigen binding fragment thereof and a conjugate moiety, or
   a chimeric antigen receptor comprising the antibody or antigen binding fragment thereof, a transmembrane domain, and one or multiple intracellular T cell signaling domains, or
   a multi-specific antibody formed by conjugation of the antibody or antigen binding fragment thereof with an additional antibody or a fragment thereof or with an antibody mimetic, or
   a pharmaceutical composition comprising the antibody or antigen binding fragment thereof, the vector, the host cell, the conjugate, the chimeric antigen receptor, or the multi-specific antibody, and a pharmaceutically acceptable carrier and/or an excipient.

18. A method for treating a tumor, and/or delaying tumor progression, and/or reducing or inhibiting tumor recurrence, in a subject, wherein the tumor is CLDN18.2 positive, the method comprising administering to the subject in need thereof an effective amount of the pharmaceutical composition of claim 15.

19. The method according to claim 18, which further comprises administering a second therapy to the subject, the second therapy being selected from the group consisting of surgery, chemotherapy, radiation therapy, immunotherapy, gene therapy, DNA therapy, RNA therapy, nanotherapy, viral therapy, adjuvant therapy, and any combination thereof.

20. The method according to claim 18, wherein the tumor is a solid tumor, a hematological tumor, or a metastatic, refractory or recurrent lesion of cancer.

21. A method of detecting the presence or level of CLDN18.2 in a sample, comprising contacting the sample with the antibody or antigen binding fragment thereof of claim 1 under conditions which permit formation of a complex between the antibody or antigen binding fragment thereof and CLDN 18.2, and detecting the formation of a complex between the antibody or antigen binding fragment thereof and CLDN 18.2.

22. A method for diagnosing or differentially diagnosing a CLDN18.2 positive tumors or tumor metastasis, comprising using the antibody or antigen binding fragment thereof of claim 1 or a conjugate or multispecific antibody comprising the antibody or antigen binding fragment thereof wherein the tumor is selected from gastric cancer, gastroesophageal junction (GEJ) adenocarcinoma, esophageal cancer, gastrointestinal cancer, pancreatic cancer, and lung cancer.

23. The antibody or antigen-binding fragment thereof of claim 6, comprising a heavy chain constant region (CH) having a sequence as set forth in SEQ ID NO: 42 and a light chain constant region (CL) having a sequence as set forth in SEQ ID NO: 43.

24. The pharmaceutical composition of claim 15, which further comprises an additional pharmaceutically active agent having antitumor activity.

25. The pharmaceutical composition of claim 24, wherein the additional pharmaceutically active agent is interferon, interleukin-2 or a chemotherapy drug.

26. The pharmaceutical composition of claim 25, wherein the additional pharmaceutically active agent is one or more agents selected from the group consisting of epirubicin, oxaliplatin, capecitabine, 5-fluorouracil, leucovorin, paclitaxel, albumin-bound paclitaxel, combination of epirubicin+oxaliplatin+5-fluorouracil, FOLFOX4, FOLFOX6, and mFOLFOX6.

27. The antibody or antigen binding fragment thereof of claim 1, wherein the CDR is defined according to Kabat, IMGT, Chothia or AbM numbering system.

28. The antibody or antigen binding fragment thereof of claim 1 or 2, wherein the VH and/or VL of the antibody or antigen binding fragment thereof comprises Framework Regions (FR) derived from a human or a mouse immunoglobulin.

29. The antibody or antigen binding fragment thereof of claim 1 or 2, wherein the antibody or antigen binding fragment thereof binds to human CLDN 18.2.

30. The antibody or antigen binding fragment thereof of claim 6, wherein the heavy chain constant region is an IgG heavy chain constant region, and wherein the antibody or antigen-binding fragment thereof comprises a heavy chain constant region selected from the group consisting of:
  (1) a human IgG 1 heavy chain constant region; and
  (2) a human IgG4 heavy chain constant region.

31. The antibody or antigen binding fragment thereof of claim 6, wherein:
  (1) the antibody or antigen binding fragment thereof comprises a heavy chain constant region (CH) having a sequence as set forth in SEQ ID NO: 42 or a variant thereof, the variant comprises a conservative substitution of up to 20 amino acids; and/or
  (2) the antibody or antigen binding fragment thereof comprises a light chain constant region (CL) having a sequence as set forth in SEQ ID NO: 43 or a variant thereof, the variant comprises a conservative substitution of up to 20 amino acids; or
  (3) the antibody or antigen binding fragment thereof comprises a heavy chain constant region (CH) having a sequence as set forth in SEQ ID NO: 42 and a light chain constant region (CL) having a sequence as set forth in SEQ ID NO: 43.

32. The antibody or antigen binding fragment thereof of claim 10, wherein the antibody or antigen binding fragment thereof comprises a detectable label.

33. The antibody or antigen binding fragment thereof of claim 27, wherein the detectable label is selected from an enzyme, a radioactive isotope, a fluorescent substance, a luminescent substance, and biotin.

34. The antibody or antigen binding fragment thereof according to claim 11, wherein the KD value is determined by Biofilm Interference Technology (BLI).

35. The antibody or antigen binding fragment thereof according to claim 11, wherein the EC50 is determined by flow cytometry or by a competitive ELISA technique.

36. The method according to claim 19, wherein the second therapy can be administered separately, in combination, simultaneously or sequentially with the method.

37. The method according to claim 20, wherein the tumor is selected from the group consisting of esophageal cancer, gastrointestinal cancer, pancreatic cancer, thyroid cancer, colorectal cancer, kidney cancer, lung cancer, liver cancer, stomach cancer, gastroesophageal junction (GEJ) adenocarcinoma, head and neck cancer, bladder cancer, breast cancer, uterine cancer, cervical cancer, ovarian cancer, prostate cancer, testicular cancer, germ cell cancer, bone cancer, skin cancer, thymic cancer, cholangiocarcinoma, gallbladder cancer, melanoma, mesothelioma, lymphoma, myeloma, sarcoma, glioblastoma, and leukemia.

38. The method according to claim 20, where in the tumor is selected from the group consisting of gastric cancer, gastroesophageal junction (GEJ) adenocarcinoma, esophageal cancer, gastrointestinal cancer, pancreatic cancer, and lung cancer.

39. The method according to claim 20, wherein the tumor is gastric cancer.

40. The method according to claim 20, wherein the tumor is breast cancer.

41. The method according to claim 20, wherein the tumor is gastroesophageal junction (GEJ) adenocarcinoma.

42. The method according to claim 20, wherein the tumor is non-small cell lung cancer.

43. The method according to claim 20, wherein the tumor is pancreatic cancer.

* * * * *

UNITED STATES PATENT AND TRADEMARK OFFICE
CERTIFICATE OF CORRECTION

PATENT NO. : 12,297,265 B2
APPLICATION NO. : 17/295603
DATED : May 13, 2025
INVENTOR(S) : Haijun Tian et al.

Page 1 of 1

It is certified that error appears in the above-identified patent and that said Letters Patent is hereby corrected as shown below:

In the Claims

Claim 4, Column 127, Line 27, "and/or," should read as --and/or--.

Claim 4, Column 127, Line 34, "and/or," should read as --and/or--.

Claim 11, Column 128, Line 50, "CLDN18.1 CLDN18.1" should read as --CLDN18.1--.

Claim 30, Column 131, Line 3, "IgG 1" should read as --IgG1--.

Signed and Sealed this
Nineteenth Day of August, 2025

Coke Morgan Stewart
*Acting Director of the United States Patent and Trademark Office*

SEQUENCE LISTING

```
<160> NUMBER OF SEQ ID NOS: 111

<210> SEQ ID NO 1
<211> LENGTH: 118
<212> TYPE: PRT
<213> ORGANISM: Artificial Sequence
<220> FEATURE:
<223> OTHER INFORMATION: heavy chain variable region of mouse antibody
      1E9.2

<400> SEQUENCE: 1

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Ser Phe Ser Asn Ser
            20                  25                  30

Ala Met Ser Trp Val Arg Gln Thr Pro Glu Lys Arg Leu Glu Gly Val
        35                  40                  45

Ala Thr Ile Ser Ser Gly Asp Ser Tyr Thr Tyr Tyr Pro Asp Ser Val
    50                  55                  60
```

```
Lys Gly Arg Phe Thr Ile Ser Arg Asp Asn Ala Lys Asn Ser Leu Tyr
 65                  70                  75                  80

Leu Gln Met Ser Ser Leu Arg Ser Glu Asp Thr Ala Val Tyr Tyr Cys
                 85                  90                  95

Ala Arg Gln Gly Tyr Gly Asn Ala Leu Asp Tyr Trp Gly Gln Gly Thr
            100                 105                 110

Ser Val Thr Val Ser Ser
            115

<210> SEQ ID NO 2
<211> LENGTH: 113
<212> TYPE: PRT
<213> ORGANISM: Artificial Sequence
<220> FEATURE:
<223> OTHER INFORMATION: light chain variable region of mouse antibody
      1E9.2

<400> SEQUENCE: 2

Asp Ile Val Met Thr Gln Ser Pro Ser Ser Leu Thr Val Thr Ala Gly
  1               5                  10                  15

Glu Lys Val Thr Met Ser Cys Lys Ser Ser Gln Ser Leu Leu Asn Ser
                 20                  25                  30

Gly Asn Gln Lys Asn Tyr Leu Thr Trp Tyr Gln Gln Lys Pro Gly Gln
             35                  40                  45

Pro Pro Lys Leu Leu Ile Tyr Trp Ser Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Tyr Tyr Pro Leu Thr Phe Gly Ala Gly Thr Lys Leu Glu Leu
            100                 105                 110

Lys

<210> SEQ ID NO 3
<211> LENGTH: 117
<212> TYPE: PRT
<213> ORGANISM: Artificial Sequence
<220> FEATURE:
<223> OTHER INFORMATION: heavy chain variable region of mouse antibody
      2C6.9

<400> SEQUENCE: 3

Gln Val Gln Leu Lys Glu Ser Gly Pro Gly Leu Val Ala Pro Ser Gln
  1               5                  10                  15

Ser Leu Ser Ile Thr Cys Thr Val Ser Gly Phe Ser Leu Thr Arg Tyr
                 20                  25                  30

Gly Val Ser Trp Val Arg Gln Pro Pro Gly Lys Gly Leu Glu Trp Leu
             35                  40                  45

Gly Val Ile Trp Gly Asp Gly Asn Thr Asn Phe His Ser Phe Leu Lys
 50                  55                  60

Ser Arg Leu Ser Ile Ser Lys Asp Ser Ser Lys Ser Gln Val Phe Leu
 65                  70                  75                  80

Lys Leu Asn Ser Leu Gln Thr Asp Asp Thr Ala Thr Tyr Tyr Cys Ala
                 85                  90                  95

Arg Val Asn Phe Gly Asn Ala Leu Asp Tyr Trp Gly Gln Gly Thr Ser
            100                 105                 110

Val Thr Val Ser Ser
```

<210> SEQ ID NO 4
<211> LENGTH: 113
<212> TYPE: PRT
<213> ORGANISM: Artificial Sequence
<220> FEATURE:
<223> OTHER INFORMATION: light chain variable region of mouse antibody 2C6.9

<400> SEQUENCE: 4

```
Asp Ile Val Met Thr Gln Ser Pro Ser Ser Leu Thr Val Thr Ala Gly
1               5                   10                  15

Glu Glu Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Asp Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ser Glu Asp Leu Ala Val Tyr Tyr Cys Gln Asn
                85                  90                  95

Asp Phe Ile Phe Pro Leu Thr Phe Gly Ala Gly Thr Lys Leu Glu Leu
            100                 105                 110

Lys
```

<210> SEQ ID NO 5
<211> LENGTH: 8
<212> TYPE: PRT
<213> ORGANISM: Artificial Sequence
<220> FEATURE:
<223> OTHER INFORMATION: IMGT 1E9.2 CDR-H1

<400> SEQUENCE: 5

```
Gly Phe Ser Phe Ser Asn Ser Ala
1               5
```

<210> SEQ ID NO 6
<211> LENGTH: 8
<212> TYPE: PRT
<213> ORGANISM: Artificial Sequence
<220> FEATURE:
<223> OTHER INFORMATION: IMGT 1E9.2 CDR-H2

<400> SEQUENCE: 6

```
Ile Ser Ser Gly Asp Ser Tyr Thr
1               5
```

<210> SEQ ID NO 7
<211> LENGTH: 11
<212> TYPE: PRT
<213> ORGANISM: Artificial Sequence
<220> FEATURE:
<223> OTHER INFORMATION: IMGT 1E9.2 CDR-H3

<400> SEQUENCE: 7

```
Ala Arg Gln Gly Tyr Gly Asn Ala Leu Asp Tyr
1               5                   10
```

<210> SEQ ID NO 8
<211> LENGTH: 12
<212> TYPE: PRT

```
<213> ORGANISM: Artificial Sequence
<220> FEATURE:
<223> OTHER INFORMATION: IMGT 1E9.2 CDR-L1

<400> SEQUENCE: 8

Gln Ser Leu Leu Asn Ser Gly Asn Gln Lys Asn Tyr
1               5                   10

<210> SEQ ID NO 9
<211> LENGTH: 3
<212> TYPE: PRT
<213> ORGANISM: Artificial Sequence
<220> FEATURE:
<223> OTHER INFORMATION: IMGT 1E9.2 CDR-L2

<400> SEQUENCE: 9

Trp Ser Ser
1

<210> SEQ ID NO 10
<211> LENGTH: 9
<212> TYPE: PRT
<213> ORGANISM: Artificial Sequence
<220> FEATURE:
<223> OTHER INFORMATION: IMGT 1E9.2 CDR-L3

<400> SEQUENCE: 10

Gln Asn Asp Tyr Tyr Tyr Pro Leu Thr
1               5

<210> SEQ ID NO 11
<211> LENGTH: 8
<212> TYPE: PRT
<213> ORGANISM: Artificial Sequence
<220> FEATURE:
<223> OTHER INFORMATION: IMGT 2C6.9/2C6.9-hz11/2C6.9-hz21 CDR-H1

<400> SEQUENCE: 11

Gly Phe Ser Leu Thr Arg Tyr Gly
1               5

<210> SEQ ID NO 12
<211> LENGTH: 7
<212> TYPE: PRT
<213> ORGANISM: Artificial Sequence
<220> FEATURE:
<223> OTHER INFORMATION: IMGT 2C6.9/2C6.9-hz11 CDR-H2

<400> SEQUENCE: 12

Ile Trp Gly Asp Gly Asn Thr
1               5

<210> SEQ ID NO 13
<211> LENGTH: 11
<212> TYPE: PRT
<213> ORGANISM: Artificial Sequence
<220> FEATURE:
<223> OTHER INFORMATION: IMGT 2C6.9/2C6.9-hz11/2C6.9-hz21 CDR-H3

<400> SEQUENCE: 13

Ala Arg Val Asn Phe Gly Asn Ala Leu Asp Tyr
1               5                   10

<210> SEQ ID NO 14
<211> LENGTH: 12
<212> TYPE: PRT
<213> ORGANISM: Artificial Sequence
```

<220> FEATURE:
<223> OTHER INFORMATION: IMGT 2C6.9/2C6.9-hz11/2C6.9-hz21 CDR-L1

<400> SEQUENCE: 14

Gln Ser Leu Leu Asn Ser Gly Asn Gln Lys Asn Tyr
1               5                   10

<210> SEQ ID NO 15
<211> LENGTH: 3
<212> TYPE: PRT
<213> ORGANISM: Artificial Sequence
<220> FEATURE:
<223> OTHER INFORMATION: IMGT 2C6.9/2C6.9-hz11/2C6.9-hz21 CDR-L2

<400> SEQUENCE: 15

Trp Ala Ser
1

<210> SEQ ID NO 16
<211> LENGTH: 9
<212> TYPE: PRT
<213> ORGANISM: Artificial Sequence
<220> FEATURE:
<223> OTHER INFORMATION: IMGT 2C6.9/2C6.9-hz11/2C6.9-hz21 CDR-L3

<400> SEQUENCE: 16

Gln Asn Asp Phe Ile Phe Pro Leu Thr
1               5

<210> SEQ ID NO 17
<211> LENGTH: 10
<212> TYPE: PRT
<213> ORGANISM: Artificial Sequence
<220> FEATURE:
<223> OTHER INFORMATION: AbM 1E9.2 CDR-H1

<400> SEQUENCE: 17

Gly Phe Ser Phe Ser Asn Ser Ala Met Ser
1               5                   10

<210> SEQ ID NO 18
<211> LENGTH: 10
<212> TYPE: PRT
<213> ORGANISM: Artificial Sequence
<220> FEATURE:
<223> OTHER INFORMATION: AbM 1E9.2 CDR-H2

<400> SEQUENCE: 18

Thr Ile Ser Ser Gly Asp Ser Tyr Thr Tyr
1               5                   10

<210> SEQ ID NO 19
<211> LENGTH: 9
<212> TYPE: PRT
<213> ORGANISM: Artificial Sequence
<220> FEATURE:
<223> OTHER INFORMATION: AbM 1E9.2 CDR-H3

<400> SEQUENCE: 19

Gln Gly Tyr Gly Asn Ala Leu Asp Tyr
1               5

<210> SEQ ID NO 20
<211> LENGTH: 17
<212> TYPE: PRT
<213> ORGANISM: Artificial Sequence
<220> FEATURE:

<223> OTHER INFORMATION: AbM 1E9.2 CDR-L1

<400> SEQUENCE: 20

Lys Ser Ser Gln Ser Leu Leu Asn Ser Gly Asn Gln Lys Asn Tyr Leu
1               5                   10                  15
Thr

<210> SEQ ID NO 21
<211> LENGTH: 7
<212> TYPE: PRT
<213> ORGANISM: Artificial Sequence
<220> FEATURE:
<223> OTHER INFORMATION: AbM 1E9.2 CDR-L2

<400> SEQUENCE: 21

Trp Ser Ser Thr Arg Glu Ser
1               5

<210> SEQ ID NO 22
<211> LENGTH: 9
<212> TYPE: PRT
<213> ORGANISM: Artificial Sequence
<220> FEATURE:
<223> OTHER INFORMATION: AbM 1E9.2 CDR-L3

<400> SEQUENCE: 22

Gln Asn Asp Tyr Tyr Tyr Pro Leu Thr
1               5

<210> SEQ ID NO 23
<211> LENGTH: 10
<212> TYPE: PRT
<213> ORGANISM: Artificial Sequence
<220> FEATURE:
<223> OTHER INFORMATION: AbM 2C6.9/2C6.9-hz11/2C6.9-hz21 CDR-H1

<400> SEQUENCE: 23

Gly Phe Ser Leu Thr Arg Tyr Gly Val Ser
1               5                   10

<210> SEQ ID NO 24
<211> LENGTH: 9
<212> TYPE: PRT
<213> ORGANISM: Artificial Sequence
<220> FEATURE:
<223> OTHER INFORMATION: AbM 2C6.9/2C6.9-hz11 CDR-H2

<400> SEQUENCE: 24

Val Ile Trp Gly Asp Gly Asn Thr Asn
1               5

<210> SEQ ID NO 25
<211> LENGTH: 9
<212> TYPE: PRT
<213> ORGANISM: Artificial Sequence
<220> FEATURE:
<223> OTHER INFORMATION: AbM 2C6.9/2C6.9-hz11/2C6.9-hz21 CDR-H3

<400> SEQUENCE: 25

Val Asn Phe Gly Asn Ala Leu Asp Tyr
1               5

<210> SEQ ID NO 26
<211> LENGTH: 17
<212> TYPE: PRT
<213> ORGANISM: Artificial Sequence

```
<220> FEATURE:
<223> OTHER INFORMATION: AbM 2C6.9/2C6.9-hz11/2C6.9-hz21 CDR-L1

<400> SEQUENCE: 26

Lys Ser Ser Gln Ser Leu Leu Asn Ser Gly Asn Gln Lys Asn Tyr Leu
1               5                   10                  15
Thr

<210> SEQ ID NO 27
<211> LENGTH: 7
<212> TYPE: PRT
<213> ORGANISM: Artificial Sequence
<220> FEATURE:
<223> OTHER INFORMATION: AbM 2C6.9/2C6.9-hz11/2C6.9-hz21 CDR-L2

<400> SEQUENCE: 27

Trp Ala Ser Thr Arg Asp Ser
1               5

<210> SEQ ID NO 28
<211> LENGTH: 9
<212> TYPE: PRT
<213> ORGANISM: Artificial Sequence
<220> FEATURE:
<223> OTHER INFORMATION: AbM 2C6.9/2C6.9-hz11/2C6.9-hz21 CDR-L3

<400> SEQUENCE: 28

Gln Asn Asp Phe Ile Phe Pro Leu Thr
1               5

<210> SEQ ID NO 29
<211> LENGTH: 118
<212> TYPE: PRT
<213> ORGANISM: Artificial Sequence
<220> FEATURE:
<223> OTHER INFORMATION: heavy chain variable region of humanized
      antibody
      1E9.2hz11/1E9.2hz12/1E9.2hz13/1E9.2hz14/1E9.2hz15/1E9.2hz17

<400> SEQUENCE: 29

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asn Ser
            20                  25                  30

Ala Met Ser Trp Val Arg Gln Ala Pro Gly Lys Gly Leu Glu Trp Val
        35                  40                  45

Ser Thr Ile Ser Ser Gly Asp Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Tyr Gly Asn Ala Leu Asp Tyr Trp Gly Gln Gly Thr
            100                 105                 110

Leu Val Thr Val Ser Ser
        115

<210> SEQ ID NO 30
<211> LENGTH: 118
<212> TYPE: PRT
<213> ORGANISM: Artificial Sequence
<220> FEATURE:
<223> OTHER INFORMATION: heavy chain variable region of humanized
``` antibody 1E9.2hz21

<400> SEQUENCE: 30

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asn Ser
            20                  25                  30

Ala Met Ser Trp Val Arg Gln Ala Pro Gly Lys Gly Leu Glu Gly Val
        35                  40                  45

Ser Thr Ile Ser Ser Gly Asp Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Tyr Gly Asn Ala Leu Asp Tyr Trp Gly Gln Gly Thr
            100                 105                 110

Leu Val Thr Val Ser Ser
        115

<210> SEQ ID NO 31
<211> LENGTH: 118
<212> TYPE: PRT
<213> ORGANISM: Artificial Sequence
<220> FEATURE:
<223> OTHER INFORMATION: heavy chain variable region of humanized
      antibody 1E9.2hz31

<400> SEQUENCE: 31

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asn Ser
            20                  25                  30

Ala Met Ser Trp Val Arg Gln Ala Pro Gly Lys Gly Leu Glu Gly Val
        35                  40                  45

Ala Thr Ile Ser Ser Gly Asp Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Tyr Gly Asn Ala Leu Asp Tyr Trp Gly Gln Gly Thr
            100                 105                 110

Leu Val Thr Val Ser Ser
        115

<210> SEQ ID NO 32
<211> LENGTH: 118
<212> TYPE: PRT
<213> ORGANISM: Artificial Sequence
<220> FEATURE:
<223> OTHER INFORMATION: heavy chain variable region of humanized
      antibody 1E9.2hz41

<400> SEQUENCE: 32

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asn Ser
            20                  25                  30

Ala Met Ser Trp Val Arg Gln Ala Pro Gly Lys Gly Leu Glu Gly Val
            35                  40                  45

Ala Thr Ile Ser Ser Gly Asp Ser Tyr Thr Tyr Tyr Pro Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Tyr Gly Asn Ala Leu Asp Tyr Trp Gly Gln Gly Thr
            100                 105                 110

Leu Val Thr Val Ser Ser
            115

<210> SEQ ID NO 33
<211> LENGTH: 113
<212> TYPE: PRT
<213> ORGANISM: Artificial Sequence
<220> FEATURE:
<223> OTHER INFORMATION: light chain variable region of humanized
      antibody 1E9.2hz11/1E9.2hz21/1E9.2hz31/1E9.2hz41

<400> SEQUENCE: 33

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ser Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Phe Ala Val Tyr Tyr Cys Gln Asn
                85                  90                  95

Asp Tyr Tyr Tyr Pro Leu Thr Phe Gly Gly Gly Thr Lys Val Glu Ile
            100                 105                 110

Lys

<210> SEQ ID NO 34
<211> LENGTH: 113
<212> TYPE: PRT
<213> ORGANISM: Artificial Sequence
<220> FEATURE:
<223> OTHER INFORMATION: light chain variable region of humanized
      antibody 1E9.2hz12

<400> SEQUENCE: 34

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Gln Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ser Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

```
Ile Ser Ser Leu Gln Ala Glu Asp Phe Ala Val Tyr Tyr Cys Gln Asn
                85                  90                  95

Asp Tyr Tyr Tyr Pro Leu Thr Phe Gly Gly Gly Thr Lys Val Glu Ile
            100                 105                 110

Lys

<210> SEQ ID NO 35
<211> LENGTH: 113
<212> TYPE: PRT
<213> ORGANISM: Artificial Sequence
<220> FEATURE:
<223> OTHER INFORMATION: light chain variable region of humanized
      antibody 1E9.2hz13

<400> SEQUENCE: 35

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Gln Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ser Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Tyr Tyr Pro Leu Thr Phe Gly Gly Gly Thr Lys Val Glu Ile
            100                 105                 110

Lys

<210> SEQ ID NO 36
<211> LENGTH: 113
<212> TYPE: PRT
<213> ORGANISM: Artificial Sequence
<220> FEATURE:
<223> OTHER INFORMATION: light chain variable region of humanized
      antibody 1E9.2hz14

<400> SEQUENCE: 36

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Gln Ser
                20                  25                  30

Gly Asn Asn Lys Asn Tyr Leu Thr Trp Tyr Gln Gln Lys Pro Gly Gln
            35                  40                  45

Pro Pro Lys Leu Leu Ile Tyr Trp Ser Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Phe Ala Val Tyr Tyr Cys Gln Asn
                85                  90                  95

Asp Tyr Tyr Tyr Pro Leu Thr Phe Gly Gly Gly Thr Lys Val Glu Ile
            100                 105                 110

Lys

<210> SEQ ID NO 37
<211> LENGTH: 113
```

```
<212> TYPE: PRT
<213> ORGANISM: Artificial Sequence
<220> FEATURE:
<223> OTHER INFORMATION: light chain variable region of humanized
      antibody 1E9.2hz15

<400> SEQUENCE: 37
```

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Asn Ser
            20                  25                  30

Gly Asn Gln Lys Asn Tyr Leu Thr Trp Tyr Leu Gln Lys Pro Gly Gln
        35                  40                  45

Ser Pro Gln Leu Leu Ile Tyr Trp Ser Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Phe Gly Val Tyr Tyr Cys Gln Asn
                85                  90                  95

Asp Tyr Tyr Tyr Pro Leu Thr Phe Gly Gly Gly Thr Lys Val Glu Ile
                100                 105                 110

Lys

```
<210> SEQ ID NO 38
<211> LENGTH: 113
<212> TYPE: PRT
<213> ORGANISM: Artificial Sequence
<220> FEATURE:
<223> OTHER INFORMATION: light chain variable region of humanized
      antibody 1E9.2hz17

<400> SEQUENCE: 38
```

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Gln Ser
            20                  25                  30

Gly Asn Gly Lys Asn Tyr Leu Thr Trp Tyr Leu Gln Lys Pro Gly Gln
        35                  40                  45

Ser Pro Gln Leu Leu Ile Tyr Trp Ser Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Phe Gly Val Tyr Tyr Cys Gln Asn
                85                  90                  95

Asp Tyr Tyr Tyr Pro Leu Thr Phe Gly Gly Gly Thr Lys Val Glu Ile
                100                 105                 110

Lys

```
<210> SEQ ID NO 39
<211> LENGTH: 117
<212> TYPE: PRT
<213> ORGANISM: Artificial Sequence
<220> FEATURE:
<223> OTHER INFORMATION: Heavy chain variable region of humanized
      antibody 2C6.9hz11

<400> SEQUENCE: 39
```

Gln Val Gln Leu Gln Glu Ser Gly Pro Gly Leu Val Lys Pro Ser Glu
1               5                   10                  15

```
Thr Leu Ser Leu Thr Cys Thr Val Ser Gly Phe Ser Leu Thr Arg Tyr
            20                  25                  30

Gly Val Ser Trp Ile Arg Gln Pro Pro Gly Lys Gly Leu Glu Trp Ile
            35                  40                  45

Gly Val Ile Trp Gly Asp Gly Asn Thr Asn Tyr Asn Pro Ser Leu Lys
50                      55                  60

Ser Arg Val Thr Ile Ser Lys Asp Ser Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Val Asn Phe Gly Asn Ala Leu Asp Tyr Trp Gly Gln Gly Thr Leu
            100                 105                 110

Val Thr Val Ser Ser
            115

<210> SEQ ID NO 40
<211> LENGTH: 117
<212> TYPE: PRT
<213> ORGANISM: Artificial Sequence
<220> FEATURE:
<223> OTHER INFORMATION: heavy chain variable region of humanized
      antibody 2C6.9hz21

<400> SEQUENCE: 40

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Arg Tyr
            20                  25                  30

Gly Val Ser Trp Ile Arg Gln Pro Pro Gly Lys Gly Leu Glu Trp Ile
            35                  40                  45

Gly Val Ile Trp Gly Glu Gly Asn Thr Asn Tyr Asn Pro Ser Leu Lys
50                      55                  60

Ser Arg Val Thr Ile Ser Lys Asp Ser Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Val Asn Phe Gly Asn Ala Leu Asp Tyr Trp Gly Gln Gly Thr Leu
            100                 105                 110

Val Thr Val Ser Ser
            115

<210> SEQ ID NO 41
<211> LENGTH: 113
<212> TYPE: PRT
<213> ORGANISM: Artificial Sequence
<220> FEATURE:
<223> OTHER INFORMATION: light chain variable region of humanized
      antibody 2C6.9hz11/2C6.9hz21

<400> SEQUENCE: 41

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Asp Ser Gly Val
50                      55                  60
```

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
            85                  90                  95

Asp Phe Ile Phe Pro Leu Thr Phe Gly Gly Gly Thr Lys Val Glu Ile
        100                 105                 110

Lys

<210> SEQ ID NO 42
<211> LENGTH: 330
<212> TYPE: PRT
<213> ORGANISM: Artificial Sequence
<220> FEATURE:
<223> OTHER INFORMATION: human IgG1 heavy chain constant region

<400> SEQUENCE: 42

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr

```
                305                 310                 315                 320

Gln Lys Ser Leu Ser Leu Ser Pro Gly Lys
                325                 330

<210> SEQ ID NO 43
<211> LENGTH: 107
<212> TYPE: PRT
<213> ORGANISM: Artificial Sequence
<220> FEATURE:
<223> OTHER INFORMATION: human kappa light chain constant region

<400> SEQUENCE: 43

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 44
<211> LENGTH: 118
<212> TYPE: PRT
<213> ORGANISM: Artificial Sequence
<220> FEATURE:
<223> OTHER INFORMATION: heavy chain variable region sequence of mouse
      antibody 19H11.6

<400> SEQUENCE: 44

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Ser Phe Ser Asn Ser
            20                  25                  30

Ala Met Ser Trp Val Arg Gln Thr Pro Glu Lys Arg Leu Glu Gly Val
        35                  40                  45

Ala Thr Ile Ser Ser Gly Asp Ser Phe Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Ser Arg Leu Arg Ser Glu Asp Thr Ala Val Tyr Tyr Cys
                85                  90                  95

Ala Arg Gln Gly Tyr Gly Asn Ala Leu Asp Tyr Trp Gly Gln Gly Thr
            100                 105                 110

Ser Val Thr Val Ser Ser
        115

<210> SEQ ID NO 45
<211> LENGTH: 113
<212> TYPE: PRT
<213> ORGANISM: Artificial Sequence
<220> FEATURE:
<223> OTHER INFORMATION: light chain variable region sequence of mouse
      antibody 19H11.6
```

<400> SEQUENCE: 45

Asp Ile Val Met Thr Gln Ser Pro Ser Ser Leu Thr Val Thr Ala Gly
1               5                   10                  15

Glu Lys Val Thr Met Thr Cys Lys Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Tyr Tyr Pro Leu Thr Phe Gly Ala Gly Thr Lys Leu Glu Leu
                100                 105                 110

Lys

<210> SEQ ID NO 46
<211> LENGTH: 118
<212> TYPE: PRT
<213> ORGANISM: Artificial Sequence
<220> FEATURE:
<223> OTHER INFORMATION: heavy chain variable region sequence of mouse
      antibody 16A9.11

<400> SEQUENCE: 46

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Ser Phe Ser Asn Ser
            20                  25                  30

Ala Met Ser Trp Val Arg Gln Thr Pro Glu Lys Arg Leu Glu Gly Val
        35                  40                  45

Ala Thr Ile Ser Ser Gly Asp Ser Tyr Thr Tyr Tyr Pro Asp Ser Val
    50                  55                  60

Lys Gly Arg Phe Thr Ile Ser Arg Asp Thr Ala Lys Asn Ser Leu Tyr
65                  70                  75                  80

Leu Gln Met Ser Ser Leu Arg Ser Glu Asp Thr Ala Val Tyr Tyr Cys
                85                  90                  95

Thr Arg Gln Gly Tyr Gly Asn Ala Met Asp Tyr Trp Gly Gln Gly Thr
                100                 105                 110

Ser Val Thr Val Ser Ser
        115

<210> SEQ ID NO 47
<211> LENGTH: 113
<212> TYPE: PRT
<213> ORGANISM: Artificial Sequence
<220> FEATURE:
<223> OTHER INFORMATION: light chain variable region sequence of mouse
      antibody 16A9.11

<400> SEQUENCE: 47

Asp Ile Val Met Thr Gln Ser Pro Ser Ser Leu Thr Val Thr Ala Gly
1               5                   10                  15

Glu Lys Val Thr Met Ser Cys Lys Ser Gln Ser Leu Leu Asn Ser
            20                  25                  30

Gly Asn Gln Lys Asn Tyr Leu Thr Trp Tyr Gln Gln Lys Pro Gly Gln

```
                35                  40                  45
Pro Pro Lys Leu Leu Ile Tyr Trp Ser Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Tyr Tyr Pro Leu Thr Phe Gly Ala Gly Thr Lys Leu Glu Leu
                100                 105                 110

Lys

<210> SEQ ID NO 48
<211> LENGTH: 118
<212> TYPE: PRT
<213> ORGANISM: Artificial Sequence
<220> FEATURE:
<223> OTHER INFORMATION: heavy chain variable region sequence of mouse
      antibody 9C8.1

<400> SEQUENCE: 48

Gln Val Gln Leu Gln Gln Ser Gly Ala Glu Leu Val Arg Pro Gly Ser
 1               5                  10                  15

Ser Val Lys Ile Ser Cys Lys Ala Ser Gly Tyr Ala Phe Ser Asn Tyr
                 20                  25                  30

Trp Met Asn Trp Val Lys Gln Arg Pro Gly Gln Gly Leu Glu Trp Ile
                 35                  40                  45

Gly Gln Ile Tyr Pro Gly Asp Gly Asp Thr Asn Tyr Asn Gly Lys Phe
 50                  55                  60

Lys Gly Lys Ala Thr Leu Thr Thr Asp Lys Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Leu Tyr Tyr Gly Asn Ser Phe Ala Tyr Trp Gly Gln Gly Thr
                100                 105                 110

Leu Val Thr Val Ser Ser
        115

<210> SEQ ID NO 49
<211> LENGTH: 113
<212> TYPE: PRT
<213> ORGANISM: Artificial Sequence
<220> FEATURE:
<223> OTHER INFORMATION: light chain variable region sequence of mouse
      antibody 9C8.1

<400> SEQUENCE: 49

Asp Ile Val Met Thr Gln Ser Pro Ser Ser Leu Thr Val Thr Ala Gly
 1               5                  10                  15

Glu Lys Val Thr Val Ser Cys Lys Ser Ser Gln Ser Leu Leu Asn Ser
                 20                  25                  30

Gly Asn Gln Lys Asn Tyr Leu Thr Trp Tyr Gln Gln Lys Pro Gly Gln
                 35                  40                  45

Pro Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Ala Asp Leu Ala Ile Tyr Tyr Cys Gln Asn
                 85                  90                  95
```

Asp Tyr Phe Tyr Pro Phe Thr Phe Gly Gly Gly Thr Lys Leu Glu Ile
                100                 105                 110

Lys

<210> SEQ ID NO 50
<211> LENGTH: 118
<212> TYPE: PRT
<213> ORGANISM: Artificial Sequence
<220> FEATURE:
<223> OTHER INFORMATION: heavy chain variable region sequence of mouse
      antibody 6B9.22

<400> SEQUENCE: 50

Gln Val Gln Leu Gln Gln Ser Gly Ala Glu Leu Val Lys Pro Gly Ala
1               5                   10                  15

Ser Val Lys Met Ser Cys Lys Ala Phe Gly Tyr Thr Phe Thr Ser Tyr
            20                  25                  30

Pro Ile Glu Trp Met Lys Gln Asn His Gly Lys Ser Leu Glu Trp Ile
        35                  40                  45

Gly Asn Phe His Pro Tyr Asn Asp Asp Thr Lys Tyr Asn Glu Lys Phe
50                  55                  60

Lys Gly Lys Ala Lys Leu Thr Val Glu Lys Ser Ser Thr Val Tyr
65                  70                  75                  80

Leu Glu Leu Ser Arg Leu Thr Ser Asp Ser Ala Val Tyr Tyr Cys
                85                  90                  95

Ala Arg Thr Tyr Tyr Gly Asn Ser Phe Ala Tyr Trp Gly Gln Gly Thr
            100                 105                 110

Leu Val Thr Val Ser Ser
        115

<210> SEQ ID NO 51
<211> LENGTH: 113
<212> TYPE: PRT
<213> ORGANISM: Artificial Sequence
<220> FEATURE:
<223> OTHER INFORMATION: light chain variable region sequence of mouse
      antibody 6B9.22

<400> SEQUENCE: 51

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Ser Arg Asp Ser Gly Val
50                  55                  60

Pro His Arg Phe Thr Gly Ser Gly Ser Gly Thr Asp Phe Thr Leu Thr
65                  70                  75                  80

Ile Ser Ser Val Gln Ala Glu Asp Leu Ala Phe Tyr Tyr Cys Gln Asn
                85                  90                  95

Asp Tyr Phe Tyr Pro Phe Thr Phe Gly Ala Gly Thr Lys Leu Glu Leu
            100                 105                 110

Lys

<210> SEQ ID NO 52
<211> LENGTH: 118
<212> TYPE: PRT

<213> ORGANISM: Artificial Sequence
<220> FEATURE:
<223> OTHER INFORMATION: heavy chain variable region sequence of mouse
      antibody 19G10.14

<400> SEQUENCE: 52

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Phe Thr Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Ser Thr Asp Tyr Asn Ala Ala Leu Met
    50                  55                  60

Ser Arg Leu Ser Ile Arg Lys Asp Asn Ser Lys Ser Gln Val Phe Leu
65                  70                  75                  80

Lys Met Asn Ser Leu Gln Ile Ala Asp Thr Ala Met Tyr Tyr Cys Ala
                85                  90                  95

Arg Asp Gly His Gly Lys Val Gly Phe Asp Val Trp Gly Ala Gly Thr
            100                 105                 110

Thr Val Thr Val Ser Ser
            115

<210> SEQ ID NO 53
<211> LENGTH: 113
<212> TYPE: PRT
<213> ORGANISM: Artificial Sequence
<220> FEATURE:
<223> OTHER INFORMATION: light chain variable region sequence of mouse
      antibody 19G10.14

<400> SEQUENCE: 53

Asp Ile Val Met Thr Gln Ser Pro Ser Ser Leu Ser Val Ser Ala Gly
1               5                   10                  15

Glu Lys Val Thr Met Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Gly Ser Gly Thr Asp Phe Thr Leu Thr
65                  70                  75                  80

Ile Ser Ser Val Gln Ala Glu Asp Leu Ala Ile Tyr Tyr Cys Gln Asn
                85                  90                  95

Asp His Phe Tyr Pro Phe Thr Phe Gly Ser Gly Thr Lys Leu Glu Ile
            100                 105                 110

Lys

<210> SEQ ID NO 54
<211> LENGTH: 354
<212> TYPE: DNA
<213> ORGANISM: Artificial Sequence
<220> FEATURE:
<223> OTHER INFORMATION: heavy chain variable region sequence of mouse
      antibody 1E9.2

<400> SEQUENCE: 54
gaagtgatgc tggtggagtc tgggggaggc ttagtgaagc ctggagggtc cctgaaactc     60
tcctgtgcag cctctggatt cagtttcagt aactctgcca tgtcttgggt tcgccagact    120

```
ccggagaaga ggctggaggg ggtcgcaacc attagtagtg gtgatagtta cacctactat    180
ccagacagtg tgaaggggcg attcaccatc tccagagaca tgccaagaa cagcctatac     240 ctgcaaatga gcagtctgag gtctgaggac acggccgtgt attactgtgc aagacagggg    300
tatggcaatg ctttggacta ctggggtcaa ggaacctcag tcaccgtctc ctca          354
```

<210> SEQ ID NO 55
<211> LENGTH: 339
<212> TYPE: DNA
<213> ORGANISM: Artificial Sequence
<220> FEATURE:
<223> OTHER INFORMATION: light chain variable region sequence of mouse antibody 1E9.2

<400> SEQUENCE: 55

```
gacattgtga tgacccagtc tccatcctcc ctgactgtga cagcaggaga aaggtcact     60 atgagctgca gtccagtca gagtctgtta aatagtggaa atcaaaagaa ctacttgacc     120
tggtaccagc agaaaccagg gcagcctcct aaattgttga tctactggtc atccactagg    180
gaatcggggg tccctgatcg cttcacaggc agtggatctg gaacagattt cactctcacc    240
atcagcagtg tgcaggctga agacctggca gtttattact gtcagaatga ttattattat    300
ccactcacgt tcggtgctgg gaccaagctg gagctgaaa                            339
```

<210> SEQ ID NO 56
<211> LENGTH: 351
<212> TYPE: DNA
<213> ORGANISM: Artificial Sequence
<220> FEATURE:
<223> OTHER INFORMATION: heavy chain variable region sequence of mouse antibody 2C6.9

<400> SEQUENCE: 56

```
caggtgcagc tgaaggagtc aggacctggc ctggtggcgc cctcacagag cctgtccatc    60
acatgcactg tctcagggtt ctctttaacc agatatggtg tgagctgggt tcgccagccc    120
ccaggaaagg gtctggagtg gctgggggta atatgggggtg acgggaatac aaattttcat   180
tcatttctta aatccagact gagcatcagt aaggatagcc ccaagagcca gttttctta    240 aaactgaaca gtctgcaaac tgatgacaca gccacatatt actgtgccag agttaactt    300 ggtaacgctt tggactactg gggtcaagga acctcagtca ccgtctcctc a             351
```

<210> SEQ ID NO 57
<211> LENGTH: 339
<212> TYPE: DNA
<213> ORGANISM: Artificial Sequence
<220> FEATURE:
<223> OTHER INFORMATION: light chain variable region sequence of mouse antibody 2C6.9

<400> SEQUENCE: 57

```
gacattgtga tgacccagtc tccatcctcc ctgactgtga cagcaggaga ggaggtcact    60
atgagctgca gtccagtca gagtctgtta acagtggaa atcaaaagaa ctacttgacc      120
tggtaccagc agaaaccagg gcagcctcct aaactgttga tctactgggc tccactagg     180 gattctgggg tccctgatcg cttcacaggc agtggatctg gaacagattt cactctcacc    240
atcagcagtg tgcagtctga agacctggca gtttattact gtcagaatga ctttattttt    300
ccgctcacgt tcggtgctgg gaccaagctg gagctgaaa                            339
```

<210> SEQ ID NO 58
<211> LENGTH: 10
<212> TYPE: PRT
<213> ORGANISM: Artificial Sequence
<220> FEATURE:
<223> OTHER INFORMATION: AbM 19H11.6/16A9.11 CDR-H1

<400> SEQUENCE: 58

Gly Phe Ser Phe Ser Asn Ser Ala Met Ser
1               5                   10

<210> SEQ ID NO 59
<211> LENGTH: 10
<212> TYPE: PRT
<213> ORGANISM: Artificial Sequence
<220> FEATURE:
<223> OTHER INFORMATION: AbM 9C8.1 CDR-H1

<400> SEQUENCE: 59

Gly Tyr Ala Phe Ser Asn Tyr Trp Met Asn
1               5                   10

<210> SEQ ID NO 60
<211> LENGTH: 10
<212> TYPE: PRT
<213> ORGANISM: Artificial Sequence
<220> FEATURE:
<223> OTHER INFORMATION: AbM 6B9.22 CDR-H1

<400> SEQUENCE: 60

Gly Tyr Thr Phe Thr Ser Tyr Pro Ile Glu
1               5                   10

<210> SEQ ID NO 61
<211> LENGTH: 10
<212> TYPE: PRT
<213> ORGANISM: Artificial Sequence
<220> FEATURE:
<223> OTHER INFORMATION: AbM 19G10.14 CDR-H1

<400> SEQUENCE: 61

Gly Phe Ser Phe Thr Ser Tyr Gly Val His
1               5                   10

<210> SEQ ID NO 62
<211> LENGTH: 10
<212> TYPE: PRT
<213> ORGANISM: Artificial Sequence
<220> FEATURE:
<223> OTHER INFORMATION: AbM 19H11.6 CDR-H2

<400> SEQUENCE: 62

Thr Ile Ser Ser Gly Asp Ser Phe Thr Tyr
1               5                   10

<210> SEQ ID NO 63
<211> LENGTH: 10
<212> TYPE: PRT
<213> ORGANISM: Artificial Sequence
<220> FEATURE:
<223> OTHER INFORMATION: AbM 16A9.11 CDR-H2

<400> SEQUENCE: 63

Thr Ile Ser Ser Gly Asp Ser Tyr Thr Tyr
1               5                   10

<210> SEQ ID NO 64

```
<211> LENGTH: 10
<212> TYPE: PRT
<213> ORGANISM: Artificial Sequence
<220> FEATURE:
<223> OTHER INFORMATION: AbM  9C8.1 CDR-H2

<400> SEQUENCE: 64

Gln Ile Tyr Pro Gly Asp Gly Asp Thr Asn
1               5                   10

<210> SEQ ID NO 65
<211> LENGTH: 10
<212> TYPE: PRT
<213> ORGANISM: Artificial Sequence
<220> FEATURE:
<223> OTHER INFORMATION: AbM  6B9.22 CDR-H2

<400> SEQUENCE: 65

Asn Phe His Pro Tyr Asn Asp Asp Thr Lys
1               5                   10

<210> SEQ ID NO 66
<211> LENGTH: 9
<212> TYPE: PRT
<213> ORGANISM: Artificial Sequence
<220> FEATURE:
<223> OTHER INFORMATION: AbM  19G10.14 CDR-H2

<400> SEQUENCE: 66

Val Ile Trp Ala Gly Gly Ser Thr Asp
1               5

<210> SEQ ID NO 67
<211> LENGTH: 9
<212> TYPE: PRT
<213> ORGANISM: Artificial Sequence
<220> FEATURE:
<223> OTHER INFORMATION: AbM  19H11.6 CDR-H3

<400> SEQUENCE: 67

Gln Gly Tyr Gly Asn Ala Leu Asp Tyr
1               5

<210> SEQ ID NO 68
<211> LENGTH: 9
<212> TYPE: PRT
<213> ORGANISM: Artificial Sequence
<220> FEATURE:
<223> OTHER INFORMATION: AbM  16A9.11 CDR-H3

<400> SEQUENCE: 68

Gln Gly Tyr Gly Asn Ala Met Asp Tyr
1               5

<210> SEQ ID NO 69
<211> LENGTH: 9
<212> TYPE: PRT
<213> ORGANISM: Artificial Sequence
<220> FEATURE:
<223> OTHER INFORMATION: AbM  9C8.1 CDR-H3

<400> SEQUENCE: 69

Leu Tyr Tyr Gly Asn Ser Phe Ala Tyr
1               5

<210> SEQ ID NO 70
<211> LENGTH: 9
```

```
<212> TYPE: PRT
<213> ORGANISM: Artificial Sequence
<220> FEATURE:
<223> OTHER INFORMATION: AbM  6B9.22 CDR-H3

<400> SEQUENCE: 70

Thr Tyr Tyr Gly Asn Ser Phe Ala Tyr
1               5

<210> SEQ ID NO 71
<211> LENGTH: 10
<212> TYPE: PRT
<213> ORGANISM: Artificial Sequence
<220> FEATURE:
<223> OTHER INFORMATION: AbM  19G10.14 CDR-H3

<400> SEQUENCE: 71

Asp Gly His Gly Lys Val Gly Phe Asp Val
1               5                   10

<210> SEQ ID NO 72
<211> LENGTH: 17
<212> TYPE: PRT
<213> ORGANISM: Artificial Sequence
<220> FEATURE:
<223> OTHER INFORMATION: AbM 19H11.6/16A9.11/9C8.1/6B9.22 CDR-L1

<400> SEQUENCE: 72

Lys Ser Ser Gln Ser Leu Leu Asn Ser Gly Asn Gln Lys Asn Tyr Leu
1               5                   10                  15

Thr

<210> SEQ ID NO 73
<211> LENGTH: 17
<212> TYPE: PRT
<213> ORGANISM: Artificial Sequence
<220> FEATURE:
<223> OTHER INFORMATION: AbM 19G10.14 CDR-L1

<400> SEQUENCE: 73

Lys Ser Ser Gln Ser Leu Leu Asn Ser Gly Asn Gln Lys Asn Tyr Leu
1               5                   10                  15

Ala

<210> SEQ ID NO 74
<211> LENGTH: 7
<212> TYPE: PRT
<213> ORGANISM: Artificial Sequence
<220> FEATURE:
<223> OTHER INFORMATION: AbM 19H11.6/16A9.11 CDR-L2

<400> SEQUENCE: 74

Trp Ser Ser Thr Arg Glu Ser
1               5

<210> SEQ ID NO 75
<211> LENGTH: 7
<212> TYPE: PRT
<213> ORGANISM: Artificial Sequence
<220> FEATURE:
<223> OTHER INFORMATION: AbM 9C8.1 CDR-L2

<400> SEQUENCE: 75

Trp Ala Ser Thr Arg Glu Ser
1               5
```

```
<210> SEQ ID NO 76
<211> LENGTH: 7
<212> TYPE: PRT
<213> ORGANISM: Artificial Sequence
<220> FEATURE:
<223> OTHER INFORMATION: AbM 6B9.22 CDR-L2

<400> SEQUENCE: 76

Trp Ala Ser Ser Arg Asp Ser
1               5

<210> SEQ ID NO 77
<211> LENGTH: 7
<212> TYPE: PRT
<213> ORGANISM: Artificial Sequence
<220> FEATURE:
<223> OTHER INFORMATION: AbM 19G10.14 CDR-L2

<400> SEQUENCE: 77

Gly Ala Ser Thr Arg Glu Ser
1               5

<210> SEQ ID NO 78
<211> LENGTH: 9
<212> TYPE: PRT
<213> ORGANISM: Artificial Sequence
<220> FEATURE:
<223> OTHER INFORMATION: AbM 19H11.6/16A9.11 CDR-L3

<400> SEQUENCE: 78

Gln Asn Asp Tyr Tyr Tyr Pro Leu Thr
1               5

<210> SEQ ID NO 79
<211> LENGTH: 9
<212> TYPE: PRT
<213> ORGANISM: Artificial Sequence
<220> FEATURE:
<223> OTHER INFORMATION: AbM 9C8.1/6B9.22 CDR-L3

<400> SEQUENCE: 79

Gln Asn Asp Tyr Phe Tyr Pro Phe Thr
1               5

<210> SEQ ID NO 80
<211> LENGTH: 9
<212> TYPE: PRT
<213> ORGANISM: Artificial Sequence
<220> FEATURE:
<223> OTHER INFORMATION: AbM 19G10.14 CDR-L3

<400> SEQUENCE: 80

Gln Asn Asp His Phe Tyr Pro Phe Thr
1               5

<210> SEQ ID NO 81
<211> LENGTH: 8
<212> TYPE: PRT
<213> ORGANISM: Artificial Sequence
<220> FEATURE:
<223> OTHER INFORMATION: IMGT 19H11.6/16A9.11 CDR-H1

<400> SEQUENCE: 81

Gly Phe Ser Phe Ser Asn Ser Ala
1               5
```

```
<210> SEQ ID NO 82
<211> LENGTH: 8
<212> TYPE: PRT
<213> ORGANISM: Artificial Sequence
<220> FEATURE:
<223> OTHER INFORMATION: IMGT 19H11.6 CDR-H2

<400> SEQUENCE: 82

Ile Ser Ser Gly Asp Ser Phe Thr
1               5

<210> SEQ ID NO 83
<211> LENGTH: 11
<212> TYPE: PRT
<213> ORGANISM: Artificial Sequence
<220> FEATURE:
<223> OTHER INFORMATION: IMGT 19H11.6 CDR-H3

<400> SEQUENCE: 83

Ala Arg Gln Gly Tyr Gly Asn Ala Leu Asp Tyr
1               5                   10

<210> SEQ ID NO 84
<211> LENGTH: 8
<212> TYPE: PRT
<213> ORGANISM: Artificial Sequence
<220> FEATURE:
<223> OTHER INFORMATION: IMGT 16A9.11 CDR-H2

<400> SEQUENCE: 84

Ile Ser Ser Gly Asp Ser Tyr Thr
1               5

<210> SEQ ID NO 85
<211> LENGTH: 11
<212> TYPE: PRT
<213> ORGANISM: Artificial Sequence
<220> FEATURE:
<223> OTHER INFORMATION: IMGT 16A9.11 CDR-H3

<400> SEQUENCE: 85

Thr Arg Gln Gly Tyr Gly Asn Ala Met Asp Tyr
1               5                   10

<210> SEQ ID NO 86
<211> LENGTH: 8
<212> TYPE: PRT
<213> ORGANISM: Artificial Sequence
<220> FEATURE:
<223> OTHER INFORMATION: IMGT 9C8.1 CDR-H1

<400> SEQUENCE: 86

Gly Tyr Ala Phe Ser Asn Tyr Trp
1               5

<210> SEQ ID NO 87
<211> LENGTH: 8
<212> TYPE: PRT
<213> ORGANISM: Artificial Sequence
<220> FEATURE:
<223> OTHER INFORMATION: IMGT 9C8.1 CDR-H2

<400> SEQUENCE: 87

Ile Tyr Pro Gly Asp Gly Asp Thr
1               5

<210> SEQ ID NO 88
```

```
<211> LENGTH: 11
<212> TYPE: PRT
<213> ORGANISM: Artificial Sequence
<220> FEATURE:
<223> OTHER INFORMATION: IMGT 9C8.1 CDR-H3

<400> SEQUENCE: 88

Ala Arg Leu Tyr Tyr Gly Asn Ser Phe Ala Tyr
1               5                   10

<210> SEQ ID NO 89
<211> LENGTH: 8
<212> TYPE: PRT
<213> ORGANISM: Artificial Sequence
<220> FEATURE:
<223> OTHER INFORMATION: IMGT 6B9.22 CDR-H1

<400> SEQUENCE: 89

Gly Tyr Thr Phe Thr Ser Tyr Pro
1               5

<210> SEQ ID NO 90
<211> LENGTH: 8
<212> TYPE: PRT
<213> ORGANISM: Artificial Sequence
<220> FEATURE:
<223> OTHER INFORMATION: IMGT 6B9.22 CDR-H2

<400> SEQUENCE: 90

Phe His Pro Tyr Asn Asp Asp Thr
1               5

<210> SEQ ID NO 91
<211> LENGTH: 11
<212> TYPE: PRT
<213> ORGANISM: Artificial Sequence
<220> FEATURE:
<223> OTHER INFORMATION: IMGT 6B9.22 CDR-H3

<400> SEQUENCE: 91

Ala Arg Thr Tyr Tyr Gly Asn Ser Phe Ala Tyr
1               5                   10

<210> SEQ ID NO 92
<211> LENGTH: 8
<212> TYPE: PRT
<213> ORGANISM: Artificial Sequence
<220> FEATURE:
<223> OTHER INFORMATION: IMGT 19G10.14 CDR-H1

<400> SEQUENCE: 92

Gly Phe Ser Phe Thr Ser Tyr Gly
1               5

<210> SEQ ID NO 93
<211> LENGTH: 7
<212> TYPE: PRT
<213> ORGANISM: Artificial Sequence
<220> FEATURE:
<223> OTHER INFORMATION: IMGT 19G10.14 CDR-H2

<400> SEQUENCE: 93

Ile Trp Ala Gly Gly Ser Thr
1               5

<210> SEQ ID NO 94
<211> LENGTH: 12
```

```
<212> TYPE: PRT
<213> ORGANISM: Artificial Sequence
<220> FEATURE:
<223> OTHER INFORMATION: IMGT 19G10.14 CDR-H3

<400> SEQUENCE: 94

Ala Arg Asp Gly His Gly Lys Val Gly Phe Asp Val
1               5                   10

<210> SEQ ID NO 95
<211> LENGTH: 12
<212> TYPE: PRT
<213> ORGANISM: Artificial Sequence
<220> FEATURE:
<223> OTHER INFORMATION: IMGT 19H11.6/16A9.11/9C8.1/6B9.22/19G10.14
      CDR-L1

<400> SEQUENCE: 95

Gln Ser Leu Leu Asn Ser Gly Asn Gln Lys Asn Tyr
1               5                   10

<210> SEQ ID NO 96
<211> LENGTH: 3
<212> TYPE: PRT
<213> ORGANISM: Artificial Sequence
<220> FEATURE:
<223> OTHER INFORMATION: IMGT 19H11.6/16A9.11 CDR-L2

<400> SEQUENCE: 96

Trp Ser Ser
1

<210> SEQ ID NO 97
<211> LENGTH: 9
<212> TYPE: PRT
<213> ORGANISM: Artificial Sequence
<220> FEATURE:
<223> OTHER INFORMATION: IMGT 19H11.6/16A9.11 CDR-L3

<400> SEQUENCE: 97

Gln Asn Asp Tyr Tyr Tyr Pro Leu Thr
1               5

<210> SEQ ID NO 98
<211> LENGTH: 3
<212> TYPE: PRT
<213> ORGANISM: Artificial Sequence
<220> FEATURE:
<223> OTHER INFORMATION: IMGT 9C8.1/6B9.22 CDR-L2

<400> SEQUENCE: 98

Trp Ala Ser
1

<210> SEQ ID NO 99
<211> LENGTH: 9
<212> TYPE: PRT
<213> ORGANISM: Artificial Sequence
<220> FEATURE:
<223> OTHER INFORMATION: IMGT 9C8.1/6B9.22 CDR-L3

<400> SEQUENCE: 99

Gln Asn Asp Tyr Phe Tyr Pro Phe Thr
1               5

<210> SEQ ID NO 100
<211> LENGTH: 3
```

<212> TYPE: PRT
<213> ORGANISM: Artificial Sequence
<220> FEATURE:
<223> OTHER INFORMATION: IMGT 19G10.14 CDR-L2

<400> SEQUENCE: 100

Gly Ala Ser
1

<210> SEQ ID NO 101
<211> LENGTH: 9
<212> TYPE: PRT
<213> ORGANISM: Artificial Sequence
<220> FEATURE:
<223> OTHER INFORMATION: IMGT 19G10.14 CDR-L3

<400> SEQUENCE: 101

Gln Asn Asp His Phe Tyr Pro Phe Thr
1               5

<210> SEQ ID NO 102
<211> LENGTH: 448
<212> TYPE: PRT
<213> ORGANISM: Artificial Sequence
<220> FEATURE:
<223> OTHER INFORMATION: heavy chain amino acid sequence of humanized
      antibody 1E9.2 hz11

<400> SEQUENCE: 102

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asn Ser
            20                  25                  30

Ala Met Ser Trp Val Arg Gln Ala Pro Gly Lys Gly Leu Glu Trp Val
        35                  40                  45

Ser Thr Ile Ser Ser Gly Asp Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Gln Gly Tyr Gly Asn Ala Leu Asp Tyr Trp Gly Gln Gly Thr
        100                 105                 110

Leu Val Thr Val Ser Ser Ala Ser Thr Lys Gly Pro Ser Val Phe Pro
    115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

```
Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 103
<211> LENGTH: 220
<212> TYPE: PRT
<213> ORGANISM: Artificial Sequence
<220> FEATURE:
<223> OTHER INFORMATION: light chain amino acid sequence of humanized
      antibody 1E9.2 hz11

<400> SEQUENCE: 103

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ser Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Phe Ala Val Tyr Tyr Cys Gln Asn
                85                  90                  95

Asp Tyr Tyr Tyr Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160
```

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 104
<211> LENGTH: 1344
<212> TYPE: DNA
<213> ORGANISM: Artificial Sequence
<220> FEATURE:
<223> OTHER INFORMATION: heavy chain nucleotide sequence of humanized
      antibody 1E9.2 hz11

<400> SEQUENCE: 104

| | | |
|---|---|---|
| gaggtgcagc tggtggagtc cggaggagga ctggtgaagc caggaggctc cctgaggctg | 60 |
| agctgcgccg cttctggctt cagcttttct aactccgcca tgtcttgggt gcggcaggct | 120 |
| ccaggcaagg gactggagtg ggtgagcacc atctccagcg gcgactctta cacatactat | 180 |
| gccgattccg tgaagggcag gttcaccatc agccgggaca cgctaagaa ctccctgtat | 240 |
| ctgcagatga actccctgag ggccgaggac acagccgtgt actattgcgc taggcaggga | 300 |
| tacggaaatg ctctggatta ttggggccag ggcaccctgg tgacagtgtc ttccgcctcc | 360 |
| accaagggcc ctagcgtgtt tccactggct cccagctcta agagcacctc tggaggaaca | 420 |
| gccgctctgg gctgtctggt gaaggattac ttcccagagc ccgtgacagt gtcttggaac | 480 |
| tccggcgccc tgacctccgg agtgcacaca tttcctgctg tgctgcagtc cagcggcctg | 540 |
| tacagcctgt cttccgtggt gaccgtgcca agctcttccc tgggcaccca gacatatatc | 600 |
| tgcaacgtga atcacaagcc atccaataca aaggtggaca gaaaggtgga gcccaagagc | 660 |
| tgtgataaga cccatacatg ccccccttgt cctgctccag agctgctggg cggaccaagc | 720 |
| gtgttcctgt ttccacccaa gcctaaggac ccctgatga tctctagaac ccccgaggtg | 780 |
| acatgcgtgg tggtggacgt gtcccacgag acccccgagg tgaagttcaa ctggtacgtg | 840 |
| gatggcgtgg aggtgcataa tgctaagacc aagccaagag aggagcagta caattctacc | 900 |
| tatcgcgtgg tgtccgtgct gacagtgctg caccaggact ggctgaacgg caaggagtat | 960 |
| aagtgcaagg tgagcaataa ggccctgccc gctcctatcg agaagaccat ctctaaggcc | 1020 |
| aagggccagc ctagagagcc acaggtgtac acactgcctc caagccgcga cgagctgacc | 1080 |
| aagaaccagg tgtctctgac atgtctggtg aagggcttct atccttccga catcgctgtg | 1140 |
| gagtgggaga gcaatggcca gccagagaac aattacaaga ccacaccccc tgtgctggac | 1200 |
| agcgatggct ctttctttct gtatagcaag ctgaccgtgg ataagtctcg ctggcagcag | 1260 |
| ggcaacgtgt ttcctgtag cgtgatgcat gaggccctgc acaatcatta cacacagaag | 1320 |
| tctctgtccc tgagccctgg caag | 1344 |

<210> SEQ ID NO 105
<211> LENGTH: 660
<212> TYPE: DNA
<213> ORGANISM: Artificial Sequence
<220> FEATURE:
<223> OTHER INFORMATION: light chain nucleotide sequence of humanized
      antibody 1E9.2 hz11

<400> SEQUENCE: 105

```
gacatcgtga tgacacagag cccagattct ctggccgtga gcctgggcga gagggctacc    60
atcaattgca agtccagcca gtccctgctg aacagcggca tcagaagaa ctatctgaca   120
tggtaccagc agaagccagg ccagcccct aagctgctga tctattggtc ttccaccagg   180
gagagcggag tgccagaccg gttcagcggc tctggctccg gcacagactt caccctgaca   240
atcagctctc tgcaggccga ggacttcgcc gtgtactatt gccagaacga ttactattac   300
cccctgacct ttggcggcgg cacaaaggtg gagatcaaga gaaccgtggc cgctcctagc   360
gtgttcatct ttccaccctc tgacgagcag ctgaagtctg gcaccgcctc cgtggtgtgc   420
ctgctgaaca atttctatcc cagggaggcc aaggtgcagt ggaaggtgga taatgctctg   480
cagtccggca acagccagga gtctgtgacc gagcaggact ccaaggatag cacatactct   540
ctgtccagca ccctgacact gtctaaggcc gattatgaga agcacaaggt gtacgcttgc   600
gaggtgaccc atcagggcct gtcttcccca gtgacaaagt cctttaatag aggcgagtgt   660
```

<210> SEQ ID NO 106
<211> LENGTH: 447
<212> TYPE: PRT
<213> ORGANISM: Artificial Sequence
<220> FEATURE:
<223> OTHER INFORMATION: heavy chain amino acid sequence of humanized antibody 2C6.9 hz21

<400> SEQUENCE: 106

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Arg Tyr
            20                  25                  30

Gly Val Ser Trp Ile Arg Gln Pro Pro Gly Lys Gly Leu Glu Trp Ile
        35                  40                  45

Gly Val Ile Trp Gly Glu Gly Asn Thr Asn Tyr Asn Pro Ser Leu Lys
    50                  55                  60

Ser Arg Val Thr Ile Ser Lys Asp Ser Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Val Asn Phe Gly Asn Ala Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240
```

```
Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 107
<211> LENGTH: 220
<212> TYPE: PRT
<213> ORGANISM: Artificial Sequence
<220> FEATURE:
<223> OTHER INFORMATION: light chain amino acid sequence of humanized
      antibody 2C6.9 hz21

<400> SEQUENCE: 107

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Phe Ile Phe Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
```

| | 145 | | | 150 | | | 155 | | | 160 | |
|---|---|---|---|---|---|---|---|---|---|---|---|

Gln Ser Gly Asn Ser Gln Glu Ser Val Thr Glu Gln Asp Ser Lys Asp
                          165                      170                      175

Ser Thr Tyr Ser Leu Ser Ser Thr Leu Thr Leu Ser Lys Ala Asp Tyr
                  180                      185                      190

Glu Lys His Lys Val Tyr Ala Cys Glu Val Thr His Gln Gly Leu Ser
            195                      200                      205

Ser Pro Val Thr Lys Ser Phe Asn Arg Gly Glu Cys
            210                      215                      220

<210> SEQ ID NO 108
<211> LENGTH: 1341
<212> TYPE: DNA
<213> ORGANISM: Artificial Sequence
<220> FEATURE:
<223> OTHER INFORMATION: heavy chain nucleotide sequence of humanized
     antibody 2C6.9 hz21

<400> SEQUENCE: 108

```
caggttcagc tgcaagagtc tggacctggc ctggtcaagc cttccgagac actgtctctg      60
acctgcaccg tgtccggctt cagcctgaca agatatggcg tgtcctggat cagacagcct     120
cctggcaaag gcctggaatg gatcggagtg atctggggcg agggcaacac caactacaac     180
cccagcctga gtccagagt gaccatctcc aaggactcct ccaagagcca ggtgtccctg     240
aagctgtcct ctgtgaccgc tgctgatacc gccgtgtact actgcgccag agtgaacttc     300
ggcaacgccc tggattattg gggccagggc acactggtca ccgtgtcatc tgctagcacc     360
aagggaccca gcgttttccc tctggctcca tcctccaaga gcacctctgg tggaacagct     420
gctctgggct gcctggtcaa ggactacttt cctgagcctg tgaccgtgtc ctggaactct     480
ggcgctctga catctggcgt gcacaccttt ccagctgtgc tgcagtcctc tggcctgtac     540
tctctgtcct ccgtcgtgac cgtgccttct agctctctgg gcacccagac ctacatctgc     600
aatgtgaacc acaagccttc caacaccaag gtggacaaga aggtggaacc caagtcctgc     660
gacaagaccc acacctgtcc tccatgtcct gctccagaac tgctcggcgg accttccgtg     720
ttcctgtttc ctccaaagcc taaggacacc ctgatgatct ctcggacccc tgaagtgacc     780
tgcgtggtgg tggatgtgtc tcacgaggac ccagaagtga agttcaattg gtacgtggac     840
ggcgtggaag tgcacaacgc caagaccaag cctagagagg aacagtacaa ctccacctac     900
agagtggtgt ccgtgctgac cgtgctgcac caggattggc tgaacggcaa agagtacaag     960
tgcaaggtgt ccaacaaggc cctgcctgct cctatcgaaa agaccatctc caaggccaag    1020
ggccagccaa gggaaccca ggtttacacc ttgcctccat ctcgggacga gctgaccaag    1080
aaccaggtgt ccctgacctg tctcgtgaag ggcttctacc cctccgacat cgccgtggaa    1140
tgggagtcta atggccagcc tgagaacaac tacaagacaa cccctcctgt gctggactcc    1200
gacggctcat tcttcctgta ctccaagctg acagtggaca gtccagatg gcagcaggc    1260
aacgtgttct cctgctccgt gatgcacgag gccctgcaca atcactacac acagaagtcc    1320
ctgtctctgt ccctggcaa g                                              1341
```

<210> SEQ ID NO 109
<211> LENGTH: 660
<212> TYPE: DNA
<213> ORGANISM: Artificial Sequence
<220> FEATURE:
<223> OTHER INFORMATION: light chain nucleotide sequence of humanized
     antibody 2C6.9 hz21

```
<400> SEQUENCE: 109
gacatcgtga tgacccagtc tccagacagc ctggctgtgt ctctgggcga gagagccacc        60
atcaactgca agtcctctca gtccctgctg aactccggca accagaagaa ctacctgacc       120
tggtatcagc agaagcccgg ccagcctcct aagctgctga tctactgggc ctccaccaga       180
gattctggcg tgcccgatag attctccggc tctggctctg gcaccgactt taccctgaca       240
atcagctccc tgcaggccga ggatgtggcc gtgtactact gccagaacga cttcatcttc       300
ccactgacct tcggcggagg caccaaggtg gaaatcaagc gtacggtggc cgctccttcc       360
gtgttcatct ttccacctag cgacgagcag ctgaagtccg gaacagcctc tgtcgtgtgt       420
ctgctgaaca acttctaccc tcgggaagcc aaggtgcagt ggaaggtgga caatgccctg       480
cagtccggca actcccaaga gtctgtgacc gagcaggact ccaaggacag cacctacagc       540
ctgtcctcca cactgaccct gtccaaggcc gactacgaga agcacaaggt gtacgcctgc       600
gaagtgaccc atcagggcct gtctagccct gtgaccaagt ctttcaaccg gggcgagtgt       660

<210> SEQ ID NO 110
<211> LENGTH: 7
<212> TYPE: PRT
<213> ORGANISM: Artificial Sequence
<220> FEATURE:
<223> OTHER INFORMATION: IMGT 2C6.9-hz21 CDR-H2

<400> SEQUENCE: 110

Ile Trp Gly Glu Gly Asn Thr
1               5

<210> SEQ ID NO 111
<211> LENGTH: 9
<212> TYPE: PRT
<213> ORGANISM: Artificial Sequence
<220> FEATURE:
<223> OTHER INFORMATION: AbM 2C6.9-hz21 CDR-H2

<400> SEQUENCE: 111

Val Ile Trp Gly Glu Gly Asn Thr Asn
1               5
```